United States Patent
Merchant

(10) Patent No.: US 10,093,708 B2
(45) Date of Patent: Oct. 9, 2018

(54) INTERLEUKIN-4 RECEPTOR-BINDING FUSION PROTEINS AND USES THEREOF

(71) Applicant: Medicenna Therapeutics, Inc., Vancouver (CA)

(72) Inventor: Fahar Merchant, Vancouver (CA)

(73) Assignee: Medicenna Therapeutics Inc., Toronto, Ontario (*) Notice: Subject to any disclaimer, the term of this patent is extended or adjusted under 35 U.S.C. 154(b) by 110 days.

(21) Appl. No.: 15/024,785

(22) PCT Filed: Sep. 24, 2014

(86) PCT No.: PCT/CA2014/050915
§ 371 (c)(1),
(2) Date: Mar. 24, 2016

(87) PCT Pub. No.: WO2015/042705
PCT Pub. Date: Apr. 2, 2015

(65) Prior Publication Data
US 2016/0215035 A1 Jul. 28, 2016

Related U.S. Application Data

(60) Provisional application No. 61/881,930, filed on Sep. 24, 2013.

(51) Int. Cl.
| | | |
|---|---|---|
| *C07K 14/47* | (2006.01) | |
| *C07K 14/54* | (2006.01) | |
| *A61K 38/20* | (2006.01) | |
| *A61K 38/17* | (2006.01) | |
| *C12N 5/071* | (2010.01) | |
| *C12N 15/63* | (2006.01) | |
| *A61K 38/19* | (2006.01) | |
| *C12N 5/0783* | (2010.01) | |
| *A61K 38/00* | (2006.01) | |

(52) U.S. Cl.
CPC ...... *C07K 14/5406* (2013.01); *A61K 38/1761* (2013.01); *A61K 38/193* (2013.01); *A61K 38/2026* (2013.01); *C07K 14/4747* (2013.01); *C12N 5/0602* (2013.01); *C12N 5/0636* (2013.01); *C12N 15/63* (2013.01); *A61K 38/00* (2013.01); *C07K 2319/00* (2013.01); *C12N 2501/48* (2013.01)

(58) Field of Classification Search
CPC ............ A61K 2300/00; A61K 38/2026; A61K 38/1761; A61K 38/17; A61K 38/20; A61K 38/2086; C07K 14/54; C07K 14/5406; C07K 14/5437; C07K 14/4747; C07K 2319/00
See application file for complete search history.

(56) References Cited

U.S. PATENT DOCUMENTS

| | | | | |
|---|---|---|---|---|
| 6,011,002 A | * | 1/2000 | Pastan | A61K 47/642 424/85.2 |
| 6,737,511 B1 | * | 5/2004 | Youle | C07K 14/34 424/134.1 |
| 9,512,194 B2 | * | 12/2016 | Garcia | C07K 14/5437 |
| 2005/0106148 A1 | | 5/2005 | Kay et al. | |
| 2010/0183545 A1 | * | 7/2010 | Puri | A61K 31/513 424/85.2 |
| 2010/0317577 A1 | | 12/2010 | Youle | |

FOREIGN PATENT DOCUMENTS

| | | | |
|---|---|---|---|
| WO | WO 01/34645 A2 | | 5/2001 |
| WO | WO-2006074451 A2 | * | 7/2006 |
| WO | WO-2009029601 A2 | * | 3/2009 |
| WO | WO-2010031185 A1 | * | 3/2010 |
| WO | WO-2012054929 A2 | * | 4/2012 |
| WO | WO 2012/139112 A1 | | 10/2012 |
| WO | WO 2013/112871 A1 | | 8/2013 |

OTHER PUBLICATIONS

Bhatia et al. Innovative approaches for enhancing cancer gene therapy. Discovery Medicine 15(84): 309-317, 2013.*
Juengst, E.T. What next for human gene therapy? BMJ 326: 1410-1411, 2003.*
Junttila et al. Redirecting cell-type specific cytokine responses with engineered interleukin-4 superkines. Nature Chemical Biol 8: 990-998, 2012.*
Phillips, A.J. The challenge of gene therapy and DNA delivery. J Pharmacy and Pharmacol 53: 1169-1174, 2001.*
Rubanyi, G.M. The future of human gene therapy. Molecular Aspects Med 22:113-142, 2001.*
Boise et al. "bcl-x, a bcl-2-Related Gene That Functions as a Dominant Regulator of Apoptotic Cell Death" Cell, vol. 74, pp. 597-608 (1993).
Thorpe et al. "Toxicity of diphtheria toxin for lymphoblastoid cells is increased by conjugation to antilymphocytic globulin" Nature, vol. 271, pp. 752-755 (1978).
Bachran et al. "Anthrax Toxin-Mediated Delivery of the Pseudomonas Exotoxin a Enzymatic Domain to the Cytosol of Tumor Cells via Cleavable Ubiquitin Fusions" mBio vol. 4, pp. 201-213 (2013).
Boise et al. "bcl-x, a bcl-2-Related Gene That Functions as a Dominant Regulator of Cell Death" Apoptotic Cell, vol. 74, pp. 597-608 (1993).
Cleary et al "Cloning and structural analysis of cDNAs for bcl-2 and a hybrid bcl-2/immunoglobulin transcript resulting from the t(14;18) translocation" Cell Press, vol. 47, No. 1, pp. 19-28 (1986).

(Continued)

*Primary Examiner* — Bridget E Bunner
(74) *Attorney, Agent, or Firm* — Morgan Lewis & Bockius LLP; Christina A. MacDougall

(57) ABSTRACT

The present invention relates to interleukin-4 receptor binding fusion proteins. More specifically, the invention provides, in part, fusion proteins that include an interleukin-4 receptor binding protein moiety joined to a pro-apoptotic Bcl-2 family member protein moiety.

19 Claims, 12 Drawing Sheets

Figure 1:
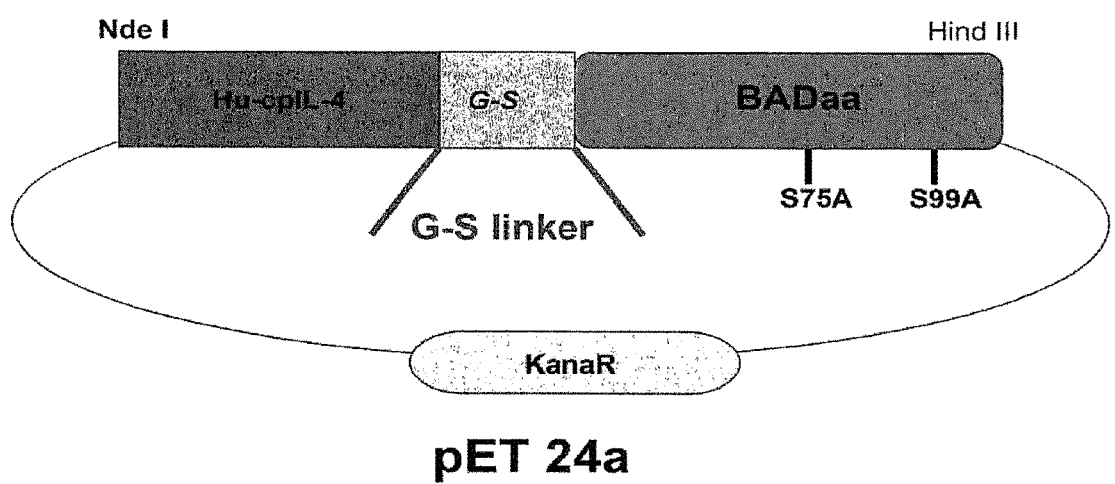
Figure 2:
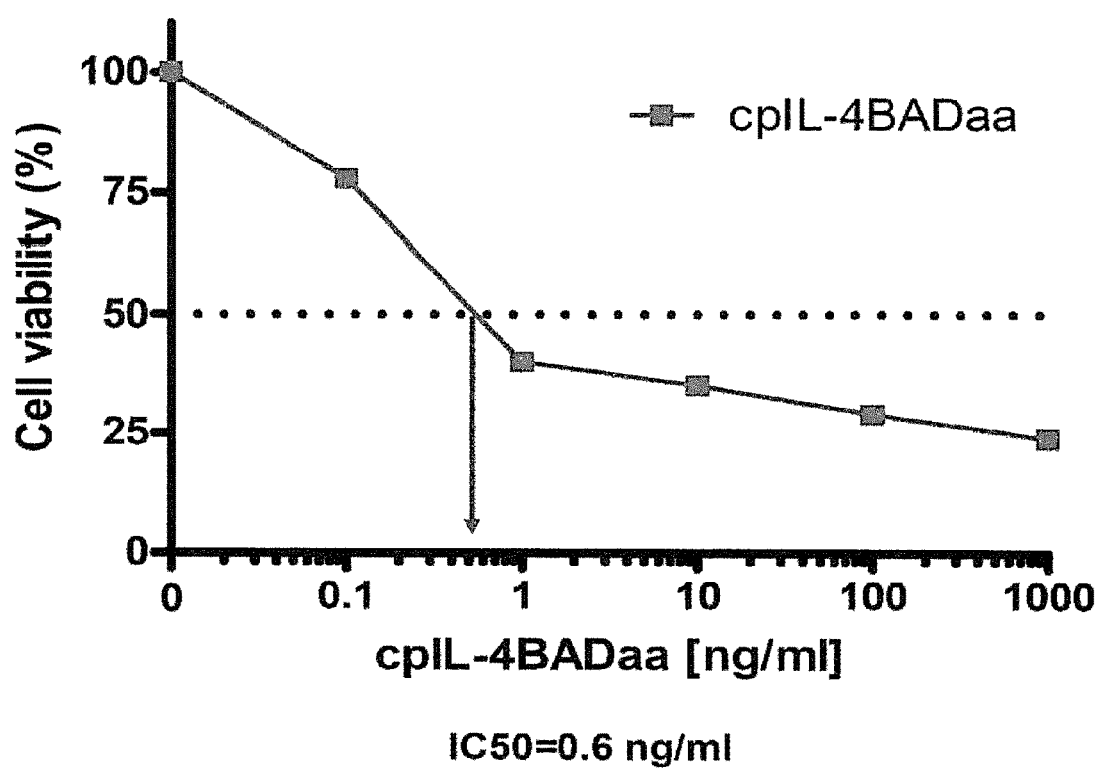
Figure 3:
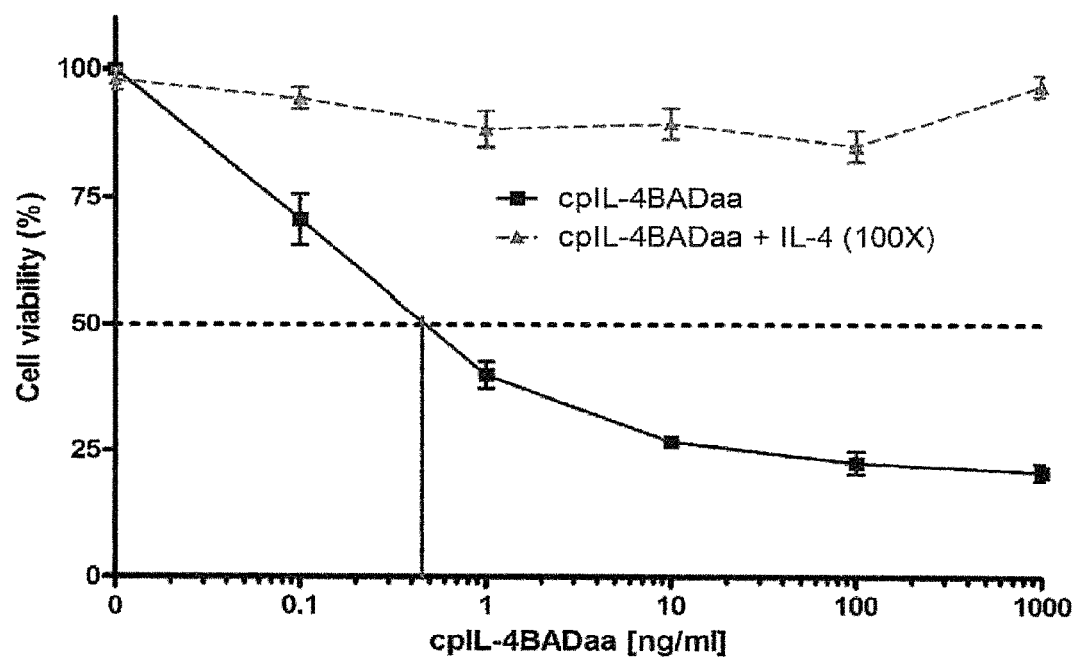
Figure 4:
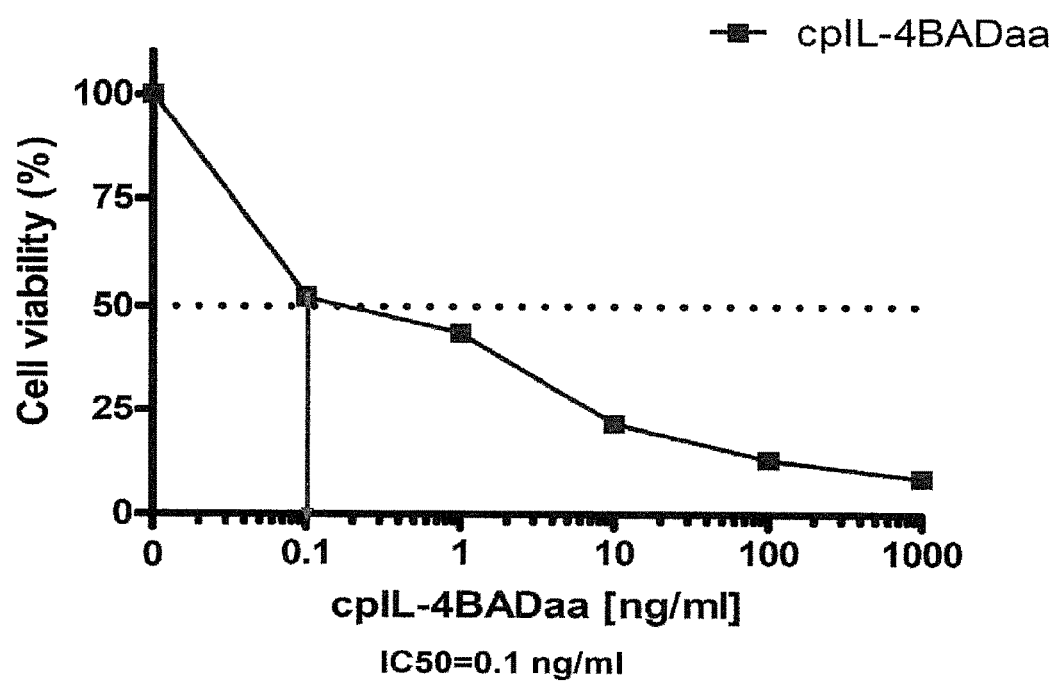

Specification includes a Sequence Listing.

(56) References Cited

OTHER PUBLICATIONS

Diehn et al. "Cancer Stem Cells and Radiotherapy: New Insights Into Tumor Radioresistance" Journal of National Cancer Institute, vol. 98, pp. 1755-1757 (2006).
GenBank Accession No. Q07817, bcl gene apotosis [homo sapiens] Feb. 28, 2018.
GenBank Accession No. Z23115, bcl Xl gene [homo sapiens] Oct. 7, 2008.
Kreitman et al. "Recombinant Toxins Containing Human Granulocyte-Macrophage Colony-Stimulating Factor and Either Pseudomonas Exotoxin or Diphtheria Toxin Kill Gastrointestinal Cancer and Leukemia Cells" Blood vol. 90, pp. 252-259 (1997).
Laske et al. "Tumor regression with regional distribution of the targeted toxin TF-CRM107 in patients with malignant brain tumors" Nature, vol. 3, pp. 1362-1368 (1997).
Lomonosova and Chinnadurai "BH3-only proteins in apoptosis and beyond: an overview" Oncogene, vol. 27, pp. S2-S19 (2009).
Rubin "Neuronal cell death: when, why and how" British Medical Bulletin, vol. 53, Issue 3, pp. 617-631 (1997).
Sakariassen et al. "Cancer Stem Cells as Mediators of Treatment Resistance in Brain Tumors: Status and Controversies" Neoplasia, vol. 9, No. 11, pp. 882-892 (2007).
Shimamura et al. "Interleukin-4 Cytotoxin Therapy Synergizes with Gemcitabine in a Mouse Model of Pancreatic Ductal Adenocarcinoma" Cancer Research, vol. 67, pp. 9903-9912 (2007).
Suga et al. "Transplant Immunosuppression Enhances Efficiency of Adenoviral-Mediated Gene Retransfection: Inhibition of Interferon-y and Immunoglobin G" the Society of Thoracic Surgeons, vol. 73, pp. 1092-1097 (2002).
Thorpe et al. "Toxicity of diphtheria toxin for lymphoblastoid cells is increased by to antilymphocytic globulin" Nature, vol. 271, pp. 752-755 (1978) conjugation.
Tsujimoto and Croce "Analysis of the structure, transcripts, and protein products of bcl-2, the gene involved in human follicular lymphoma" Proc. Natl. Acad. Sci., vol. 83, pp. 5214-5218 (1986).
White "Life, Death, and the Pursuit of Apoptosis" Genes and Development 10, pp. 1-15 (1996).
Yang et al. "Bad, a heterodimeric partner for Bcl-XL and Bcl-2, displaces Bax and promotes cell death" Cell, vol. 80, pp. 285-291 (1995).
Youle et al. "Receptor-mediated uptake of an extracellular Bcl-xL fusion protein inhibits apoptosis" Proceedings of Nat'l Academy of Sciences, vol. 96, pp. 9563-9567 (1999).
Youle et al. "The Cytokine, Granulocyte-Macrophage Colony-stimulating Factor (GM-CSF), Can Deliver Bcl-XL as an Extracellular Fusion Protein to Protect Cells from Apoptosis and Retain Differentiation Induction" The Journal of Biological Chemistry, vol. 282, No. 15, pp. 11246-11254 (2007).

* cited by examiner

IC50 in CFU assay=5ng/ml

**A. 918 bp IL-4Bad cDNA cloned into *Bam*HI and *Xho*I sites of pGW07 expression vector and including a C-terminal polyhistidine tag.**

ATGCACAAATGCGACATTACCCTGCAAGAGATCATTAAGACCCTGAACAGCCTGACCGAGCAAAAGACCCTGTGT
ACCGAACTGACCGTCACGGACATCTTCGCTGCGTCCAAGGACACTACGGAAAAGGAAACGTTCTGTCGTGCGGCG
ACGGTGCTGCGCCAGTTCTACAGCCACCATGAGAAAGATACCCGTTGCCTCGGTGCGACCGCGCAACAGTTCCAC
CGTCACAAACAGCTGATTCGCTTCCTGAAGCGTCTGGATCGCAACCTGTGGGGTTTGGCGGGTCTGAACTCCTGTC
CAGTCAAAGAAGCCAATCAGTCTACGCTGGAAAACTTTTTGGAGCGTCTGAAAACTATCATGCGTGAGAAGTACA
GCAAATGCAGCAGCGGTAGCTTTCAGATCCCGGAATTTGAGCCGAGCGAGCAAGAGGATTCAAGCAGCGCGGAG
CGCGGTCTGGGTCCGAGCCCGGCAGGCGACGGTCCGAGCGGCAGCGGCAAGCATCACCGCCAGGCGCCAGGCCT
GCTGTGGGATGCATCGCATCAACAGGAACAACCGACGAGCAGCAGCCATCATGGTGGCGCTGGTGCGGTTGAGA
TTAGATCGCGCCACTCCGCATATCCTGCCGGCACCGAAGATGACGAAGGCATGGGCGAGGAACCGAGCCCGTTCC
GTGGCCGTAGCCGTGCTGCACCGCCGAATCTGTGGGCCGCACAGCGTTATGGTCGCGAGTTGCGTCGCATGTCCG
ACGAGTTTGTTGACTCCTTCAAGAAAGGTTTACCGCGTCCGAAATCTGCCGGTACCGCGACGCAGATGCGTCAGA
GCAGCAGCTGGACCCGCGTGTTTCAATCTTGGTGGGATCGTAATCTGGGTCGTGGTAGCAGCGCACCGAGCCAAC
ACCACCATCACCATCACTAA (SEQ ID NO: 39)

B. IL-4BAD protein translation. MW 34.2 kDa, pI 8.64. BAD domain is bolded.

MHKCDITLQEIIKTLNSLTEQKTLCTELTVTDIFAASKDTTEKETFCRAATVLRQFYSHHEKDTRCLGATAQQFHRHKQLIR
FLKRLDRNLWGLAGLNSCPVKEANQSTLENFLERLKTIMREKYSKCSSGS**FQIPEFEPSEQEDSSSAERGLGPSPAGDGP
SGSGKHHRQAPGLLWDASHQQEQPTSSSHHGGAGAVEIRSRHSAYPAGTEDDEGMGEEPSPFRGRSRAAPPNLW
AAQRYGRELRRMSDEFVDSFKKGLPRPKSAGTATQMRQSSSWTRVFQSWWDRNLGRGSSAPS**QHHHHHH (SEQ ID NO: 40)

C. 927 bp cpIL-4Bad cDNA cloned into BamH1 and Xho1 sites of pGW07 expression vector and including a C-terminal polyhistidine tag.

ATGGATACCACCGAGAAAGAAACGTTCTGCCGTGCTGCCACTGTCCTGCGCCAGTTTTACAGCCATCACGAAAAG
GACACCCGTTGCCTGGGTGCGACGGCGCAGCAATTCCACCGCCACAAACAGCTGATTCGTTTCCTGAAGCGTCTG
GACCGTAACCTGTGGGGTCTGGCGGGTCTGAACAGCTGTCCAGTGAAAGAAGCGAATCAGAGCACCTTGGAGAA
TTTCCTCGAACGCCTGAAAACCATCATGCGTGAGAAATACAGCAAGTGTTCTAGCGGCGGTAACGGTGGCCACAA
ATGCGATATCACCCTGCAAGAGATCATTAAGACGCTGAACTCCTTGACGGAACAAAAGACCCTGTGTACTGAGCTG
ACGGTCACCGACATTTTCGCGGCGTCCGGTAGCTTTCAGATCCCGGAATTTGAGCCGAGCGAGCAAGAGGATTCA
AGCAGCGCGGAGCGCGGTCTGGGTCCGAGCCCGGCAGGCGACGGTCCGAGCGGCAGCGGCAAGCATCACCGCC
AGGCGCCAGGCCTGCTGTGGGATGCATCGCATCAACAGGAACAACCGACGAGCAGCAGCCATCATGGTGGCGCT
GGTGCGGTTGAGATTAGATCGCGCCACTCCGCATATCCTGCCGGCACCGAAGATGACGAAGGCATGGGCGAGGA
ACCGAGCCCGTTCCGTGGCCGTAGCCGTGCTGCACCGCCGAATCTGTGGGCCGCACAGCGTTATGGTCGCGAGTT
GCGTCGCATGTCCGACGAGTTTGTTGACTCCTTCAAGAAAGGTTTACCGCGTCCGAAATCTGCCGGTACCGCGACG
CAGATGCGTCAGAGCAGCAGCTGGACCCGCGTGTTTCAATCTTGGTGGGATCGTAATCTGGGTCGTGGTAGCAGC
GCACCGAGCCAACACCACCATCACCATCAC (SEQ ID NO: 41)

FIGURE 10

D. cpIL-4BAD protein translation. MW 34.5 kDa, pI 8.46. BAD domain is bolded

MDTTEKETFCRAATVLRQFYSHHEKDTRCLGATAQQFHRHKQLIRFLKRLDRNLWGLAGLNSCPVKEANQSTLENFLER
LKTIMREKYSKCSSGGNGGHKCDITLQEIIKTLNSLTEQKTLCTELTVTDIFAASGSFQIPEFEPSEQEDSSSAERGLGPSPA
GDGPSGSGKHHRQAPGLLWDASHQQEQPTSSSHHGGAGAVEIRSRHSAYPAGTEDDEGMGEEPSPFRGRSRAAP
PNLWAAQRYGRELRRMSDEFVDSFKKGLPRPKSAGTATQMRQSSSWTRVFQSWWDRNLGRGSSAPSQHHHHH
H (SEQ ID NO: 42)

**E. 930 bp cpS4-Bad cDNA cloned into *Bam*HI and *Xho*I sites of pGW07 expression vector and including a C-terminal polyhistidine tag.**

ATGGATACCACCGAAAAAGAAACTTTTTGTCGTGCCGCGACTGTCCTGCGCCAGTTCTACAGCCACCACGAAAAGG
ACACCCGTTGCCTGGGTGCGACCGCTCAACAATTCCATCGCCACAAACAGCTGATTCGTTTCCTGAAACGTCTGGA
TCGCAACCTGTGGGGTCTGGCGGGTTTGAACAGCTGTCCAGTCAAAGAAGCGAACCAGAGCACCCTGGAAAACTT
TCTGGAGCGTCTGCGTGTTATCATGCAGAGCAAGTGGTTCAAGTGCGGTGCGGGTGGCAATGGTGGCCACAAGT
GTGACATTACCTTGCAAGAGATTATCAAAACGCTGAACTCTCTGACCGAGCAAAAGACGCTGTGCACCGAGCTGA
CGGTGACGGACATCTTCGCGGCGTCCGGTAGCTTTCAGATCCCGGAATTTGAGCCGAGCGAGCAAGAGGATTCAA
GCAGCGCGGAGCGCGGTCTGGGTCCGAGCCCGGCAGGCGACGGTCCGAGCGGCAGCGGCAAGCATCACCGCCA
GGCGCCAGGCCTGCTGTGGGATGCATCGCATCAACAGGAACAACCGACGAGCAGCAGCCATCATGGTGGCGCTG
GTGCGGTTGAGATTAGATCGCGCCACTCCGCATATCCTGCCGGCACCGAAGATGACGAAGGCATGGGCGAGGAA
CCGAGCCCGTTCCGTGGCCGTAGCCGTGCTGCACCGCCGAATCTGTGGGCCGCACAGCGTTATGGTCGCGAGTTG
CGTCGCATGTCCGACGAGTTTGTTGACTCCTTCAAGAAAGGTTTACCGCGTCCGAAATCTGCCGGTACCGCGACGC
AGATGCGTCAGAGCAGCAGCTGGACCCGCGTGTTTCAATCTTGGTGGGATCGTAATCTGGGTCGTGGTAGCAGCG
CACCGAGCCAACACCACCATCACCATCACTAA (SEQ ID NO:43)

F. cpS4-BAD protein translation. MW 34.5 kDa, pI 8.47. BAD domain is bolded

MDTTEKETFCRAATVLRQFYSHHEKDTRCLGATAQQFHRHKQLIRFLKRLDRNLWGLAGLNSCPVKEANQSTLENFLER
LRVIMQSKWFKCGAGGNGGHKCDITLQEIIKTLNSLTEQKTLCTELTVTDIFAASGSFQIPEFEPSEQEDSSSAERGLGPS
PAGDGPSGSGKHHRQAPGLLWDASHQQEQPTSSSHHGGAGAVEIRSRHSAYPAGTEDDEGMGEEPSPFRGRSRA
APPNLWAAQRYGRELRRMSDEFVDSFKKGLPRPKSAGTATQMRQSSSWTRVFQSWWDRNLGRGSSAPSQHHH
HHH (SEQ ID NO: 44 with a poly-histidine tag)

FIGURE 10 (contd.)

A. 927 bp pKFR4-BAD-H6 cDNA cloned into BamHI and XhoI sites NdeI/XhoI sites of a pET-21a(+) expression vector and including a C-terminal polyhistidine tag.

ATGGATACTACCGAGAAAGAAACGTTTTGCCGTGCTGCGACCGTCCTGCGTCAGTTCTACA
GCCACCACGAAAAGGACACCCGCTGTCTGGGTGCGACTGCCCAACAATTCCATCGTCACA
AACAGCTGATTCGTTTCCTGAAGCGTCTGGACCGCAACCTGTGGGGTCTGGCGGGCTTGA
ACTCCTGCCCAGTCAAAGAAGCGAACCAAAGCACCCTGGAAAACTTCTTGGAGCGTCTGA
AAACGATCATGAAAGAGAAGTTCCGCAAGTGTAGCAGCGGTGGTAATGGTGGCCACAAGT
GCGACATTACGCTGCAGGAAATCATTAAGACCCTGAACTCTCTGACCGAGCAGAAACCCT
CTGTACCGAGCTGACGGTGACGGATATCTTTGCGGCGAGCGGTAGCTTTCAGATCCCGGA
ATTTGAGCCGAGCGAGCAAGAGGATTCAAGCAGCGCGGAGCGCGGTCTGGGTCCGAGCC
CGGCAGGCGACGGTCCGAGCGGCAGCGGCAAGCATCACCGCCAGGCGCCAGGCCTGCT
GTGGGATGCATCGCATCAACAGGAACAACCGACGAGCAGCAGCCATCATGGTGGCGCTG
GTGCGGTTGAGATTAGATCGCGCCACTCCGCATATCCTGCCGGCACCGAAGATGACGAAG
GCATGGGCGAGGAACCGAGCCCGTTCCGTGGCCGTAGCCGTGCTGCACCGCCGAATCTG
TGGGCCGCACAGCGTTATGGTCGCGAGTTGCGTCGCATGTCCGACGAGTTTGTTGACTCC
TTCAAGAAAGGTTTACCGCGTCCGAAATCTGCCGGTACCGCGACGCAGATGCGTCAGAGC
AGCAGCTGGACCCGCGTGTTTCAATCTTGGTGGGATCGTAATCTGGGTCGTGGTAGCAGC
GCACCGAGCCAACACCACCATCACCATCAC (SEQ ID NO: 45)

B. pKFR4-BAD-H6 protein translation. BAD domain is bolded

MDTTEKETFCRAATVLRQFYSHHEKDTRCLGATAQQFHRHKQLIRFLKRLDRNLWGLAGLNSC
PVKEANQSTLENFLERLKTIMKEKFRKCSSGGNGGHKCDITLQEIIKTLNSLTEQKTLCTELTVT
DIFAASGSF**QIPEFEPSEQEDSSSAERGLGPSPAGDGPSGSGKHHRQAPGLLWDASHQQEQ
PTSSSHHGGAGAVEIRSRHSAYPAGTEDDEGMGEEPSPFRGRSRAAPPNLWAAQRYGREL
RRMSDEFVDSFKKGLPRPKSAGTATQMRQSSSWTRVFQSWWDRNLGRGSSAPS**QHHHHH
H (SEQ ID NO: 46)

FIGURE 11

SEQUENCE LISTING

<160> NUMBER OF SEQ ID NOS: 46

<210> SEQ ID NO 1
<211> LENGTH: 130

<212> TYPE: PRT
<213> ORGANISM: Artificial Sequence
<220> FEATURE:
<223> OTHER INFORMATION: IL-4 including an additional methionine at the
      N-terminus

<400> SEQUENCE: 1

Met His Lys Cys Asp Ile Thr Leu Gln Glu Ile Ile Lys Thr Leu Asn
1               5                   10                  15

Ser Leu Thr Glu Gln Lys Thr Leu Cys Thr Glu Leu Thr Val Thr Asp
            20                  25                  30

Ile Phe Ala Ala Ser Lys Asn Thr Thr Glu Lys Glu Thr Phe Cys Arg
        35                  40                  45

Ala Ala Thr Val Leu Arg Gln Phe Tyr Ser His His Glu Lys Asp Thr
    50                  55                  60

Arg Cys Leu Gly Ala Thr Ala Gln Gln Phe His Arg His Lys Gln Leu
65                  70                  75                  80

Ile Arg Phe Leu Lys Arg Leu Asp Arg Asn Leu Trp Gly Leu Ala Gly
                85                  90                  95

Leu Asn Ser Cys Pro Val Lys Glu Ala Asn Gln Ser Thr Leu Glu Asn
            100                 105                 110

Phe Leu Glu Arg Leu Lys Thr Ile Met Arg Glu Lys Tyr Ser Lys Cys
        115                 120                 125

Ser Ser
130

<210> SEQ ID NO 2
<211> LENGTH: 130
<212> TYPE: PRT
<213> ORGANISM: Artificial Sequence
<220> FEATURE:
<223> OTHER INFORMATION: IL-4 including an additional methionine at the
      N-terminus

<400> SEQUENCE: 2

Met His Lys Cys Asp Ile Thr Leu Gln Glu Ile Ile Lys Thr Leu Asn
1               5                   10                  15

Ser Leu Thr Glu Gln Lys Thr Leu Cys Thr Glu Leu Thr Val Thr Asp
            20                  25                  30

Ile Phe Ala Ala Ser Lys Asp Thr Thr Glu Lys Glu Thr Phe Cys Arg
        35                  40                  45

Ala Ala Thr Val Leu Arg Gln Phe Tyr Ser His His Glu Lys Asp Thr
    50                  55                  60

Arg Cys Leu Gly Ala Thr Ala Gln Gln Phe His Arg His Lys Gln Leu
65                  70                  75                  80

Ile Arg Phe Leu Lys Arg Leu Asp Arg Asn Leu Trp Gly Leu Ala Gly
                85                  90                  95

Leu Asn Ser Cys Pro Val Lys Glu Ala Asn Gln Ser Thr Leu Glu Asn
            100                 105                 110

Phe Leu Glu Arg Leu Lys Thr Ile Met Arg Glu Lys Tyr Ser Lys Cys
        115                 120                 125

Ser Ser
130

<210> SEQ ID NO 3
<211> LENGTH: 134
<212> TYPE: PRT
<213> ORGANISM: Artificial Sequence
<220> FEATURE:

<223> OTHER INFORMATION: circularly permuted IL-4

<400> SEQUENCE: 3

Met Asp Thr Thr Glu Lys Glu Thr Phe Cys Arg Ala Ala Thr Val Leu
1               5                   10                  15

Arg Gln Phe Tyr Ser His His Glu Lys Asp Thr Arg Cys Leu Gly Ala
            20                  25                  30

Thr Ala Gln Gln Phe His Arg His Lys Gln Leu Ile Arg Phe Leu Lys
        35                  40                  45

Arg Leu Asp Arg Asn Leu Trp Gly Leu Ala Gly Leu Asn Ser Cys Pro
    50                  55                  60

Val Lys Glu Ala Asn Gln Ser Thr Leu Glu Asn Phe Leu Glu Arg Leu
65                  70                  75                  80

Lys Thr Ile Met Arg Glu Lys Tyr Ser Lys Cys Ser Ser Gly Gly Asn
                85                  90                  95

Gly Gly His Lys Cys Asp Ile Thr Leu Gln Glu Ile Ile Lys Thr Leu
            100                 105                 110

Asn Ser Leu Thr Glu Gln Lys Thr Leu Cys Thr Glu Leu Thr Val Thr
            115                 120                 125

Asp Ile Phe Ala Ala Ser
    130

<210> SEQ ID NO 4
<211> LENGTH: 134
<212> TYPE: PRT
<213> ORGANISM: Artificial Sequence
<220> FEATURE:
<223> OTHER INFORMATION: circularly permuted "RGA" IL-4 variant

<400> SEQUENCE: 4

Met Asp Thr Thr Glu Lys Glu Thr Phe Cys Arg Ala Ala Thr Val Leu
1               5                   10                  15

Arg Gln Phe Tyr Ser His His Glu Lys Asp Thr Arg Cys Leu Gly Ala
            20                  25                  30

Thr Ala Gln Gln Phe His Arg His Lys Gln Leu Ile Arg Phe Leu Lys
        35                  40                  45

Arg Leu Asp Arg Asn Leu Trp Gly Leu Ala Gly Leu Asn Ser Cys Pro
    50                  55                  60

Val Lys Glu Ala Asn Gln Ser Thr Leu Glu Asn Phe Leu Glu Arg Leu
65                  70                  75                  80

Arg Val Ile Met Gln Ser Lys Trp Phe Lys Cys Gly Ala Gly Gly Asn
                85                  90                  95

Gly Gly His Lys Cys Asp Ile Thr Leu Gln Glu Ile Ile Lys Thr Leu
            100                 105                 110

Asn Ser Leu Thr Glu Gln Lys Thr Leu Cys Thr Glu Leu Thr Val Thr
            115                 120                 125

Asp Ile Phe Ala Ala Ser
    130

<210> SEQ ID NO 5
<211> LENGTH: 134
<212> TYPE: PRT
<213> ORGANISM: Artificial Sequence
<220> FEATURE:
<223> OTHER INFORMATION: circularly permuted "KFR" IL-4 variant

<400> SEQUENCE: 5

Met Asp Thr Thr Glu Lys Glu Thr Phe Cys Arg Ala Ala Thr Val Leu

```
1               5                   10                  15
Arg Gln Phe Tyr Ser His His Glu Lys Asp Thr Arg Cys Leu Gly Ala
                20                  25                  30

Thr Ala Gln Gln Phe His Arg His Lys Gln Leu Ile Arg Phe Leu Lys
            35                  40                  45

Arg Leu Asp Arg Asn Leu Trp Gly Leu Ala Gly Leu Asn Ser Cys Pro
        50                  55                  60

Val Lys Glu Ala Asn Gln Ser Thr Leu Glu Asn Phe Leu Glu Arg Leu
65                  70                  75                  80

Lys Thr Ile Met Lys Glu Lys Phe Arg Lys Cys Ser Ser Gly Gly Asn
                85                  90                  95

Gly Gly His Lys Cys Asp Ile Thr Leu Gln Glu Ile Ile Lys Thr Leu
                100                 105                 110

Asn Ser Leu Thr Glu Gln Lys Thr Leu Cys Thr Glu Leu Thr Val Thr
            115                 120                 125

Asp Ile Phe Ala Ala Ser
            130

<210> SEQ ID NO 6
<211> LENGTH: 133
<212> TYPE: PRT
<213> ORGANISM: Artificial Sequence
<220> FEATURE:
<223> OTHER INFORMATION: circularly permuted "KF" IL-4 variant

<400> SEQUENCE: 6

Met Asp Thr Thr Glu Lys Glu Thr Phe Cys Arg Ala Ala Thr Val Leu
1               5                   10                  15

Arg Gln Phe Tyr Ser His His Glu Lys Asp Thr Arg Cys Leu Gly Ala
                20                  25                  30

Thr Ala Gln Gln Phe His Arg His Lys Gln Leu Ile Arg Phe Leu Lys
            35                  40                  45

Arg Leu Asp Arg Asn Leu Trp Gly Leu Ala Gly Leu Asn Ser Cys Pro
        50                  55                  60

Val Lys Glu Ala Asn Gln Ser Thr Leu Glu Asn Phe Leu Glu Arg Leu
65                  70                  75                  80

Lys Thr Ile Met Lys Glu Lys Phe Lys Cys Ser Ser Gly Gly Asn Gly
                85                  90                  95

Gly His Lys Cys Asp Ile Thr Leu Gln Glu Ile Ile Lys Thr Leu Asn
                100                 105                 110

Ser Leu Thr Glu Gln Lys Thr Leu Cys Thr Glu Leu Thr Val Thr Asp
            115                 120                 125

Ile Phe Ala Ala Ser
        130

<210> SEQ ID NO 7
<211> LENGTH: 114
<212> TYPE: PRT
<213> ORGANISM: Artificial Sequence
<220> FEATURE:
<223> OTHER INFORMATION: IL-13 including an additional methionine at the
      N-terminus

<400> SEQUENCE: 7

Met Pro Gly Pro Val Pro Pro Ser Thr Ala Leu Arg Glu Leu Ile Glu
1               5                   10                  15

Glu Leu Val Asn Ile Thr Gln Asn Gln Lys Ala Pro Leu Cys Asn Gly
                20                  25                  30
```

-continued

Ser Met Val Trp Ser Ile Asn Leu Thr Ala Gly Met Tyr Cys Ala Ala
         35                  40                  45

Leu Glu Ser Leu Ile Asn Val Ser Gly Cys Ser Ala Ile Glu Lys Thr
 50                  55                  60

Gln Arg Met Leu Ser Gly Phe Cys Pro His Lys Val Ser Ala Gly Gln
 65                  70                  75                  80

Phe Ser Ser Leu His Val Arg Asp Thr Lys Ile Glu Val Ala Gln Phe
                 85                  90                  95

Val Lys Asp Leu Leu Leu His Leu Lys Lys Leu Phe Arg Glu Gly Gln
                100                 105                 110

Phe Asn

<210> SEQ ID NO 8
<211> LENGTH: 114
<212> TYPE: PRT
<213> ORGANISM: Artificial Sequence
<220> FEATURE:
<223> OTHER INFORMATION: "A11" variant IL-13

<400> SEQUENCE: 8

Met Pro Gly Pro Val Pro Pro Ser Thr Ala Val Arg Glu Leu Ile Glu
 1               5                  10                  15

Glu Leu Ile Asn Ile Thr Gln Asn Gln Lys Ala Pro Leu Cys Asn Gly
                 20                  25                  30

Ser Met Val Trp Ser Ile Asn Arg Thr Ala Gly Met Tyr Cys Ala Ala
         35                  40                  45

Leu Glu Ser Leu Ile Asn Val Ser Gly Cys Ser Ala Ile Glu Lys Thr
 50                  55                  60

Gln Arg Met Leu Ser Gly Phe Cys Pro His Lys Val Ser Ala Gly Gln
 65                  70                  75                  80

Phe Ser Ser Leu His Val Arg Ser Ser Lys Ile Glu Val Ala Gln Phe
                 85                  90                  95

Val Lys Asp Leu Leu Phe His Leu Arg Thr Leu Phe Arg Glu Gly Gln
                100                 105                 110

Phe Asn

<210> SEQ ID NO 9
<211> LENGTH: 114
<212> TYPE: PRT
<213> ORGANISM: Artificial Sequence
<220> FEATURE:
<223> OTHER INFORMATION: "DN" variant IL-13

<400> SEQUENCE: 9

Met Pro Gly Pro Val Pro Pro Ser Thr Ala Val Arg Ala Leu Ile Glu
 1               5                  10                  15

Glu Leu Ile Asn Ile Thr Gln Asn Gln Lys Ala Pro Leu Cys Asn Gly
                 20                  25                  30

Ser Met Val Trp Ser Ile Asn Leu Thr Ala Gly Met Tyr Cys Ala Ala
         35                  40                  45

Leu Glu Ser Leu Ile Asn Val Ser Gly Cys Ser Ala Ile Glu Lys Thr
 50                  55                  60

Gln Asp Met Leu Ser Gly Phe Cys Pro His Lys Val Ser Ala Gly Gln
 65                  70                  75                  80

Phe Ser Ser Leu His Val Arg Ser Ser Lys Ile Glu Val Ala Gln Phe
                 85                  90                  95

```
Val Lys Asp Leu Leu Phe His Leu Arg Thr Leu Phe Arg Glu Gly Gln
            100                 105                 110

Phe Asn

<210> SEQ ID NO 10
<211> LENGTH: 117
<212> TYPE: PRT
<213> ORGANISM: Artificial Sequence
<220> FEATURE:
<223> OTHER INFORMATION: circularly permuted IL-13

<400> SEQUENCE: 10

Met Tyr Cys Ala Ala Leu Glu Ser Leu Ile Asn Val Ser Gly Cys Ser
1               5                   10                  15

Ala Ile Glu Lys Thr Gln Arg Met Leu Ser Gly Phe Cys Pro His Lys
            20                  25                  30

Val Ser Ala Gly Gln Phe

<223> OTHER INFORMATION: circularly permuted IL-13 "A11" variant

<400> SEQUENCE: 12

Met Tyr Cys Ala Ala Leu Glu Ser Leu Ile Asn Val Ser Gly Cys Ser
1               5                   10                  15

Ala Ile Glu Lys Thr Gln Arg Met Leu Ser Gly Phe Cys Pro His Lys
            20                  25                  30

Val Ser Ala Gly Gln Phe Ser Ser Leu His Val Arg Ser Ser Lys Ile
        35                  40                  45

Glu Val Ala Gln Phe Val Lys Asp Leu Leu Phe His Leu Arg Thr Leu
    50                  55                  60

Phe Arg Glu Gly Gln Phe Asn Gly Gly Ser Gly Pro Gly Pro Val Pro
65                  70                  75                  80

Pro Ser Thr Ala Val Arg Glu Leu Ile Glu Glu Leu Ile Asn Ile Thr
                85                  90                  95

Gln Asn Gln Lys Ala Pro Leu Cys Asn Gly Ser Met Val Trp Ser Ile
            100                 105                 110

Asn Arg Thr Ala Gly
        115

<210> SEQ ID NO 13
<211> LENGTH: 118
<212> TYPE: PRT
<213> ORGANISM: Artificial Sequence
<220> FEATURE:
<223> OTHER INFORMATION: circularly permuted IL-13

<400> SEQUENCE: 13

Met Tyr Cys Ala Ala Leu Glu Ser Leu Ile Asn Val Ser Gly Cys Ser
1               5                   10                  15

Ala Ile Glu Lys Thr Gln Arg Met Leu Ser Gly Phe Cys Pro His Lys
            20                  25                  30

Val Ser Ala Gly Gln Phe Ser Ser Leu His Val Arg Ser Ser Lys Ile
        35                  40                  45

Glu Val Ala Gln Phe Val Lys Asp Leu Leu Phe His Leu Arg Thr Leu
    50                  55                  60

Phe Arg Glu Gly Gln Phe Asn Gly Gly Ser Gly Met Pro Gly Pro Val
65                  70                  75                  80

Pro Pro Ser Thr Ala Val Arg Glu Leu Ile Glu Glu Leu Ile Asn Ile
                85                  90                  95

Thr Gln Asn Gln Lys Ala Pro Leu Cys Asn Gly Ser Met Val Trp Ser
            100                 105                 110

Ile Asn Arg Thr Ala Gly
        115

<210> SEQ ID NO 14
<211> LENGTH: 117
<212> TYPE: PRT
<213> ORGANISM: Artificial Sequence
<220> FEATURE:
<223> OTHER INFORMATION: circularly permuted IL-13 "DN" variant

<400> SEQUENCE: 14

Met Tyr Cys Ala Ala Leu Glu Ser Leu Ile Asn Val Ser Gly Cys Ser
1               5                   10                  15

Ala Ile Glu Lys Thr Gln Asp Met Leu Ser Gly Phe Cys Pro His Lys
            20                  25                  30

Val Ser Ala Gly Gln Phe Ser Ser Leu His Val Arg Ser Ser Lys Ile 35                  40                  45

Glu Val Ala Gln Phe Val Lys Asp Leu Leu Phe His Leu Arg Thr Leu
             50                  55                  60

Phe Arg Glu Gly Gln Phe Asn Gly Gly Ser Gly Pro Gly Pro Val Pro
 65                  70                  75                  80

Pro Ser Thr Ala Val Arg Ala Leu Ile Glu Leu Ile Asn Ile Thr
                 85                  90                  95

Gln Asn Gln Lys Ala Pro Leu Cys Asn Gly Ser Met Val Trp Ser Ile
                100                 105                 110

Asn Leu Thr Ala Gly
        115

<210> SEQ ID NO 15
<211> LENGTH: 118
<212> TYPE: PRT
<213> ORGANISM: Artificial Sequence
<220> FEATURE:
<223> OTHER INFORMATION: circular permuted IL-13

<400> SEQUENCE: 15

Met Tyr Cys Ala Ala Leu Glu Ser Leu Ile Asn Val Ser Gly Cys Ser
 1               5                  10                  15

Ala Ile Glu Lys Thr Gln Asp Met Leu Ser Gly Phe Cys Pro His Lys
                20                  25                  30

Val Ser Ala Gly Gln Phe Ser Ser Leu His Val Arg Ser Ser Lys Ile
             35                  40                  45

Glu Val Ala Gln Phe Val Lys Asp Leu Leu Phe His Leu Arg Thr Leu
             50                  55                  60

Phe Arg Glu Gly Gln Phe Asn Gly Gly Ser Gly Met Pro Gly Pro Val
 65                  70                  75                  80

Pro Pro Ser Thr Ala Val Arg Ala Leu Ile Glu Leu Ile Asn Ile
                 85                  90                  95

Thr Gln Asn Gln Lys Ala Pro Leu Cys Asn Gly Ser Met Val Trp Ser
                100                 105                 110

Ile Asn Leu Thr Ala Gly
        115

<210> SEQ ID NO 16
<211> LENGTH: 167
<212> TYPE: PRT
<213> ORGANISM: Homo sapiens

<400> SEQUENCE: 16

Phe Gln Ile Pro Glu Phe Glu Pro Ser Glu Gln Glu Asp Ser Ser Ser
 1               5                  10                  15

Ala Glu Arg Gly Leu Gly Pro Ser Pro Ala Gly Asp Gly Pro Ser Gly
                20                  25                  30

Ser Gly Lys His His Arg Gln Ala Pro Gly Leu Leu Trp Asp Ala Ser
             35                  40                  45

His Gln Gln Glu Gln Pro Thr Ser Ser Ser His His Gly Gly Ala Gly
             50                  55                  60

Ala Val Glu Ile Arg Ser Arg His Ser Ser Tyr Pro Ala Gly Thr Glu
 65                  70                  75                  80

Asp Asp Glu Gly Met Gly Glu Glu Pro Ser Pro Phe Arg Gly Arg Ser
                 85                  90                  95

Arg Ala Ala Pro Pro Asn Leu Trp Ala Ala Gln Arg Tyr Gly Arg Glu
                100                 105                 110

```
Leu Arg Arg Met Ser Asp Glu Phe Val Asp Ser Phe Lys Lys Gly Leu
            115                 120                 125

Pro Arg Pro Lys Ser Ala Gly Thr Ala Thr Gln Met Arg Gln Ser Ser
        130                 135                 140

Ser Trp Thr Arg Val Phe Gln Ser Trp Trp Asp Arg Asn Leu Gly Arg
145                 150                 155                 160

Gly Ser Ser Ala Pro Ser Gln
                165
```

<210> SEQ ID NO 17
<211> LENGTH: 167
<212> TYPE: PRT
<213> ORGANISM: Artificial Sequence
<220> FEATURE:
<223> OTHER INFORMATION: variant Bad

<400> SEQUENCE: 17

```
Phe Gln Ile Pro Glu Phe Glu Pro Ser Glu Gln Glu Asp Ser Ser Ser
1               5                   10                  15

Ala Glu Arg Gly Leu Gly Pro Ser Pro Ala Gly Asp Gly Pro Ser Gly
            20                  25                  30

Ser Gly Lys His His Arg Gln Ala Pro Gly Leu Leu Trp Asp Ala Ser
        35                  40                  45

His Gln Gln Glu Gln Pro Thr Ser Ser Ser His His Gly Gly Ala Gly
    50                  55                  60

Ala Val Glu Ile Arg Ser Arg His Ser Ala Tyr Pro Ala Gly Thr Glu
65                  70                  75                  80

Asp Asp Glu Gly Met Gly Glu Glu Pro Ser Pro Phe Arg Gly Arg Ser
                85                  90                  95

Arg Ala Ala Pro Pro Asn Leu Trp Ala Ala Gln Arg Tyr Gly Arg Glu
            100                 105                 110

Leu Arg Arg Met Ser Asp Glu Phe Val Asp Ser Phe Lys Lys Gly Leu
        115                 120                 125

Pro Arg Pro Lys Ser Ala Gly Thr Ala Thr Gln Met Arg Gln Ser Ser
    130                 135                 140

Ser Trp Thr Arg Val Phe Gln Ser Trp Trp Asp Arg Asn Leu Gly Arg
145                 150                 155                 160

Gly Ser Ser Ala Pro Ser Gln
                165
```

<210> SEQ ID NO 18
<211> LENGTH: 167
<212> TYPE: PRT
<213> ORGANISM: Homo sapiens

<400> SEQUENCE: 18

```
Phe Gln Ile Pro Glu Phe Glu Pro Ser Glu Gln Glu Asp Ser Ser Ser
1               5                   10                  15

Ala Glu Arg Gly Leu Gly Pro Ser Pro Ala Gly Asp Gly Pro Ser Gly
            20                  25                  30

Ser Gly Lys His His Arg Gln Ala Pro Gly Leu Leu Trp Asp Ala Ser
        35                  40                  45

His Gln Gln Glu Gln Pro Thr Ser Ser Ser His His Gly Gly Ala Gly
    50                  55                  60

Ala Val Glu Ile Arg Ser Arg His Ser Ser Tyr Pro Ala Gly Thr Glu
65                  70                  75                  80
```

```
Asp Asp Glu Gly Met Gly Glu Glu Pro Ser Pro Phe Arg Gly Arg Ser
                85                  90                  95

Arg Ser Ala Pro Pro Asn Leu Trp Ala Ala Gln Arg Tyr Gly Arg Glu
            100                 105                 110

Leu Arg Arg Met Ser Asp Glu Phe Val Asp Ser Phe Lys Lys Gly Leu
        115                 120                 125

Pro Arg Pro Lys Ser Ala Gly Thr Ala Thr Gln Met Arg Gln Ser Ser
    130                 135                 140

Ser Trp Thr Arg Val Phe Gln Ser Trp Trp Asp Arg Asn Leu Gly Arg
145                 150                 155                 160

Gly Ser Ser Ala Pro Ser Gln
                165

<210> SEQ ID NO 19
<211> LENGTH: 167
<212> TYPE: PRT
<213> ORGANISM: Homo sapiens

<400> SEQUENCE: 19

Phe Gln Ile Pro Glu Phe Glu Pro Ser Glu Gln Glu Asp Ser Ser Ser
1               5                   10                  15

Ala Glu Arg Gly Leu Gly Pro Ser Pro Ala Gly Asp Gly Pro Ser Gly
            20                  25                  30

Ser Gly Lys His His Arg Gln Ala Pro Gly Leu Leu Trp Asp Ala Ser
        35                  40                  45

His Gln Gln Glu Gln Pro Thr Ser Ser Ser His His Gly Gly Ala Gly
    50                  55                  60

Ala Val Glu Ile Arg Ser Arg His Ser Ser Tyr Pro Ala Gly Thr Glu
65                  70                  75                  80

Asp Asp Glu Gly Met Gly Glu Glu Pro Ser Pro Phe Arg Gly Arg Ser
                85                  90                  95

Arg Ser Ala Pro Pro Asn Leu Trp Ala Ala Gln Arg Tyr Gly Arg Glu
            100                 105                 110

Leu Arg Arg Met Ser Asp Glu Phe Val Asp Ser Phe Lys Lys Gly Leu
        115                 120                 125

Pro Arg Pro Lys Ser Ala Gly Thr Ala Thr Gln Met Arg Gln Ser Ser
    130                 135                 140

Ser Trp Thr Arg Val Phe Gln Ser Trp Trp Asp Arg Asn Leu Gly Arg
145                 150                 155                 160

Gly Ser Ser Ala Pro Ser Gln
                165

<210> SEQ ID NO 20
<211> LENGTH: 159
<212> TYPE: PRT
<213> ORGANISM: Homo sapiens

<400> SEQUENCE: 20

Ser Glu Val Arg Pro Leu Ser Arg Asp Ile Leu Met Glu Thr Leu Leu
1               5                   10                  15

Tyr Glu Gln Leu Leu Glu Pro Pro Thr Met Glu Val Leu Gly Met Thr
            20                  25                  30

Asp Ser Glu Glu Asp Leu Asp Pro Met Glu Asp Phe Asp Ser Leu Glu
        35                  40                  45

Cys Met Glu Gly Ser Asp Ala Leu Ala Leu Arg Leu Ala Cys Ile Gly
    50                  55                  60
```

Asp Glu Met Asp Val Ser Leu Arg Ala Pro Arg Leu Ala Gln Leu Ser
65                  70                  75                  80

Glu Val Ala Met His Ser Leu Gly Leu Ala Phe Ile Tyr Asp Gln Thr
                85                  90                  95

Glu Asp Ile Arg Asp Val Leu Arg Ser Phe Met Asp Gly Phe Thr Thr
            100                 105                 110

Leu Lys Glu Asn Ile Met Arg Phe Trp Arg Ser Pro Asn Pro Gly Ser
        115                 120                 125

Trp Val Ser Cys Glu Gln Val Leu Leu Ala Leu Leu Leu Leu Leu Ala
    130                 135                 140

Leu Leu Leu Pro Leu Leu Ser Gly Gly Leu His Leu Leu Leu Lys
145                 150                 155

<210> SEQ ID NO 21
<211> LENGTH: 194
<212> TYPE: PRT
<213> ORGANISM: Homo sapiens

<400> SEQUENCE: 21

Asp Cys Glu Val Asn Asn Gly Ser Ser Leu Arg Asp Glu Cys Ile Thr
1               5                   10                  15

Asn Leu Leu Val Phe Gly Phe Leu Gln Ser Cys Ser Asp Asn Ser Phe
                20                  25                  30

Arg Arg Glu Leu Asp Ala Leu Gly His Glu Leu Pro Val Leu Ala Pro
            35                  40                  45

Gln Trp Glu Gly Tyr Asp Glu Leu Gln Thr Asp Gly Asn Arg Ser Ser
    50                  55                  60

His Ser Arg Leu Gly Arg Ile Glu Ala Asp Ser Gly Ser Gln Glu Asp
65                  70                  75                  80

Ile Ile Arg Asn Ile Ala Arg His Leu Ala Gln Val Gly Asp Ser Met
                85                  90                  95

Asp Arg Ser Ile Pro Pro Gly Leu Val Asn Gly Leu Ala Leu Gln Leu
            100                 105                 110

Arg Asn Thr Ser Arg Ser Glu Glu Asp Arg Asn Arg Asp Leu Ala Thr
        115                 120                 125

Ala Leu Glu Gln Leu Leu Gln Ala Tyr Pro Arg Asp Met Glu Lys Glu
    130                 135                 140

Lys Thr Met Leu Val Leu Ala Leu Leu Leu Ala Lys Lys Val Ala Ser
145                 150                 155                 160

His Thr Pro Ser Leu Leu Arg Asp Val Phe His Thr Thr Val Asn Phe
                165                 170                 175

Ile Asn Gln Asn Leu Arg Thr Tyr Val Arg Ser Leu Ala Arg Asn Gly
            180                 185                 190

Met Asp

<210> SEQ ID NO 22
<211> LENGTH: 197
<212> TYPE: PRT
<213> ORGANISM: Homo sapiens

<400> SEQUENCE: 22

Ala Lys Gln Pro Ser Asp Val Ser Ser Glu Cys Asp Arg Glu Gly Arg
1               5                   10                  15

Gln Leu Gln Pro Ala Glu Arg Pro Pro Gln Leu Arg Pro Gly Ala Pro
                20                  25                  30

Thr Ser Leu Gln Thr Glu Pro Gln Gly Asn Pro Glu Gly Asn His Gly

```
                35                  40                  45
Gly Glu Gly Asp Ser Cys Pro His Gly Ser Pro Gln Gly Pro Leu Ala
 50                  55                  60

Pro Pro Ala Ser Pro Gly Pro Phe Ala Thr Arg Ser Pro Leu Phe Ile
 65                  70                  75                  80

Phe Met Arg Arg Ser Ser Leu Leu Ser Arg Ser Ser Gly Tyr Phe
                 85                  90                  95

Ser Phe Asp Thr Asp Arg Ser Pro Ala Pro Met Ser Cys Asp Lys Ser
                100                 105                 110

Thr Gln Thr Pro Ser Pro Pro Cys Gln Ala Phe Asn His Tyr Leu Ser
            115                 120                 125

Ala Met Ala Ser Met Arg Gln Ala Glu Pro Ala Asp Met Arg Pro Glu
        130                 135                 140

Ile Trp Ile Ala Gln Glu Leu Arg Arg Ile Gly Asp Glu Phe Asn Ala
145                 150                 155                 160

Tyr Tyr Ala Arg Arg Val Phe Leu Asn Asn Tyr Gln Ala Ala Glu Asp
                165                 170                 175

His Pro Arg Met Val Ile Leu Arg Leu Leu Arg Tyr Ile Val Arg Leu
            180                 185                 190

Val Trp Arg Met His
            195

<210> SEQ ID NO 23
<211> LENGTH: 89
<212> TYPE: PRT
<213> ORGANISM: Homo sapiens

<400> SEQUENCE: 23

Cys Pro Cys Pro Leu His Arg Gly Arg Gly Pro Pro Ala Val Cys Ala
 1               5                  10                  15

Cys Ser Ala Gly Arg Leu Gly Leu Arg Ser Ser Ala Ala Gln Leu Thr
                20                  25                  30

Ala Ala Arg Leu Lys Ala Leu Gly Asp Glu Leu His Gln Arg Thr Met
            35                  40                  45

Trp Arg Arg Arg Ala Arg Ser Arg Arg Ala Pro Ala Pro Gly Ala Leu
 50                  55                  60

Pro Thr Tyr Trp Pro Trp Leu Cys Ala Ala Ala Gln Val Ala Ala Leu
 65                  70                  75                  80

Ala Ala Trp Leu Leu Gly Arg Arg Asn
                85

<210> SEQ ID NO 24
<211> LENGTH: 297
<212> TYPE: PRT
<213> ORGANISM: Artificial Sequence
<220> FEATURE:
<223> OTHER INFORMATION: IL-4-Bad fusion

<400> SEQUENCE: 24

Met His Lys Cys Asp Ile Thr Leu Gln Glu Ile Ile Lys Thr Leu Asn
 1               5                  10                  15

Ser Leu Thr Glu Gln Lys Thr Leu Cys Thr Glu Leu Val Thr Asp
                20                  25                  30

Ile Phe Ala Ala Ser Lys Asp Thr Thr Glu Lys Glu Thr Phe Cys Arg
            35                  40                  45

Ala Ala Thr Val Leu Arg Gln Phe Tyr Ser His His Glu Lys Asp Thr
 50                  55                  60
```

Arg Cys Leu Gly Ala Thr Ala Gln Gln Phe His Arg His Lys Gln Leu
65                  70                  75                  80

Ile Arg Phe Leu Lys Arg Leu Asp Arg Asn Leu Trp Gly Leu Ala Gly
                85                  90                  95

Leu Asn Ser Cys Pro Val Lys Glu Ala Asn Gln Ser Thr Leu Glu Asn
            100                 105                 110

Phe Leu Glu Arg Leu Lys Thr Ile Met Arg Glu Lys Tyr Ser Lys Cys
        115                 120                 125

Ser Ser Phe Gln Ile Pro Glu Phe Glu Pro Ser Glu Gln Glu Asp Ser
130                 135                 140

Ser Ser Ala Glu Arg Gly Leu Gly Pro Ser Pro Ala Gly Asp Gly Pro
145                 150                 155                 160

Ser Gly Ser Gly Lys His His Arg Gln Ala Pro Gly Leu Leu Trp Asp
                165                 170                 175

Ala Ser His Gln Gln Glu Gln Pro Thr Ser Ser Ser His His Gly Gly
            180                 185                 190

Ala Gly Ala Val Glu Ile Arg Ser Arg His Ser Ala Tyr Pro Ala Gly
        195                 200                 205

Thr Glu Asp Asp Glu Gly Met Gly Glu Glu Pro Ser Pro Phe Arg Gly
210                 215                 220

Arg Ser Arg Ala Ala Pro Pro Asn Leu Trp Ala Ala Gln Arg Tyr Gly
225                 230                 235                 240

Arg Glu Leu Arg Arg Met Ser Asp Glu Phe Val Asp Ser Phe Lys Lys
                245                 250                 255

Gly Leu Pro Arg Pro Lys Ser Ala Gly Thr Ala Thr Gln Met Arg Gln
            260                 265                 270

Ser Ser Ser Trp Thr Arg Val Phe Gln Ser Trp Trp Asp Arg Asn Leu
        275                 280                 285

Gly Arg Gly Ser Ser Ala Pro Ser Gln
    290                 295

<210> SEQ ID NO 25
<211> LENGTH: 303
<212> TYPE: PRT
<213> ORGANISM: Artificial Sequence
<220> FEATURE:
<223> OTHER INFORMATION: cpIL4-Bad fusion

<400> SEQUENCE: 25

Met Asp Thr Thr Glu Lys Glu Thr Phe Cys Arg Ala Ala Thr Val Leu
1               5                   10                  15

Arg Gln Phe Tyr Ser His His Glu Lys Asp Thr Arg Cys Leu Gly Ala
                20                  25                  30

Thr Ala Gln Gln Phe His Arg His Lys Gln Leu Ile Arg Phe Leu Lys
        35                  40                  45

Arg Leu Asp Arg Asn Leu Trp Gly Leu Ala Gly Leu Asn Ser Cys Pro
    50                  55                  60

Val Lys Glu Ala Asn Gln Ser Thr Leu Glu Asn Phe Leu Glu Arg Leu
65                  70                  75                  80

Lys Thr Ile Met Arg Glu Lys Tyr Ser Lys Cys Ser Ser Gly Gly Asn
                85                  90                  95

Gly Gly His Lys Cys Asp Ile Thr Leu Gln Glu Ile Ile Lys Thr Leu
            100                 105                 110

Asn Ser Leu Thr Glu Gln Lys Thr Leu Cys Thr Glu Leu Thr Val Thr
        115                 120                 125

```
Asp Ile Phe Ala Ala Ser Gly Ser Phe Gln Ile Pro Glu Phe Glu Pro
        130                 135                 140

Ser Glu Gln Glu Asp Ser Ser Ala Glu Arg Gly Leu Gly Pro Ser
145                 150                 155                 160

Pro Ala Gly Asp Gly Pro Ser Gly Ser Gly Lys His His Arg Gln Ala
                165                 170                 175

Pro Gly Leu Leu Trp Asp Ala Ser His Gln Gln Glu Gln Pro Thr Ser
            180                 185                 190

Ser Ser His His Gly Gly Ala Gly Ala Val Glu Ile Arg Ser Arg His
        195                 200                 205

Ser Ala Tyr Pro Ala Gly Thr Glu Asp Asp Glu Gly Met Gly Glu Glu
    210                 215                 220

Pro Ser Pro Phe Arg Gly Arg Ser Arg Ala Ala Pro Pro Asn Leu Trp
225                 230                 235                 240

Ala Ala Gln Arg Tyr Gly Arg Glu Leu Arg Arg Met Ser Asp Glu Phe
                245                 250                 255

Val Asp Ser Phe Lys Lys Gly Leu Pro Arg Pro Lys Ser Ala Gly Thr
            260                 265                 270

Ala Thr Gln Met Arg Gln Ser Ser Ser Trp Thr Arg Val Phe Gln Ser
        275                 280                 285

Trp Trp Asp Arg Asn Leu Gly Arg Gly Ser Ser Ala Pro Ser Gln
    290                 295                 300

<210> SEQ ID NO 26
<211> LENGTH: 303
<212> TYPE: PRT
<213> ORGANISM: Artificial Sequence
<220> FEATURE:
<223> OTHER INFORMATION: cpKFR4-Bad fusion

<400> SEQUENCE: 26

Met Asp Thr Thr Glu Lys Glu Thr Phe Cys Arg Ala Ala Thr Val Leu
1               5                   10                  15

Arg Gln Phe Tyr Ser His His Glu Lys Asp Thr Arg Cys Leu Gly Ala
                20                  25                  30

Thr Ala Gln Gln Phe His Arg His Lys Gln Leu Ile Arg Phe Leu Lys
            35                  40                  45

Arg Leu Asp Arg Asn Leu Trp Gly Leu Ala Gly Leu Asn Ser Cys Pro
50                  55                  60

Val Lys Glu Ala Asn Gln Ser Thr Leu Glu Asn Phe Leu Glu Arg Leu
65                  70                  75                  80

Lys Thr Ile Met Lys Glu Lys Phe Arg Lys Cys Ser Ser Gly Gly Asn
                85                  90                  95

Gly Gly His Lys Cys Asp Ile Thr Leu Gln Glu Ile Ile Lys Thr Leu
            100                 105                 110

Asn Ser Leu Thr Glu Gln Lys Thr Leu Cys Thr Glu Leu Thr Val Thr
        115                 120                 125

Asp Ile Phe Ala Ala Ser Gly Ser Phe Gln Ile Pro Glu Phe Glu Pro
    130                 135                 140

Ser Glu Gln Glu Asp Ser Ser Ala Glu Arg Gly Leu Gly Pro Ser
145                 150                 155                 160

Pro Ala Gly Asp Gly Pro Ser Gly Ser Gly Lys His His Arg Gln Ala
                165                 170                 175

Pro Gly Leu Leu Trp Asp Ala Ser His Gln Gln Glu Gln Pro Thr Ser
            180                 185                 190
```

Ser Ser His His Gly Gly Ala Gly Ala Val Glu Ile Arg Ser Arg His
        195                 200                 205

Ser Ala Tyr Pro Ala Gly Thr Glu Asp Asp Glu Gly Met Gly Glu Glu
    210                 215                 220

Pro Ser Pro Phe Arg Gly Arg Ser Arg Ala Ala Pro Pro Asn Leu Trp
225                 230                 235                 240

Ala Ala Gln Arg Tyr Gly Arg Glu Leu Arg Arg Met Ser Asp Glu Phe
            245                 250                 255

Val Asp Ser Phe Lys Lys Gly Leu Pro Arg Pro Lys Ser Ala Gly Thr
            260                 265                 270

Ala Thr Gln Met Arg Gln Ser Ser Ser Trp Thr Arg Val Phe Gln Ser
            275                 280                 285

Trp Trp Asp Arg Asn Leu Gly Arg Gly Ser Ser Ala Pro Ser Gln
        290                 295                 300

<210> SEQ ID NO 27
<211> LENGTH: 303
<212> TYPE: PRT
<213> ORGANISM: Artificial Sequence
<220> FEATURE:
<223> OTHER INFORMATION: cpS4-Bad fusion

<400> SEQUENCE: 27

Met Asp Thr Thr Glu Lys Glu Thr Phe Cys Arg Ala Ala Thr Val Leu
1               5                   10                  15

Arg Gln Phe Tyr Ser His His Glu Lys Asp Thr Arg Cys Leu Gly Ala
            20                  25                  30

Thr Ala Gln Gln Phe His Arg His Lys Gln Leu Ile Arg Phe Leu Lys
        35                  40                  45

Arg Leu Asp Arg Asn Leu Trp Gly Leu Ala Gly Leu Asn Ser Cys Pro
50                  55                  60

Val Lys Glu Ala Asn Gln Ser Thr Leu Glu Asn Phe Leu Glu Arg Leu
65                  70                  75                  80

Arg Val Ile Met Gln Ser Lys Trp Phe Lys Cys Gly Ala Gly Gly Asn
            85                  90                  95

Gly Gly His Lys Cys Asp Ile Thr Leu Gln Glu Ile Ile Lys Thr Leu
            100                 105                 110

Asn Ser Leu Thr Glu Gln Lys Thr Leu Cys Thr Glu Leu Thr Val Thr
        115                 120                 125

Asp Ile Phe Ala Ala Ser Gly Ser Phe Gln Ile Pro Glu Phe Glu Pro
    130                 135                 140

Ser Glu Gln Glu Asp Ser Ser Ala Glu Arg Gly Leu Gly Pro Ser
145                 150                 155                 160

Pro Ala Gly Asp Gly Pro Ser Gly Ser Gly Lys His His Arg Gln Ala
            165                 170                 175

Pro Gly Leu Leu Trp Asp Ala Ser His Gln Gln Glu Gln Pro Thr Ser
        180                 185                 190

Ser Ser His His Gly Gly Ala Gly Ala Val Glu Ile Arg Ser Arg His
        195                 200                 205

Ser Ala Tyr Pro Ala Gly Thr Glu Asp Asp Glu Gly Met Gly Glu Glu
    210                 215                 220

Pro Ser Pro Phe Arg Gly Arg Ser Arg Ala Ala Pro Pro Asn Leu Trp
225                 230                 235                 240

Ala Ala Gln Arg Tyr Gly Arg Glu Leu Arg Arg Met Ser Asp Glu Phe
            245                 250                 255

Val Asp Ser Phe Lys Lys Gly Leu Pro Arg Pro Lys Ser Ala Gly Thr
            260                 265                 270

Ala Thr Gln Met Arg Gln Ser Ser Trp Thr Arg Val Phe Gln Ser
        275                 280                 285

Trp Trp Asp Arg Asn Leu Gly Arg Gly Ser Ser Ala Pro Ser Gln
        290                 295                 300

<210> SEQ ID NO 28
<211> LENGTH: 82
<212> TYPE: PRT
<213> ORGANISM: Artificial Sequence
<220> FEATURE:
<223> OTHER INFORMATION: ubiquitin linker sequence

<400> SEQUENCE: 28

Gly Gly Gly Ser Met Gln Ile Phe Val Arg Thr Leu Thr Gly Arg Thr
1               5                   10                  15

Ile Thr Leu Glu Val Glu Pro Ser Asp Thr Ile Glu Asn Val Arg Ala
            20                  25                  30

Arg Ile Gln Asp Arg Glu Gly Ile Pro Pro Asp Gln Gln Arg Leu Ile
        35                  40                  45

Phe Ala Gly Arg Gln Leu Glu Asp Gly Arg Thr Leu Ser Asp Tyr Asn
    50                  55                  60

Ile Gln Arg Glu Ser Thr Leu His Leu Val Leu Arg Leu Arg Gly Gly
65                  70                  75                  80

Gly Ser

<210> SEQ ID NO 29
<211> LENGTH: 6
<212> TYPE: PRT
<213> ORGANISM: Artificial Sequence
<220> FEATURE:
<223> OTHER INFORMATION: linker

<400> SEQUENCE: 29

Ala Ser Gly Gly Pro Glu
1               5

<210> SEQ ID NO 30
<211> LENGTH: 390
<212> TYPE: DNA
<213> ORGANISM: Artificial Sequence
<220> FEATURE:
<223> OTHER INFORMATION: IL-4

<400> SEQUENCE: 30
atgcacaaat gcgacattac cctgcaagag atcattaaga ccctgaacag cctgaccgag      60
caaaagaccc tgtgtaccga actgaccgtc acggacatct tcgctgcgtc caaggacact     120
acggaaaagg aaacgttctg tcgtgcggcg acggtgctgc gccagttcta cagccaccat     180
gagaaagata cccgttgcct cggtgcgacc gcgcaacagt tccaccgtca caaacagctg     240
attcgcttcc tgaagcgtct ggatcgcaac ctgtggggtt tggcgggtct gaactcctgt     300
ccagtcaaag aagccaatca gtctacgctg gaaaactttt ggagcgtctc gaaaactatc     360
atgcgtgaga agtacagcaa atgcagcagc                                      390

<210> SEQ ID NO 31
<211> LENGTH: 402
<212> TYPE: DNA
<213> ORGANISM: Artificial Sequence

```
<220> FEATURE:
<223> OTHER INFORMATION: cpIL4

<400> SEQUENCE: 31
atggatacca ccgagaaaga aacgttctgc cgtgctgcca ctgtcctgcg ccagttttac      60
agccatcacg aaaggacac ccgttgcctg ggtgcgacgg cgcagcaatt ccaccgccac     120
aaacagctga ttcgtttcct gaagcgtctg accgtaacc tgtggggtct ggcgggtctg     180
aacagctgtc cagtgaaaga agcgaatcag agcaccttgg agaatttcct cgaacgcctg    240
aaaaccatca tgcgtgagaa atacagcaag tgttctagcg gcggtaacgg tggccacaaa    300
tgcgatatca ccctgcaaga gatcattaag acgctgaact ccttgacgga acaaaagacc    360
ctgtgtactg agctgacggt caccgacatt ttcgcggcgt cc                       402

<210> SEQ ID NO 32
<211> LENGTH: 402
<212> TYPE: DNA
<213> ORGANISM: Artificial Sequence
<220> FEATURE:
<223> OTHER INFORMATION: cpKFR

<400> SEQUENCE: 32
atggatacta ccgagaaaga aacgttttgc cgtgctgcga ccgtcctgcg tcagttctac      60
agccaccacg aaaggacac ccgctgtctg ggtgcgactg cccaacaatt ccatcgtcac     120
aaacagctga ttcgtttcct gaagcgtctg accgcaacc tgtggggtct ggcgggcttg     180
aactcctgcc cagtcaaaga agcgaaccaa agcaccctgg aaaacttctt ggagcgtctg    240
aaaacgatca tgaaagagaa gttccgcaag tgtagcagcg gtggtaatgg tggccacaag    300
tgcgacatta cgctgcagga aatcattaag accctgaact ctctgaccga gcagaaaacc    360
ctctgtaccg agctgacggt gacggatatc tttgcggcga gc                       402

<210> SEQ ID NO 33
<211> LENGTH: 402
<212> TYPE: DNA
<213> ORGANISM: Artificial Sequence
<220> FEATURE:
<223> OTHER INFORMATION: cpS4

<400> SEQUENCE: 33
atggatacca ccgaaaaaga aactttttgt cgtgccgcga ctgtcctgcg ccagttctac      60
agccaccacg aaaggacac ccgttgcctg ggtgcgaccg ctcaacaatt ccatcgccac     120
aaacagctga ttcgtttcct gaaacgtctg gatcgcaacc tgtggggtct ggcgggtttg    180
aacagctgtc cagtcaaaga agcgaaccag agcaccctgg aaaacttcct ggagcgtctg    240
cgtgttatca tgcagagcaa gtggttcaag tgcggtgcgg gtggcaatgg tggccacaag    300
tgtgacatta ccttgcaaga gattatcaaa acgctgaact ctctgaccga gcaaaagacg    360
ctgtgcaccg agctgacggt gacggacatc ttcgcggcgt cc                       402

<210> SEQ ID NO 34
<211> LENGTH: 507
<212> TYPE: DNA
<213> ORGANISM: Artificial Sequence
<220> FEATURE:
<223> OTHER INFORMATION: pro-apoptotic Bcl-2 family member nucleic acid
      molecule, variant BAD

<400> SEQUENCE: 34
ggtagctttc agatcccgga atttgagccg agcgagcaag aggattcaag cagcgcggag     60
```

| | | |
|---|---|---|
| cgcggtctgg gtccgagccc ggcaggcgac ggtccgagcg gcagcggcaa gcatcaccgc | 120 |
| caggcgccag gcctgctgtg ggatgcatcg catcaacagg aacaaccgac gagcagcagc | 180 |
| catcatggtg gcgctggtgc ggttgagatt agatcgcgcc actccgcata tcctgccggc | 240 |
| accgaagatg acgaaggcat gggcgaggaa ccgagcccgt tccgtggccg tagccgtgct | 300 |
| gcaccgccga atctgtgggc cgcacagcgt tatggtcgcg agttgcgtcg catgtccgac | 360 |
| gagtttgttg actccttcaa gaaaggttta ccgcgtccga atctgccgg taccgcgacg | 420 |
| cagatgcgtc agagcagcag ctggacccgc gtgtttcaat cttggtggga tcgtaatctg | 480 |
| ggtcgtggta gcagcgcacc gagccaa | 507 |

<210> SEQ ID NO 35
<211> LENGTH: 897
<212> TYPE: DNA
<213> ORGANISM: Artificial Sequence
<220> FEATURE:
<223> OTHER INFORMATION: IL-4-Bad fusion

<400> SEQUENCE: 35

| | | |
|---|---|---|
| atgcacaaat gcgacattac cctgcaagag atcattaaga ccctgaacag cctgaccgag | 60 |
| caaaagaccc tgtgtaccga actgaccgtc acggacatct cgctgcgtc caaggacact | 120 |
| acggaaaagg aaacgttctg tcgtgcggcg acggtgctgc gccagttcta cagccaccat | 180 |
| gagaaagata cccgttgcct cggtgcgacc cgcaacagt tccaccgtca caaacagctg | 240 |
| attcgcttcc tgaagcgtct ggatcgcaac ctgtggggtt tggcgggtct gaactcctgt | 300 |
| ccagtcaaag aagccaatca gtctacgctg gaaaacttt tggagcgtct gaaaactatc | 360 |
| atgcgtgaga gtacagcaa tgcagcagc ggtagcttc agatcccgga atttgagccg | 420 |
| agcgagcaag aggattcaag cagcgcggag cgcggtctgg gtccgagccc ggcaggcgac | 480 |
| ggtccgagcg gcagcggcaa gcatcaccgc caggcgccag gcctgctgtg ggatgcatcg | 540 |
| catcaacagg aacaaccgac gagcagcagc catcatggtg gcgctggtgc ggttgagatt | 600 |
| agatcgcgcc actccgcata tcctgccggc accgaagatg acgaaggcat gggcgaggaa | 660 |
| ccgagcccgt tccgtggccg tagccgtgct gcaccgccga atctgtgggc cgcacagcgt | 720 |
| tatggtcgcg agttgcgtcg catgtccgac gagtttgttg actccttcaa gaaaggttta | 780 |
| ccgcgtccga atctgccgg taccgcgacg cagatgcgtc agagcagcag ctggacccgc | 840 |
| gtgtttcaat cttggtggga tcgtaatctg ggtcgtggta gcagcgcacc gagccaa | 897 |

<210> SEQ ID NO 36
<211> LENGTH: 909
<212> TYPE: DNA
<213> ORGANISM: Artificial Sequence
<220> FEATURE:
<223> OTHER INFORMATION: cpIL4-Bad fusion

<400> SEQUENCE: 36

| | | |
|---|---|---|
| atggatacca ccgagaaaga aacgttctgc cgtgctgcca ctgtcctgcg ccagttttac | 60 |
| agccatcacg aaaaggacac ccgttgcctg ggtgcgacgg cgcagcaatt ccaccgccac | 120 |
| aaacagctga ttcgtttcct gaagcgtctg accgtaacc tgtggggtct ggcgggtctg | 180 |
| aacagctgtc cagtgaaaga agcgaatcag agcaccttgg agaatttcct cgaacgcctg | 240 |
| aaaaccatca tgcgtgagaa atacagcaag tgttctagcg gcggtaacgg tggccacaaa | 300 |
| tgcgatatca ccctgcaaga gatcattaag acgctgaact ccttgacgga acaaaagacc | 360 |

| | |
|---|---|
| ctgtgtactg agctgacggt caccgacatt ttcgcggcgt ccggtagctt tcagatcccg | 420 |
| gaatttgagc cgagcgagca agaggattca agcagcgcgg agcgcggtct gggtccgagc | 480 |
| ccggcaggcg acggtccgag cggcagcggc aagcatcacc gccaggcgcc aggcctgctg | 540 |
| tgggatgcat cgcatcaaca ggaacaaccg acgagcagca gccatcatgg tggcgctggt | 600 |
| gcggttgaga ttagatcgcg ccactccgca tatcctgccg gcaccgaaga tgacgaaggc | 660 |
| atgggcgagg aaccgagccc gttccgtggc cgtagccgtg ctgcaccgcc gaatctgtgg | 720 |
| gccgcacagc gttatggtcg cgagttgcgt cgcatgtccg acgagtttgt tgactccttc | 780 |
| aagaaaggtt taccgcgtcc gaaatctgcc ggtaccgcga cgcagatgcg tcagagcagc | 840 |
| agctggaccc gcgtgtttca atcttggtgg gatcgtaatc tgggtcgtgg tagcagcgca | 900 |
| ccgagccaa | 909 |

<210> SEQ ID NO 37
<211> LENGTH: 909
<212> TYPE: DNA
<213> ORGANISM: Artificial Sequence
<220> FEATURE:
<223> OTHER INFORMATION: cpKFR4-Bad fusion

<400> SEQUENCE: 37

| | |
|---|---|
| atggatacta ccgagaaaga aacgttttgc cgtgctgcga ccgtcctgcg tcagttctac | 60 |
| agccaccacg aaaaggacac ccgctgtctg ggtgcgactg cccaacaatt ccatcgtcac | 120 |
| aaacagctga ttcgtttcct gaagcgtctg gaccgcaacc tgtggggtct ggcgggcttg | 180 |
| aactcctgcc cagtcaaaga agcgaaccaa agcaccctgg aaaacttctt ggagcgtctg | 240 |
| aaaacgatca tgaaagagaa gttccgcaag tgtagcagcg gtggtaatgg tggccacaag | 300 |
| tgcgacatta cgctgcagga aatcattaag accctgaact ctctgaccga gcagaaaacc | 360 |
| ctctgtaccg agctgacggt gacggatatc tttgcggcga gcggtagctt tcagatcccg | 420 |
| gaatttgagc cgagcgagca agaggattca agcagcgcgg agcgcggtct gggtccgagc | 480 |
| ccggcaggcg acggtccgag cggcagcggc aagcatcacc gccaggcgcc aggcctgctg | 540 |
| tgggatgcat cgcatcaaca ggaacaaccg acgagcagca gccatcatgg tggcgctggt | 600 |
| gcggttgaga ttagatcgcg ccactccgca tatcctgccg gcaccgaaga tgacgaaggc | 660 |
| atgggcgagg aaccgagccc gttccgtggc cgtagccgtg ctgcaccgcc gaatctgtgg | 720 |
| gccgcacagc gttatggtcg cgagttgcgt cgcatgtccg acgagtttgt tgactccttc | 780 |
| aagaaaggtt taccgcgtcc gaaatctgcc ggtaccgcga cgcagatgcg tcagagcagc | 840 |
| agctggaccc gcgtgtttca atcttggtgg gatcgtaatc tgggtcgtgg tagcagcgca | 900 |
| ccgagccaa | 909 |

<210> SEQ ID NO 38
<211> LENGTH: 909
<212> TYPE: DNA
<213> ORGANISM: Artificial Sequence
<220> FEATURE:
<223> OTHER INFORMATION: cpS4-Bad fusion

<400> SEQUENCE: 38

| | |
|---|---|
| atggatacca ccgaaaaaga aactttttgt cgtgccgcga ctgtcctgcg ccagttctac | 60 |
| agccaccacg aaaaggacac ccgttgcctg ggtgcgaccg ctcaacaatt ccatcgccac | 120 |
| aaacagctga ttcgtttcct gaaacgtctg gatcgcaacc tgtggggtct ggcgggtttg | 180 |
| aacagctgtc cagtcaaaga agcgaaccag agcaccctgg aaaactttct ggagcgtctg | 240 |

```
cgtgttatca tgcagagcaa gtggttcaag tgcggtgcgg gtggcaatgg tggccacaag    300
tgtgacatta ccttgcaaga gattatcaaa acgctgaact ctctgaccga gcaaaagacg    360
ctgtgcaccg agctgacggt gacggacatc ttcgcggcgt ccggtagctt cagatcccg     420 gaatttgagc cgagcgagca agaggattca agcagcgcgg agcgcggtct gggtccgagc    480
ccggcaggcg acgtccgag cggcagcggc aagcatcacc gccaggcgcc aggcctgctg     540
tgggatgcat cgcatcaaca ggaacaaccg acgagcagca gccatcatgg tggcgctggt    600
gcggttgaga ttagatcgcg ccactccgca tatcctgccg gcaccgaaga tgacgaaggc    660
atgggcgagg aaccgagccc gttccgtggc cgtagccgtg ctgcaccgcc gaatctgtgg    720
gccgcacagc gttatggtcg cgagttgcgt cgcatgtccg acgagtttgt tgactccttc    780
aagaaaggtt taccgcgtcc gaaatctgcc ggtaccgcga cgcagatgcg tcagagcagc    840
agctggaccc gcgtgtttca atcttggtgg gatcgtaatc tgggtcgtgg tagcagcgca    900
ccgagccaa                                                            909
```

```
<210> SEQ ID NO 39
<211> LENGTH: 918
<212> TYPE: DNA
<213> ORGANISM: Artificial Sequence
<220> FEATURE:
<223> OTHER INFORMATION: cpIL-4-Bad

<400> SEQUENCE: 39
atgcacaaat gcgacattac cctgcaagag atcattaaga ccctgaacag cctgaccgag    60
caaaagaccc tgtgtaccga actgaccgtc acggacatct cgctgcgtc caaggacact     120 acggaaaagg aaacgttctg tcgtgcggcg acggtgctgc gccagttcta cagccaccat    180
gagaaagata cccgttgcct cggtgcgacc gcgcaacagt tccaccgtca caaacagctg    240
attcgcttcc tgaagcgtct ggatcgcaac ctgtggggtt tggcgggtct gaactcctgt    300
ccagtcaaag aagccaatca gtctacgctg gaaaactttt tggagcgtct gaaaactatc    360
atgcgtgaga agtacagcaa atgcagcagc ggtagctttc agatcccgga atttgagccg    420
agcgagcaag aggattcaag cagcgcggag cgcggtctgg gtccgagccc ggcaggcgac    480
ggtccgagcg gcagcggcaa gcatcaccgc caggcgccag gcctgctgtg ggatgcatcg    540
catcaacagg aacaaccgac gagcagcagc catcatggtg gcgctggtgc ggttgagatt    600
agatcgcgcc actccgcata tcctgccggc accgaagatg acgaaggcat gggcgaggaa    660
ccgagcccgt tccgtggccg tagccgtgct gcaccgccga atctgtgggc cgcacagcgt    720
tatggtcgcg agttgcgtcg catgtccgac gagtttgttg actccttcaa gaaaggttta    780
ccgcgtccga aatctgccgg taccgcgacg cagatgcgtc agagcagcag ctggacccgc    840
gtgtttcaat cttggtggga tcgtaatctg ggtcgtggta gcagcgcacc gagccaacac    900
caccatcacc atcactaa                                                  918
```

```
<210> SEQ ID NO 40
<211> LENGTH: 305
<212> TYPE: PRT
<213> ORGANISM: Artificial Sequence
<220> FEATURE:
<223> OTHER INFORMATION: IL-4-Bad

<400> SEQUENCE: 40

Met His Lys Cys Asp Ile Thr Leu Gln Glu Ile Ile Lys Thr Leu Asn
1               5                   10                  15
```

```
Ser Leu Thr Glu Gln Lys Thr Leu Cys Thr Glu Leu Thr Val Thr Asp
         20                  25                  30

Ile Phe Ala Ala Ser Lys Asp Thr Glu Lys Glu Thr Phe Cys Arg
         35                  40                  45

Ala Ala Thr Val Leu Arg Gln Phe Tyr Ser His His Glu Lys Asp Thr
 50                  55                  60

Arg Cys Leu Gly Ala Thr Ala Gln Gln Phe His Arg His Lys Gln Leu
 65                  70                  75                  80

Ile Arg Phe Leu Lys Arg Leu Asp Arg Asn Leu Trp Gly Leu Ala Gly
                 85                  90                  95

Leu Asn Ser Cys Pro Val Lys Glu Ala Asn Gln Ser Thr Leu Glu Asn
            100                 105                 110

Phe Leu Glu Arg Leu Lys Thr Ile Met Arg Glu Lys Tyr Ser Lys Cys
        115                 120                 125

Ser Ser Gly Ser Phe Gln Ile Pro Glu Phe Glu Pro Ser Glu Gln Glu
    130                 135                 140

Asp Ser Ser Ser Ala Glu Arg Gly Leu Gly Pro Ser Pro Ala Gly Asp
145                 150                 155                 160

Gly Pro Ser Gly Ser Gly Lys His His Arg Gln Ala Pro Gly Leu Leu
                165                 170                 175

Trp Asp Ala Ser His Gln Gln Glu Gln Pro Thr Ser Ser Ser His His
            180                 185                 190

Gly Gly Ala Gly Ala Val Glu Ile Arg Ser Arg His Ser Ala Tyr Pro
        195                 200                 205

Ala Gly Thr Glu Asp Asp Glu Gly Met Gly Glu Glu Pro Ser Pro Phe
    210                 215                 220

Arg Gly Arg Ser Arg Ala Ala Pro Pro Asn Leu Trp Ala Ala Gln Arg
225                 230                 235                 240

Tyr Gly Arg Glu Leu Arg Arg Met Ser Asp Glu Phe Val Asp Ser Phe
                245                 250                 255

Lys Lys Gly Leu Pro Arg Pro Lys Ser Ala Gly Thr Ala Thr Gln Met
            260                 265                 270

Arg Gln Ser Ser Ser Trp Thr Arg Val Phe Gln Ser Trp Trp Asp Arg
        275                 280                 285

Asn Leu Gly Arg Gly Ser Ser Ala Pro Ser Gln His His His His His
    290                 295                 300

His
305

<210> SEQ ID NO 41
<211> LENGTH: 927
<212> TYPE: DNA
<213> ORGANISM: Artificial Sequence
<220> FEATURE:
<223> OTHER INFORMATION: bp cpIL-4-Bad

<400> SEQUENCE: 41
atggatacca ccgagaaaga aacgttctgc cgtgctgcca ctgtcctgcg ccagttttac      60
agccatcacg aaaaggacac ccgttgcctg ggtgcgacgg cgcagcaatt ccaccgccac     120
aaacagctga ttcgtttcct gaagcgtctg accgtaacc tgtggggtct ggcgggtctg     180
aacagctgtc cagtgaaaga agcgaatcag agcaccttgg agaatttcct cgaacgcctg     240
aaaaccatca tgcgtgagaa atacagcaag tgttctagcg gcgttaacgg tggccacaaa     300
tgcgatatca ccctgcaaga gatcattaag acgctgaact ccttgacgga acaaaagacc     360
```

```
ctgtgtactg agctgacggt caccgacatt ttcgcggcgt ccggtagctt tcagatcccg    420
gaatttgagc cgagcgagca agaggattca agcagcgcgg agcgcggtct gggtccgagc    480
ccggcaggcg acggtccgag cggcagcggc aagcatcacc gccaggcgcc aggcctgctg    540
tgggatgcat cgcatcaaca ggaacaaccg acgagcagca gccatcatgg tggcgctggt    600
gcggttgaga ttagatcgcg ccactccgca tatcctgccg gcaccgaaga tgacgaaggc    660
atgggcgagg aaccgagccc gttccgtggc cgtagccgtg ctgcaccgcc gaatctgtgg    720
gccgcacagc gttatggtcg cgagttgcgt cgcatgtccg acgagtttgt tgactccttc    780
aagaaaggtt taccgcgtcc gaaatctgcc ggtaccgcga cgcagatgcg tcagagcagc    840
agctggaccc gcgtgtttca atcttggtgg gatcgtaatc tgggtcgtgg tagcagcgca    900
ccgagccaac accaccatca ccatcac                                        927
```

<210> SEQ ID NO 42
<211> LENGTH: 309
<212> TYPE: PRT
<213> ORGANISM: Artificial Sequence
<220> FEATURE:
<223> OTHER INFORMATION: cpIL-4-Bad

<400> SEQUENCE: 42

Met Asp Thr Thr Glu Lys Glu Thr Phe Cys Arg Ala Ala Thr Val Leu
1               5                   10                  15

Arg Gln Phe Tyr Ser His His Glu Lys Asp Thr Arg Cys Leu Gly Ala
                20                  25                  30

Thr Ala Gln Gln Phe His Arg His Lys Gln Leu Ile Arg Phe Leu Lys
            35                  40                  45

Arg Leu Asp Arg Asn Leu Trp Gly Leu Ala Gly Leu Asn Ser Cys Pro
        50                  55                  60

Val Lys Glu Ala Asn Gln Ser Thr Leu Glu Asn Phe Leu Glu Arg Leu
65                  70                  75                  80

Lys Thr Ile Met Arg Glu Lys Tyr Ser Lys Cys Ser Ser Gly Gly Asn
                85                  90                  95

Gly Gly His Lys Cys Asp Ile Thr Leu Gln Glu Ile Ile Lys Thr Leu
                100                 105                 110

Asn Ser Leu Thr Glu Gln Lys Thr Leu Cys Thr Glu Leu Thr Val Thr
            115                 120                 125

Asp Ile Phe Ala Ala Ser Gly Ser Phe Gln Ile Pro Glu Phe Glu Pro
        130                 135                 140

Ser Glu Gln Glu Asp Ser Ser Ala Glu Arg Gly Leu Gly Pro Ser
145                 150                 155                 160

Pro Ala Gly Asp Gly Pro Ser Gly Ser Gly Lys His His Arg Gln Ala
                165                 170                 175

Pro Gly Leu Leu Trp Asp Ala Ser His Gln Gln Glu Gln Pro Thr Ser
            180                 185                 190

Ser Ser His His Gly Gly Ala Gly Ala Val Glu Ile Arg Ser Arg His
        195                 200                 205

Ser Ala Tyr Pro Ala Gly Thr Glu Asp Asp Glu Gly Met Gly Glu Glu
    210                 215                 220

Pro Ser Pro Phe Arg Gly Arg Ser Arg Ala Ala Pro Pro Asn Leu Trp
225                 230                 235                 240

Ala Ala Gln Arg Tyr Gly Arg Glu Leu Arg Arg Met Ser Asp Glu Phe
                245                 250                 255

Val Asp Ser Phe Lys Lys Gly Leu Pro Arg Pro Lys Ser Ala Gly Thr
            260                 265                 270

Ala Thr Gln Met Arg Gln Ser Ser Trp Thr Arg Val Phe Gln Ser
        275                 280                 285

Trp Trp Asp Arg Asn Leu Gly Arg Gly Ser Ser Ala Pro Ser Gln His
    290                 295                 300

His His His His His
305

<210> SEQ ID NO 43
<211> LENGTH: 930
<212> TYPE: DNA
<213> ORGANISM: Artificial Sequence
<220> FEATURE:
<223> OTHER INFORMATION: bp cpS4-Bad

<400> SEQUENCE: 43
atggatacca ccgaaaaaga aacttttttgt cgtgccgcga ctgtcctgcg ccagttctac      60
agccaccacg aaaaggacac ccgttgcctg ggtgcgaccc tcaacaatt ccatcgccac      120
aaacagctga ttcgtttcct gaaacgtctg gatcgcaacc tgtggggtct ggcgggtttg      180
aacagctgtc cagtcaaaga agcgaaccag agcaccctgg aaaactttct ggagcgtctg      240
cgtgttatca tgcagagcaa gtggttcaag tgcggtgcgg gtggcaatgg tggccacaag      300
tgtgacatta ccttgcaaga gattatcaaa acgctgaact ctctgaccga gcaaaagacg      360
ctgtgcaccg agctgacggt gacggacatc ttcgcggcgt ccggtagctt tcagatcccg      420
gaatttgagc cgagcgagca agaggattca agcagcgcgg agcgcggtct gggtccgagc      480
ccggcaggcg acggtccgag cggcagcggc aagcatcacc gccaggcgcc aggcctgctg      540
tgggatgcat cgcatcaaca ggaacaaccg acgagcagca gccatcatgg tggcgctggt      600
gcggttgaga ttagatcgcg ccactccgca tatcctgccg gcaccgaaga tgacgaaggc      660
atgggcgagg aaccgagccc gttccgtggc cgtagccgtg ctgcaccgcc gaatctgtgg      720
gccgcacagc gttatggtcg cgagttgcgt cgcatgtccg acgagtttgt tgactccttc      780
aagaaaggtt taccgcgtcc gaaatctgcc ggtaccgcga cgcagatgcg tcagagcagc      840
agctggaccc gcgtgtttca atcttggtgg gatcgtaatc tgggtcgtgg tagcagcgca      900
ccgagccaac accaccatca ccatcactaa                                       930

<210> SEQ ID NO 44
<211> LENGTH: 309
<212> TYPE: PRT
<213> ORGANISM: Artificial Sequence
<220> FEATURE:
<223> OTHER INFORMATION: cpS4-Bad

<400> SEQUENCE: 44

Met Asp Thr Thr Glu Lys Glu Thr Phe Cys Arg Ala Ala Thr Val Leu
1               5                   10                  15

Arg Gln Phe Tyr Ser His His Glu Lys Asp Thr Arg Cys Leu Gly Ala
            20                  25                  30

Thr Ala Gln Gln Phe His Arg His Lys Gln Leu Ile Arg Phe Leu Lys
        35                  40                  45

Arg Leu Asp Arg Asn Leu Trp Gly Leu Ala Gly Leu Asn Ser Cys Pro
    50                  55                  60

Val Lys Glu Ala Asn Gln Ser Thr Leu Glu Asn Phe Leu Glu Arg Leu
65                  70                  75                  80

```
Arg Val Ile Met Gln Ser Lys Trp Phe Lys Cys Gly Ala Gly Gly Asn
                 85                  90                  95

Gly Gly His Lys Cys Asp Ile Thr Leu Gln Glu Ile Ile Lys Thr Leu
            100                 105                 110

Asn Ser Leu Thr Glu Gln Lys Thr Leu Cys Thr Glu Leu Thr Val Thr
        115                 120                 125

Asp Ile Phe Ala Ala Ser Gly Ser Phe Gln Ile Pro Glu Phe Glu Pro
    130                 135                 140

Ser Glu Gln Glu Asp Ser Ser Ala Glu Arg Gly Leu Gly Pro Ser
145                 150                 155                 160

Pro Ala Gly Asp Gly Pro Ser Gly Ser Gly Lys His His Arg Gln Ala
                165                 170                 175

Pro Gly Leu Leu Trp Asp Ala Ser His Gln Gln Glu Gln Pro Thr Ser
            180                 185                 190

Ser Ser His His Gly Gly Ala Gly Ala Val Glu Ile Arg Ser Arg His
        195                 200                 205

Ser Ala Tyr Pro Ala Gly Thr Glu Asp Asp Glu Gly Met Gly Glu Glu
    210                 215                 220

Pro Ser Pro Phe Arg Gly Arg Ser Arg Ala Ala Pro Pro Asn Leu Trp
225                 230                 235                 240

Ala Ala Gln Arg Tyr Gly Arg Glu Leu Arg Arg Met Ser Asp Glu Phe
                245                 250                 255

Val Asp Ser Phe Lys Lys Gly Leu Pro Arg Pro Lys Ser Ala Gly Thr
            260                 265                 270

Ala Thr Gln Met Arg Gln Ser Ser Ser Trp Thr Arg Val Phe Gln Ser
        275                 280                 285

Trp Trp Asp Arg Asn Leu Gly Arg Gly Ser Ser Ala Pro Ser Gln His
    290                 295                 300

His His His His
305

<210> SEQ ID NO 45
<211> LENGTH: 926
<212> TYPE: DNA
<213> ORGANISM: Artificial Sequence
<220> FEATURE:
<223> OTHER INFORMATION: bp pKFR4-Bad-H6

<400> SEQUENCE: 45
atggatacta ccgagaaaga aacgttttgc cgtgctgcga ccgtcctgcg tcagttctac     60
agccaccacg aaaggacac ccgctgtctg ggtgcgactg cccaacaatt ccatcgtcac    120
aaacagctga ttcgtttcct gaagcgtctg gaccgcaacc tgtggggtct ggcgggcttg    180
aactcctgcc cagtcaaaga gcgaaccaa agcaccctgg aaaacttctt ggagcgtctg    240
aaaacgatca tgaaagagaa gttccgcaag tgtagcagcg gtggtaatgg tggccacaag    300
tgcgacatta cgctgcagga aatcattaag accctgaact ctctgaccga gcagaaaacc    360
ctctgtaccg agctgacggt gacggatatc tttgcggcga gcggtagctt tcagatcccg    420
gaatttgagc cgagcgagca agaggattca agcagcgcgg agcgcggtct gggtccgagc    480
ccggcaggcg acggtccgag cggcagcggc aagcatcacc gccaggcgcc aggcctgctg    540
tgggatgcat cgcatcaaca ggaacaaccg acgagcagca gccatcatgg tggcgctggt    600
gcggttgaga ttagatcgcg ccactccgca tatcctgccg gcaccgaaga tgacgaaggc    660
atgggcgagg aaccgagccc gttccgtggc cgtagccgtg ctgcaccgcc gaatctgtgg    720
```

```
gccgcacagc gttatggtcg cgagttgcgt cgcatgtccg acgagtttgt tgactccttc    780
aagaaaggtt taccgcgtcc gaaatctgcc ggtaccgcga cgcagatgcg tcagagcagc    840
agctggaccc gcgtgtttca atcttggtgg gatcgtaatc tgggtcgtgg tagcagcgca    900
ccgagccaac accaccatca ccatca                                         926
```

<210> SEQ ID NO 46  
<211> LENGTH: 309  
<212> TYPE: PRT  
<213> ORGANISM: Artificial Sequence  
<220> FEATURE:  
<223> OTHER INFORMATION: pKFR4-Bad-H6

<400> SEQUENCE: 46

```
Met Asp Thr Thr Glu Lys Glu Thr Phe Cys Arg Ala Ala Thr Val Leu
1               5                   10                  15

Arg Gln Phe Tyr Ser His His Glu Lys Asp Thr Arg Cys Leu Gly Ala
            20                  25                  30

Thr Ala Gln Gln Phe His Arg His Lys Gln Leu Ile Arg Phe Leu Lys
        35                  40                  45

Arg Leu Asp Arg Asn Leu Trp Gly Leu Ala Gly Leu Asn Ser Cys Pro
50                  55                  60

Val Lys Glu Ala Asn Gln Ser Thr Leu Glu Asn Phe Leu Glu Arg Leu
65                  70                  75                  80

Lys Thr Ile Met Lys Glu Lys Phe Arg Lys Cys Ser Ser Gly Gly Asn
                85                  90                  95

Gly Gly His Lys Cys Asp Ile Thr Leu Gln Glu Ile Ile Lys Thr Leu
            100                 105                 110

Asn Ser Leu Thr Glu Gln Lys Thr Leu Cys Thr Glu Leu Thr Val Thr
        115                 120                 125

Asp Ile Phe Ala Ala Ser Gly Ser Phe Gln Ile Pro Glu Phe Glu Pro
130                 135                 140

Ser Glu Gln Glu Asp Ser Ser Ala Glu Arg Gly Leu Gly Pro Ser
145                 150                 155                 160

Pro Ala Gly Asp Gly Pro Ser Gly Ser Gly Lys His His Arg Gln Ala
                165                 170                 175

Pro Gly Leu Leu Trp Asp Ala Ser His Gln Gln Glu Gln Pro Thr Ser
            180                 185                 190

Ser Ser His His Gly Gly Ala Gly Ala Val Glu Ile Arg Ser Arg His
        195                 200                 205

Ser Ala Tyr Pro Ala Gly Thr Glu Asp Asp Glu Gly Met Gly Glu Glu
210                 215                 220

Pro Ser Pro Phe Arg Gly Arg Ser Arg Ala Ala Pro Pro Asn Leu Trp
225                 230                 235                 240

Ala Ala Gln Arg Tyr Gly Arg Glu Leu Arg Arg Met Ser Asp Glu Phe
                245                 250                 255

Val Asp Ser Phe Lys Lys Gly Leu Pro Arg Pro Lys Ser Ala Gly Thr
            260                 265                 270

Ala Thr Gln Met Arg Gln Ser Ser Ser Trp Thr Arg Val Phe Gln Ser
        275                 280                 285

Trp Trp Asp Arg Asn Leu Gly Arg Gly Ser Ser Ala Pro Ser Gln His
290                 295                 300

His His His His
305
```

INTERLEUKIN-4 RECEPTOR-BINDING FUSION PROTEINS AND USES THEREOF

CROSS-REFERENCE TO RELATED APPLICATIONS

This application is the U.S. National Phase of International Application No. PCT/CA2014/050915, filed Sep. 24, 2014, which claims the benefit of U.S. Provisional Application No. 61/881,930, filed Sep. 24, 2013, the references of which are hereby incorporated by reference in their entirety.

REFERENCE TO A "SEQUENCE LISTING," A TABLE, OR A COMPUTER PROGRAM, LISTING APPENDIX SUBMITTED ON A COMPACT DISK

This invention incorporated by reference the Sequence Listing text copy submitted herewith, which was created on Apr. 25, 2018, entitled 117802_5002 US_Updated_Sequence.txt which is 68 kilobytes in size.

FIELD OF INVENTION

The present invention relates to interleukin-4 receptor-binding protein fusions. More specifically, the invention provides, in part, fusion proteins that include an interleukin-4 or interleukin-13 protein moiety joined to a pro-apoptotic Bcl-2 family member protein moiety.

BACKGROUND OF THE INVENTION

Interleukin-4 (IL-4) is a pleiotropic cytokine produced by activated T cells, and is the ligand for the IL-4 receptor (IL-4R), which can also bind to interleukin-13 (IL-13). IL-4, like many cytokines, first binds to a high-affinity receptor chain (designated "α"), followed by binding of the IL-4-α chain complex with a second low-affinity receptor chain designated "γc". Therefore, the primary binding chain for IL-4 is the IL-4 receptor alpha (IL-4Rα), which binds with high affinity ($K_D$=~$10^{-10}$ M). The IL-4/IL-4Rα complex can then bind the second component of the IL-4 receptor, γc (the "Type I" receptor) with relatively low affinity. Additionally, the IL-4/IL-4Rα complex can also bind the interleukin-13 (IL-13) receptor α1 (IL-13R α1) (the "Type II" receptor).

Different cell types express different amounts of the Type I and Type II receptor chains. For example, while IL-4Rα is present on most cells, γc is generally expressed on hematopoietic cells and IL-13R α1 is generally expressed on non-hematopoietic cells. Accordingly, γc, but not IL-13R α1, is found on T cells, natural killer (NK) cells, basophils, mast cells, and most mouse B cells (most human B cells express both γc and IL-13R α1).

Some bone marrow-derived cells, including macrophages and dendritic cells, express both γc and IL-13R α1 and consequently respond to both IL-4 and IL-13. IL-13R al, but little or no γc, is found on most non-bone marrow-derived cells, including smooth muscle and epithelial cells.

Variant IL-4 molecules having differential selectivities for Type I and Type II receptors have been proposed (Junttila et al. Nature Chemical Biology 8:990-998, 2012.)

Circularly permuted molecules are those in which the termini of a linear molecule (e.g., ligand) have been joined together, either directly or via a linker, to produce a circular molecule, after which the circular molecule is opened at another location to produce a new linear molecule with termini different from the termini of the original molecule.

Circularly permuted variants of IL-4 have been described in, for example, U.S. Pat. No. 6,011,002, issued Jan. 4, 2000, to Pastan et al.

Programmed cell death or "apoptosis," is a common phenomenon in the development of animal cells and is both positively and negatively regulated. In addition to its involvement in neuronal and lymphoid system development and overall cell population homeostasis, apoptosis also plays a significant role in various diseases and injuries resulting from aberrant regulation of apoptotic pathways. For example, aberrant activation of neuronal cell death by apoptosis has been implicated in many neurodegenerative diseases and conditions, such as Alzheimer disease (Barinaga, Science 281:1303-1304), Huntington's disease, spinal-muscular atrophy, neuronal damage caused during stroke (reviewed in Rubin, British Med. Bulle., 53(3):617-631, 1997; and Barinaga, Science 281:1302-1303), transient ischemic neuronal injury (e.g., spinal cord injury), etc. Conversely, aberrant suppression of apoptosis can result in hyperproliferation of cells, leading to cancer and other hyperproliferative disorders.

Apoptosis is regulated by a number of proteins, including members of the Bcl-2 family. Bcl-2 was one of the first proteins identified as regulating apoptosis (Cleary et al., Cell 47:19-28, 1986; Tsujimoto and Croce, Proc. Natl. Acad. Sci. USA 83:5214-5218, 1986). Since its discovery, several Bcl-2-related proteins ("Bcl-2 family proteins" or "Bcl-2 family members") have been identified as regulators of apoptosis (White, Genes Dev. 10:1-15, 1996; Yang et al., Cell 80:285-291, 1995; Lomonosova, E. and G. Chinnadurai, *Oncogene* 27, S2-S19, 2009).

Several therapeutic agents for treatment of neurodegenerative diseases, cancer, etc. have been explored but exhibit limitations that restrict their use in the clinic. For example, many chemotherapeutic agents act by inducing apoptosis in proliferating neoplastic cells, but their therapeutic value is limited by the extent to which they are toxic to normal cells. Treatment with standard apoptosis inhibitory molecules, for instance peptide-type caspase inhibitors (e.g., DEVD-type), has proven unsatisfactory for clinical work due to low membrane permeability of these inhibitors.

Targeted immunotoxins (genetic or biochemical fusions between a toxic molecule, for instance a bacterial toxin, and a targeting domain derived, typically from an antibody molecule) have been proposed in attempts to selectively eliminate cancer cells. For example, diphtheria toxin (DT) variants have been generated and tested for their ability to selectively kill cancer cells (Thorpe et al., Nature 271:752-755, 1978; Laske et al., Nature Medicine 3:1362-1368, 1997). Similarly, *Pseudomonas* exotoxin (PE) fusion proteins have been investigated as potential cancer therapeutics (Kreitman and Pastan, Blood 90:252-259, 1997; Shimamura et al. Cancer Res. 67:9903-9912; 2007).

SUMMARY OF THE INVENTION

The present invention relates to interleukin-4 receptor binding fusion proteins. More specifically, the invention provides, in part, fusion proteins that include a interleukin-4 receptor-binding protein moiety joined to a pro-apoptotic Bcl-2 family member protein moiety and uses thereof.

In one aspect, the invention provides a fusion protein including a interleukin-4 (IL-4) receptor binding protein and a pro-apoptotic Bcl-2 family polypeptide. In some embodiments, the IL-4 receptor binding protein may be circularly permuted (cp). In some embodiments, the Bcl-2 family polypeptide may be a pro-apoptotic Bcl-2 family polypeptide comprising a BH3 domain (such as Bad, Bik/Nbk, Bid, Bim/Bod, Hrk, Bak or Bax). The BH3 domain may further include a mutation that reduces phosphorylation. The pro-apoptotic Bcl-2 family polypeptide including a BH3 domain that further includes a mutation that reduces phosphorylation may be a Bad polypeptide. The fusion protein may be capable of inhibiting cell survival, inhibiting cell proliferation, or enhancing cell death or apoptosis of a target cell expressing an IL-4R.

In some embodiments, the IL-4 receptor binding protein may be a mutant IL-4 or IL-13 selective for binding to a Type I or a Type II IL-4 receptor (IL-4R). The mutant IL-4 selective for binding to a Type II IL-4R may include a KFR variant or a KF variant. The mutant IL-4 selective for binding to a Type I IL-4R may include an RGA variant. The mutant IL-13 may be an A11 variant or a DN variant.

In some embodiments, the fusion protein may further include a linker. The linker may have the sequence GS or may be a ubiquitin or ubiquitin variant molecule. The fusion protein may include the sequence set forth in SEQ ID NOs: 24-27.

In some aspects, there is provided a nucleic acid molecule encoding a fusion protein as described herein, or a vector including the nucleic acid molecule, or a host cell including the vector. In some aspects, there is provided a nucleic acid molecule encoding a fusion protein as set forth in SEQ ID NOs: 24-27 or comprising SEQ ID NOs: 35-38.

In some aspects, there is provided a pharmaceutical composition including a fusion protein as described herein, a nucleic acid molecule encoding the fusion protein, or a vector including the nucleic acid molecule, or a host cell including the vector.

In some aspects, there is provided a method of inducing cell death by administering a fusion protein including a pro-apoptotic Bcl-2 family polypeptide, a nucleic acid molecule encoding the fusion protein, or a vector including the nucleic acid molecule, or a host cell including the vector, to a subject in need thereof.

In some aspects, there is provided a method of inducing cell death by contacting a target cell that expresses an IL-4R with a fusion protein including a pro-apoptotic Bcl-2 family polypeptide, a nucleic acid molecule encoding the fusion protein, or a vector including the nucleic acid molecule.

In some aspects, there is provided a method of treating cancer by administering: a fusion protein including a pro-apoptotic Bcl-2 family polypeptide, a nucleic acid molecule encoding the fusion protein, or a vector including the nucleic acid molecule, or a host cell including the vector, to a subject in need thereof.

In some aspects, there is provided a method of treating cancer by contacting a neoplastic cell that expresses an IL-4R with a fusion protein including a pro-apoptotic Bcl-2 family polypeptide, a nucleic acid molecule encoding the fusion protein, or a vector including the nucleic acid molecule.

In some aspects, there is provided a method of treating cancer by contacting a non-malignant cell that expresses an IL-4R in a tumour microenvironment in a subject in need thereof with a fusion protein including a pro-apoptotic Bcl-2 family polypeptide, a nucleic acid molecule encoding the fusion protein, or a vector including the nucleic acid molecule. In some embodiments, the non-malignant cell is contacted prior to the subject starting a therapy.

In some aspects, there is provided a method of treating a hyperproliferative or differentiative disorder by administering a fusion protein including a pro-apoptotic Bcl-2 family polypeptide, a nucleic acid molecule encoding the fusion protein, or a vector including the nucleic acid molecule to a subject in need thereof. The hyperproliferative or differentiative disorder may be a fibrosis or hyperplasia, an inflammatory conditions or an autoimmune condition. The fibrosis or hyperplasia may be pulmonary fibrosis or hyperplasia (such as benign prostatic hyperplasia), cardiac fibrosis, or liver fibrosis; the inflammatory condition may be prostatitis, vernal keratoconjunctivitis, artherosclerosis, or idiopathic pulmonary pneumonia; or the autoimmune condition may be Graves disease.

In some aspects, there is provided a use of a fusion protein including a pro-apoptotic Bcl-2 family polypeptide, a nucleic acid molecule encoding the fusion protein, or a vector including the nucleic acid molecule for inducing cell death or treating cancer or treating a hyperproliferative or differentiative disorder in a subject in need thereof.

In various embodiments of the alternative aspects, the subject may be a human.

This summary does not necessarily describe all features of the invention.

BRIEF DESCRIPTION OF THE DRAWINGS

These and other features of the invention will become more apparent from the following description in which reference is made to the appended drawings wherein:

FIG. 1 is an illustration of a cpIL-4BAD (cpIL-4g:s-BADaa) in a pET 24a expression vector;

FIG. 2 is a graph showing the effect of cpIL-4BAD (cpIL-4BADaa) on IL-4Rα positive tumor cell (U 251) viability;

FIG. 3 is a graph showing the effect of cpIL-4BAD (cpIL-4BADaa) (squares) on IL-4Rα positive tumor cell (U 251) viability in the presence of excess IL-4 (triangles);

FIG. 4 is a graph showing the effect of cpIL-4BAD (cpIL-4BADaa) on IL-4Rα positive tumor cell (Daudi cell) viability;

FIG. 5 is a graph showing the effect of cpIL-4BAD (cpIL-4BADaa) (triangles) on IL-4Rα positive tumor cell Daudi viability in the presence of excess IL-4 (squares);

FIG. 6 is a graph showing the effect of cpIL-4BAD (cpIL-4BADaa) on the colony number of IL-4Rα positive tumor cells (U 251);

FIG. 7 is a graph showing the effect of intratumoural (squares) and intraperitoneal (triangles) injection of cpIL-4BAD fusion protein in athymic mice after the development of subcutaneous glioma tumors with U 251 tumor cells (circles=controls);

FIG. 8 is a graph showing the survival of cpIL-4BAD-treated mice (intratumoural injection group=open diamonds, intraperitoneal injection group=triangles, controls=solid diamonds);

FIG. 9 shows an illustration of a pGW07 *E. coli* expression vector;

FIGS. 10A-F show the nucleic acid (SEQ ID NOs: 29, 30 and 32) and amino sequences (SEQ ID NOs: 18, 19 and 21) of IL-4BAD (A-B), cpIL-4BAD (C-D) and cpS4-BAD (E-F) fusion constructs;

FIGS. 11A-B show the nucleic acid (A; SEQ ID NO: 37) and amino sequence (B; SEQ ID NO: 26) of a pKFR4-BAD-H6 fusion construct.

DETAILED DESCRIPTION

The present disclosure provides, in part, a fusion protein including an IL-4R binding protein joined to a pro-apoptotic Bcl-2 family protein and uses thereof.

IL-4R Binding Proteins IL-4R binding proteins include IL-4 and IL-13.

IL-4 proteins or IL-4 "protein moieties" include native IL-4 proteins, as well as variant IL-4 proteins. A "native" or "wild type" IL-4 sequence, as used herein, refers to a human IL-4 sequence, whether purified from natural sources or made using recombinant techniques, and including the amino acid sequence (with an additional methionine at the N-terminus) as follows:

(SEQ ID NO: 1)
MHKCDITLQEIIKTLNSLTEQKTLCTELTVTDIFAASKNTTEKETFCRAA

TVLRQFYSHHEKDTRCLGATAQQFHRHKQLIRFLKRLDRNLWGLAGLNSC

PVKEANQSTLENFLERLKTIMREKYSKCSS.

Alternative human IL-4 sequences include the amino acid sequence (with an additional methionine at the N-terminus) as follows:

(SEQ ID NO: 2)
MHKCDITLQEIIKTLNSLTEQKTLCTELTVTDIFAASKDTTEKETFCRAA

TVLRQFYSHHEKDTRCLGATAQQFHRHKQLIRFLKRLDRNLWGLAGLNSC

PVKEANQSTLENFLERLKTIMREKYSKCSS.

In some embodiments, IL-4 proteins that can be used in the fusion proteins of the present disclosure are variant IL-4 proteins that have increased selectivity for γc (Type I receptor) relative to IL-13R α1 (Type II receptor) or vice versa as described, for example, in Junttila et al. (Nature Chemical Biology 8:990-998, 2012). In some embodiments, a variant IL-4 protein that has increased selectivity for γc (Type I receptor) is an IL-4 protein that includes the following mutations relative to the sequence of native human IL-4 (e.g., SEQ ID NO: 1) or an alternative IL-4 sequence (e.g., SEQ ID NO:2), the numbering excluding the methionine at the N-terminus: R121Q/Y124W/S125F (the "RGA" or "super-4" or "S4" variant) as described, for example, in Junttila et al. (Nature Chemical Biology 8:990-998, 2012).

In some embodiments, a variant IL-4 protein that has increased selectivity for IL-13R α1 (Type II receptor) is an IL-4 protein that includes the following mutations relative to the sequence of native human IL-4 (e.g., SEQ ID NO: 1) or an alternative IL-4 sequence (e.g., SEQ ID NO:2), the numbering excluding the methionine at the N-terminus: R121K/Y124F/S125R (the "KFR" or "KFR4" variant) or R121K/Y124F (the "KF" variant).

In some embodiments, IL-4 proteins that can be used in the fusion proteins of the present disclosure are circularly permuted (cp), as described in, for example, U.S. Pat. No. 6,011,002, issued Jan. 4, 2000, to Pastan et al. In some embodiments, a cpIL-4 protein that can be used in the fusion proteins of the present disclosure includes an IL-4 protein in which residues 38-129 of native human IL-4 (e.g., SEQ ID NO: 1) or an alternative IL-4 sequence (e.g., SEQ ID NO:2), the numbering excluding the methionine at the N-terminus, are joined to residues 1-37 with a GGNGG (SEQ ID NO: 47) linker and an initial methionine residue, as follows:

(SEQ ID NO: 3)
MDTTEKETFCRAATVLRQFYSHHEKDTRCLGATAQQFHRHKQLIRFLKRL

DRNLWGLAGLNSCPVKEANQSTLENFLERLKTIMREKYSKCSSGGNGGHK

CDITLQEIIKTLNSL TEQKTLCTEL TVTDIFAAS.

In alternative embodiments, a cpIL-4 protein that can be used in the fusion proteins of the present disclosure includes an IL-4 protein in which residues 38-129 of native human IL-4 (e.g., SEQ ID NO: 1) or an alternative IL-4 sequence (e.g., SEQ ID NO:2), the numbering excluding the methionine at the N-terminus, are joined to residues 1-37 with a GGNGG (SEQ ID NO: 47) linker and an initial methionine residue, in the context of an "RGA" or "super-4" or "S4" variant, as follows:

(SEQ ID NO: 4)
MDTTEKETFCRAATVLRQFYSHHEKDTRCLGATAQQFHRHKQLIRFLKRL

DRNLWGLAGLNSCPVKEANQSTLENFLERLRVIMQ§.KWFKCGAGGNGGH

KCDITLQEIIKTLNSL TEQKTLCTEL TVTDIFAAS.

In alternative embodiments, a cpIL-4 protein that can be used in the fusion proteins of the present disclosure includes an IL-4 protein in which residues 38-129 of native human IL-4 (e.g., SEQ ID NO: 1) or an alternative IL-4 sequence (e.g., SEQ ID NO:2), the numbering excluding the methionine at the N-terminus, are joined to residues 1-37 with a GGNGG (SEQ ID NO: 47) linker and an initial methionine residue, in the context of a "KFR" variant, as follows:

(SEQ ID NO: 5)
MDTTEKETFCRAATVLRQFYSHHEKDTRCLGATAQQFHRHKQLIRFLKRL

DRNLWGLAGLNSCPVKEANQSTLENFLERLKTIMKEKFRKCSSGGNGGHK

CDITLQEIIKTLNSL TEQKTLCTEL TVTDIFAAS.

In alternative embodiments, a cpIL-4 protein that can be used in the fusion proteins of the present disclosure includes an IL-4 protein in which residues 38-129 of native human IL-4 (e.g., SEQ ID NO: 1) or an alternative IL-4 sequence (e.g., SEQ ID NO:2), the numbering excluding the methionine at the N-terminus, are joined to residues 1-3 7 with a GGNGG (SEQ ID NO: 47) linker and an initial methionine residue, in the context of a "KF" variant, as follows:

(SEQ ID NO: 6)
MDTTEKETFCRAATVLRQFYSHHEKDTRCLGATAQQFHRHKQLIRFLKRL

DRNLWGLAGLNSCPVKEANQSTLENFLERLKTIMKEK,EKCSSGGNGGHK

CDITLQEIIKTLNSL TEQKTLCTEL TVTDIFAAS.

In alternative embodiments, a cpIL-4 protein that can be used in the fusion proteins of the present disclosure includes an IL-4 protein in which residues 105-129 of native human IL-4 (e.g., SEQ ID NO: 1) or an alternative IL-4 sequence (e.g., SEQ ID NO:2), the numbering excluding the methionine at the N-terminus, are joined to residues 1-104 with a GGNGG (SEQ ID NO: 47) linker and an initial methionine residue, as described in, for example, U.S. Pat. No. 6,011,002, issued Jan. 4, 2000, to Pastan et al.

Exemplary IL-4 proteins that can be used in the fusion proteins of the present disclosure include those described herein, as well as sequences having at least 80% sequence identity, at least 85%, at least 90%, at least 95%, at least 98% or even at least 99% sequence identity to native IL-4 ("variant IL-4 proteins"), as long as the variant IL-4 protein retains the ability to bind the IL-4 receptor, or retains increased selectivity for the γc (Type I receptor) relative to IL-13R α1 (Type II receptor) or vice versa as described, for example, in Junttila et al. (Nature Chemical Biology 8:990-998, 2012), or retains a desired biological activity.

It is to be understood that IL-4 proteins according to the present disclosure include fragments that can be smaller than the native 129 amino acid IL-4 protein, as long as the IL-4 protein fragment retains the ability to bind the IL-4 receptor, or retains increased selectivity for the γc (Type I receptor) relative to IL-13R α1 (Type II receptor) or vice versa as described, for example, in Junttila et al. (Nature Chemical Biology 8:990-998, 2012), or retains a desired biological activity, whether as a fragment of the native sequence, or in a cp form or fragment thereof.

It is also to be understood that the present disclosure encompasses nucleic acid molecules that encode an IL-4 protein as described herein or known in the art, including but not limited to RNA sequences corresponding to the DNA sequences described herein.

Exemplary IL-4 nucleic acid molecules include:

```
                                       (IL4; SEQ ID NO: 30)
ATGCACAAATGCGACATTACCCTGCAAGAGATCATTAAGACCCTGAACAG

CCTGACCGAGCAAAAGACCCTGTGTACCGAACTGACCGTCACGGACATCT

TCGCTGCGTCCAAGGACACTACGGAAAAGGAAACGTTCTGTCGTGCGGCG

ACGGTGCTGCGCCAGTTCTACAGCCACCATGAGAAAGATACCCGTTGCCT

CGGTGCGACCGCGCAACAGTTCCACCGTCACAAACAGCTGATTCGCTTCC

TGAAGCGTCTGGATCGCAACCTGTGGGGTTTGGCGGGTCTGAACTCCTGT

CCAGTCAAAGAAGCCAATCAGTCTACGCTGGAAAACTTTTTGGAGCGTCT

GAAAACTATCATGCGTGAGAAGTACAGCAAATGCAGCAGC;

(cpIL4; SEQ ID NO: 31)
ATGGATACCACCGAGAAAGAAACGTTCTGCCGTGCTGCCACTGTCCTGCG

CCAGTTTTACAGCCATCACGAAAAGGACACCCGTTGCCTGGGTGCGACGG

CGCAGCAATTCCACCGCCACAAACAGCTGATTCGTTTCCTGAAGCGTCTG

GACCGTAACCTGTGGGGTCTGGCGGGTCTGAACAGCTGTCCAGTGAAAGA

AGCGAATCAGAGCACCTTGGAGAATTTCCTCGAACGCCTGAAAACCATCA

TGCGTGAGAAATACAGCAAGTGTTCTAGCGGCGGTAACGGTGGCCACAAA

TGCGATATCACCCTGCAAGAGATCATTAAGACGCTGAACTCCTTGACGGA

ACAAAAGACCCTGTGTACTGAGCTGACGGTCACCGACATTTTCGCGGCGT

CC;

(the cpKFR; SEQ ID NO: 32)
ATGGATACTACCGAGAAAGAAACGTTTTGCCGTGCTGCGACCGTCCTGCG

TCAGTTCTACAGCCACCACGAAAAGGACACCCGCTGTCTGGGTGCGACTG

CCCAACAATTCCATCGTCACAAACAGCTGATTCGTTTCCTGAAGCGTCTG

GACCGCAACCTGTGGGGTCTGGCGGGCTTGAACTCCTGCCCAGTCAAAGA

AGCGAACCAAAGCACCCTGGAAAACTTCTTGGAGCGTCTGAAAACGATCA

TGAAAGAGAAGTTCCGCAAGTGTAGCAGCGGTGGTAATGGTGGCCACAAG

TGCGACATTACGCTGCAGGAAATCATTAAGACCCTGAACTCTCTGACCGA

GCAGAAAACCCTCTGTACCGAGCTGACGGTGACGGATATCTTTGCGGCGA

GC;
and
                                      (cpS4; SEQ ID NO: 33)
ATGGATACCACCGAAAAGAAACTTTTTGTCGTGCCGCGACTGTCCTGCG

CCAGTTCTACAGCCACCACGAAAAGGACACCCGTTGCCTGGGTGCGACCG

CTCAACAATTCCATCGCCACAAACAGCTGATTCGTTTCCTGAAACGTCTG
```

```
GATCGCAACCTGTGGGGTCTGGCGGGGTTTGAACAGCTGTCCAGTCAAAGA

AGCGAACCAGAGCACCCTGGAAAACTTTCTGGAGCGTCTGCGTGTTATCA

TGCAGAGCAAGTGGTTCAAGTGCGGTGCGGGTGGCAATGGTGGCCACAAG

TGTGACATTACCTTGCAAGAGATTATCAAAACGCTGAACTCTCTGACCGA

GCAAAAGACGCTGTGCACCGAGCTGACGGTGACGGACATCTTCGCGGCGT

CC.
```

IL-13 proteins or IL-13 "protein moieties" include native IL-13 proteins, as well as variant IL-13 proteins. A "native" or "wild type" IL-13 sequence, as used herein, refers to a human IL-13 sequence, whether purified from natural sources or made using recombinant techniques, and including the amino acid sequence (with an additional methionine at the N-terminus) as follows:

```
                                             (SEQ ID NO: 7)
MPGPVPPSTALRELIEELVNITQNQKAPLCNGSMVWSINLTAGMYCAALE

SLINVSGCSAIEKTQRMLSGFCPHKVSAGQFSSLHVRDTKIEVAQFVKDL

LLHLKKLFREGQFN.
```

In some embodiments, IL-13 proteins that can be used in the fusion proteins of the present disclosure are variant IL-13 proteins that have increased selectivity for IL-13Rα1 (type II receptor) relative wild-type IL-13 protein. For example, the IL-13 variant sequence may include the amino acid sequence (with an additional methionine at the N-terminus) as follows:

```
                              (the "A11" variant; SEQ ID NO: 8)
MPGPVPPSTAVRELIEELINITQNQKAPLCNGSMVWSINRTAGMYCAALE

SLINVSGCSAIEKTQRMLSGFCPHKVSAGQFSSLHVRSSKIEVAQFVKDL

LFHLRTLFREGQFN.
```

In some embodiments, a variant IL-13 protein that has increased selectivity for IL-13Rα1 (type II receptor) relative wild-type IL-13 protein is an IL-13 protein that includes the following mutations relative to the sequence of native human IL-13 (SEQ ID NO: 7), the numbering excluding the methionine at the N-terminus: L10V/E12A/V18I/R65D/D87S/T88S/L101F/K104R/K105T (the "DN" variant). For example, the IL-13 variant sequence may include the amino acid sequence (with an additional methionine at the N-terminus) as follows:

```
                                             (SEQ ID NO: 9)
MPGPVPPSTAVRALIEELINITQNQKAPLCNGSMVWSINLTAGMYCAALE

SLINVSGCSAIEKTQDMLSGFCPHKVSAGQFSSLHVRSSKIEVAQFVKDL

LFHLRTLFREGQFN.
```

In some embodiments, IL-13 proteins that can be used in the fusion proteins of the present disclosure are circularly permuted (cp). In some embodiments, a variant cpIL-13 protein that can be used in the fusion proteins of the present disclosure includes an IL-13 protein in which residues 44-114 of native human IL-13 (SEQ ID NO: 7) are joined to residues 1-43 with a linker and an initial methionine residue, as follows:

```
                                                    (SEQ ID NO: 10)
MYCAALESLINVSGCSAIEKTQRMLSGFCPHKVSAGQFSSLHVRDTKIEV

AQFVKDLLLHLKKLFREGQFN*GGSG*PGPVPPSTALRELIEELVNITQN

QKAPLCNGSMVWSINLTAG.
```

In some embodiments, a variant cpIL-13 protein that can be used in the fusion proteins of the present disclosure is as follows:

```
                                                    (SEQ ID NO: 11)
MYCAALESLINVSGCSAIEKTQRMLSGFCPHKVSAGQFSSLHVRDTKIEV

AQFVKDLLLHLKKLFREGQFN*GGSG*MPGPVPPSTALRELIEELVNITQN

QKAPLCNGSMVWSINLTAG.
```

In alternative embodiments, a variant cpIL-13 protein that can be used in the fusion proteins of the present disclosure includes an IL-13 protein in which residues 44-114 of native human IL-13 (SEQ ID NO: 7) are joined to residues 1-43 with a linker and an initial methionine residue, in the context of the "A11" variant, as follows:

```
                                                    (SEQ ID NO: 12)
MYCAALESLINVSGCSAIEKTQRMLSGFCPHKVSAGQFSSLHVRSSKIEV

AQFVKDLLFHLRTLFREGQFN*GGSG*PGPVPPSTAVRELIEELINITQN

QKAPLCNGSMVWSINRTAG.
```

In some embodiments, a variant cpIL-13 protein that can be used in the fusion proteins of the present disclosure is as follows:

```
                                                    (SEQ ID NO: 13)
MYCAALESLINVSGCSAIEKTQRMLSGFCPHKVSAGQFSSLHVRSSKIEV

AQFVKDLLFHLRTLFREGQFN*GGSG*MPGPVPPSTAVRELIEELINITQ

NQKAPLCNGSMVWSINRTAG.
```

In alternative embodiments, a variant cpIL-13 protein that can be used in the fusion proteins of the present disclosure includes an IL-13 protein in which residues 44-114 of native human IL-13 (SEQ ID NO: 7) are joined to residues 1-43 with a linker and an initial methionine residue, in the context of the "DN" variant, as follows:

```
                                                    (SEQ ID NO: 14)
MYCAALESLINVSGCSAIEKTQDMLSGFCPHKVSAGQFSSLHVRSSKIEV

AQFVKDLLFHLRTLFREGQFN*GGSG*PGPVPPSTAVRALIEEL

INITQNQKAPLCNGSMVWSINLTAG.
```

In some embodiments, a variant cpIL-13 protein that can be used in the fusion proteins of the present disclosure is as follows:

```
                                                    (SEQ ID NO: 15)
MYCAALESLINVSGCSAIEKTQDMLSGFCPHKVSAGQFSSLHVRSSKIEV

AQFVKDLLFHLRTLFREGQFN*GGSG*MPGPVPPSTAVRALIEEL

INITQNQKAPLCNGSMVWSINLTAG.
```

Exemplary IL-13 proteins that can be used in the fusion proteins of the present disclosure include those described herein, as well as sequences having at least 80% sequence identity, at least 85%, at least 90%, at least 95%, at least 98% or even at least 99% sequence identity to native IL-13 ("variant IL-13 proteins"), as long as the variant IL-13 protein retains the ability to bind the IL-13 receptor, or retains increased selectivity for the IL-13Rα1 (type II receptor) relative to wild-type IL-13 protein, or retains a desired biological activity.

It is to be understood that IL-13 proteins according to the present disclosure include fragments that can be smaller than the native 114 amino acid IL-13 protein, as long as the IL-13 protein fragment retains the ability to bind the IL-13 receptor, or retains increased selectivity for the IL-13Rα1 (type II receptor) relative to wild-type IL-13 protein, or retains a desired biological activity.

It is also to be understood that the present disclosure encompasses nucleic acid molecules (including but not limited to RNA sequences or DNA sequences) that encode an IL-13 protein as described herein or known in the art.

BCL-2 Family Proteins

Bcl-2-related proteins or polypeptides ("Bcl-2 family proteins" or "Bcl-2 family members") are involved in regulation of apoptosis. Bcl-2 family proteins fall into two distinct categories: those that inhibit cell death (the "anti-apoptotic" Bcl-2 family proteins) and those that enhance cell death (the "pro-apoptotic" Bcl-2 family proteins). Bcl-2 family proteins share one to four conserved Bcl-2 homology (BH) domains, designated BH1, BH2, BH3, and BH4.

Pro-apoptotic Bcl-2 family proteins include those having a BH3 domain, such as Bad (e.g., Accession no: NP116784, CAG46757 or Q92934), Bik/Nbk (e.g., Accession no: CAG30276 or Q13323), Bid (e.g., Accession no: CAG28531 or P55957), Bim/Bod (e.g., Accession no: NP619527), Hrk (Accession no: O00198), Bak, or Bax. In some embodiments, pro-apoptotic Bcl-2 family proteins that can be used in the fusion proteins according to the present disclosure are mutated (for example at serine residues e.g., serine to alanine mutations) to prevent phosphorylation.

Bad, Bcl-2-associated agonist of cell death, is a regulator of programmed cell death (apoptosis). Bad positively regulates cell apoptosis by forming heterodimers with Bcl-$x_L$ and Bcl-2, and reversing their death repressor activity. Pro-apoptotic activity of Bad is regulated through its phosphorylation. Exemplary Bad proteins that can be used in the fusion proteins of the present disclosure include those in GenBank Accession Nos. CAG46757; AAH01901.1; and CAG46733.1, as well as those sequences provided in U.S. Pat. No. 6,737,511 (sequences herein incorporated by reference) and described herein, as well as sequences having at least 80% sequence identity, at least 85%, at least 90%, at least 95%, at least 98% or even at least 99% sequence identity to such sequences, as long as the variant retains or has enhanced biological activity of the native Bad protein. In some embodiments, a Bad protein that can be used in the fusion proteins according to the present disclosure contains serine mutations at positions 112 and/or 136 to reduce phosphorylation. In some embodiments, a Bad protein that can be used in the fusion proteins according to the present disclosure contains serine to alanine mutations at positions 112 and/or 136 to reduce phosphorylation. In some embodiments, a Bad protein that can be used in the fusion proteins according to the present disclosure includes a sequence as follows, or fragment thereof:

(SEQ ID NO: 16)
FQIPEFEPSEQEDSSSAERGLGPSPAGDGPSGSGKHHRQAPGLLWDASHQ

QEQPTSSSHHGGAGAVEIRSRHSSYPAGTEDDEGMGEEPSPFRGRSRAAP

PNLWAAQRYGRELRRMSDEFVDSFKKGLPRPKSAGTATQMRQSSSWTRVF

QSWWDRNLGRGSSAPSQ;

(Accession no: NP116784; SEQ ID NO: 18)
FQIPEFEPSEQEDSSSAERGLGPSPAGDGPSGSGKHHRQAPGLLWDASHQ

QEQPTSSSHHGGAGAVEIRSRHSSYPAGTEDDEGMGEEPSPFRGRSRSAP

PNLWAAQRYGRELRRMSDEFVDSFKKGLPRPKSAGTATQMRQSSSWTRVF

QSWWDRNLGRGSSAPSQ;
or (Accession no: CAG46757; SEQ ID NO: 19)
FQIPEFEPSEQEDSSSAERGLGPSPAGDGPSGSGKHHRQAPGLLWDASHQ

QEQPTSSSHHGGAGAVEIRSRHSSYPAGTEDDEGMGEEPSPFRGRSRSAP

PNLWAAQRYGRELRRMSDEFVDSFKKGLP RPKSAGTATQ MRQSSSWTR

VFQSVVWDRNLGRGSSAPSQ.

In some embodiments, a Bad protein that can be used in the fusion proteins according to the present disclosure includes a variant sequence as follows, or fragment thereof:

(SEQ ID NO: 17)
FQIPEFEPSEQEDSSSAERGLGPSPAGDGPSGSGKHHRQAPGLLWDASHQ

QEQPTSSSHHGGAGAVEIRSRHSAYPAGTEDDEGMGEEPSPFRGRSRAAP

PNLWAAQRYGRELRRMSDEFVDSFKKGLPRPKSAGTATQMRQSSSWTRVF

QSWWDRNLGRGSSAPSQ.

An exemplary Bik/Nbk protein molecule that can be used in the fusion proteins according to the present disclosure includes a sequence as follows, or fragment thereof:

(Accession no: CAG30276; SEQ ID NO: 20)
SEVRPLSRDILMETLLYEQLLEPPTMEVLGMTDSEEDLDPMEDFDSLECM

EGSDALALRLACIGDEMDVSLRAPRLAQLSEVAMHSLGLAFIYDQTEDIR

DVLRSFMDGFTTLKENIMRFWRSPNPGSWVSCEQVLLALLLLLALLLPLL

SGGLHLLLK.

An exemplary Bid protein molecule that can be used in the fusion proteins according to the present disclosure includes a sequence as follows, or fragment thereof:

(Accession no: CAG28531; SEQ ID NO: 21)
DCEVNNGSSLRDECITNLLVFGFLQSCSDNSFRRELDALGHELPVLAPQW

EGYDELQTDGNRSSHSRLGRIEADSESQEDIIRNIARHLAQVGDSMDRSI

PPGLVNGLALQLRNTSRSEEDRNRDLATALEQLLQAYPRDMEKEKTMLVL

ALLLAKKVASHTPSLLRDVFHTTVNFINQNLRTYVRSLARNGMD.

An exemplary Bim/Bod protein molecule that can be used in the fusion proteins according to the present disclosure includes a sequence as follows:

(Accession no: MP619527; SEQ ID NO: 22)
AKQPSDVSSECDREGRQLQPAERPPQLRPGAPTSLQTEPQGNPEGNHGGE

GDSCPHGSPQGPLAPPASPGPFATRSPLFIFMRRSSLLSRSSSGYFSFDT

DRSPAPMSCDKSTQTPSPPCQAFNHYLSAMASMRQAEPADMRPEIWIAQE

LRRIGDEFNAYYARRVFLNNYQAAEDHPRMVILRLLRYIVRLVWRMH.

An exemplary Hrk protein molecule that can be used in the fusion proteins according to the present disclosure includes a sequence as follows:

(Accession no: O00198; SEQ ID NO: 23)
CPCPLHRGRGPPAVCACSAGRLGLRSSAAQLTAARLKALGDELHQRTMWR

RRARSRRAPAPGALPTYWPWLCAAAQVAALAAWLLGRRN.

In some embodiments, a pro-apoptotic Bcl-2 family protein includes at least a fragment of a Bcl-2 family member, where the pro-apoptotic Bcl-2 family protein or fragment is capable of inhibiting cell survival, inhibiting cell proliferation, or enhancing cell death or apoptosis. By "inhibiting cell survival" is meant decreasing (e.g., by at least 10%, 20%, 30%, or by as much as 50%, 75%, 85% or 90% or more) the probability that a cell at risk of cell death will survive. By "inhibiting cell proliferation" is meant decreasing (e.g., by at least 10%, 20%, 30%, or by as much as 50%, 75%, 85% or 90% or more) the growth or proliferation of a cell. By "enhancing cell death or apoptosis" is meant increasing (e.g., by at least 10%, 20%, 30%, or by as much as 50%, 75%, 85% or 90% or more) the probability that a cell at risk of cell death will undergo apoptotic, necrotic, or any other form of cell death. Suitable assays for measuring the inhibition of cell survival, inhibition of cell proliferation, or enhancement of cell death or apoptosis are described herein or known in the art.

It is also to be understood that the present disclosure encompasses nucleic acid molecules (e.g., RNA sequences or DNA sequences) that encode a pro-apoptotic Bcl-2 family member as described herein, including but not limited to RNA sequences corresponding to the DNA sequences described herein.

An exemplary pro-apoptotic Bcl-2 family member nucleic acid molecule includes:

(variant BAD; SEQ ID NO: 34)
GGTAGCTTTCAGATCCCGGAATTTGAGCCGAGCGAGCAAGAGGATTCAAG

CAGCGCGGAGCGCGGTCTGGGTCCGAGCCCGGCAGGCGACGGTCCGAGCG

GCAGCGGCAAGCATCACCGCCAGGCGCCAGGCCTGCTGTGGGATGCATCG

CATCAACAGGAACAACCGACGAGCAGCAGCCATCATGGTGGCGCTGGTGC

GGTTGAGATTAGATCGCGCCACTCCGCATATCCTGCCGGCACCGAAGATG

ACGAAGGCATGGGCGAGGAACCGAGCCCGTTCCGTGGCCGTAGCCGTGCT

GCACCGCCGAATCTGTGGGCCGCACAGCGTTATGGTCGCGAGTTGCGTCG

CATGTCCGACGAGTTTGTTGACTCCTTCAAGAAAGGTTTACCGCGTCCGA

AATCTGCCGGTACCGCGACGCAGATGCGTCAGAGCAGCAGCTGGACCCGC

GTGTTTCAATCTTGGTGGGATCGTAATCTGGGTCGTGGTAGCAGCGCACC

GAGCCAA.

IL-4 Receptor Binding Protein-Bcl-2 Family Fusion Proteins

"Fusion proteins" according to the present disclosure include IL-4R binding proteins, such as IL-4 and IL-13, joined to a pro-apoptotic Bcl-2 family member, with optional additional sequences or moieties (such as linkers), as described herein, as well as nucleic acid molecules encoding such fusion proteins. Also encompassed are recombinant nucleic acid molecules in which a nucleic acid sequence encoding a fusion protein is operably linked to a promoter, vectors containing such a molecule, and transgenic cells comprising such a molecule.

IL-4 (including cpIL-4 and IL-4 fragments and variants) can be linked to pro-apoptotic Bcl-2 family polypeptides comprising a BH3 domain as exemplified by Bad, Bik/Nbk, Bid, Bim/Bod, Hrk, Bak, or Bax or combinations thereof, or fragments or variants thereof, as long as pro-apoptotic activity is retained. Any form or derivative of IL-4 can be used. For example, IL-4 or fragments of IL-4 that bind to the IL-4 receptor can be used. Additionally, multiple pro-apoptotic Bcl-2 family proteins or fragments or variants thereof can be joined to IL-4 or fragments or variants thereof or multiple IL-4 proteins or fragments or variants thereof can be joined to pro-apoptotic Bcl-2 family proteins or fragments or variants thereof.

IL-13 (including IL-13 fragments or variants) can be linked to pro-apoptotic Bcl-2 family polypeptides, for example those comprising a BH3 domain, as exemplified by Bad, Bik/Nbk, Bid, Bim/Bod, or Hrk, or combinations thereof, as long as the combination or fragments or variants thereof retains pro-apoptotic activity. Any form or derivative of IL-13 can be used. For example, IL-13 or fragments of IL-13 that bind to the IL-13 receptor can be used. Additionally, multiple pro-apoptotic Bcl-2 family proteins or fragments or variants thereof can be joined to IL-13 or fragments or variants thereof or multiple IL-13 proteins or fragments or variants thereof can be joined to pro-apoptotic Bcl-2 family proteins or fragments or variants thereof.

A cpIL-4, can be linked to pro-apoptotic Bcl-2 family polypeptides, such as those comprising a BH3 domain as exemplified by Bad, Bik/Nbk, Bid, Bim/Bod, Hrk, Bak, or Bax or combinations thereof, or fragments or variants thereof, as long as pro-apoptotic activity is retained. Any form or derivative of cpIL-4 can be used. Additionally, multiple cpIL-4 proteins or fragments or variants thereof, can be joined to a pro-apoptotic Bcl-2 family protein or fragments or variants thereof, or multiple pro-apoptotic Bcl-2 family proteins or fragments or variants thereof, can be joined to cpIL-4 proteins or fragments or variants thereof.

Exemplary fusion proteins are listed in Table 1.

TABLE 1

IL-4/Bcl-2 Family Fusion Proteins

| Name | Circularly permuted IL-4 | Linker | Bcl-2 Family Protein | Description |
|---|---|---|---|---|
| IL4-Bad | MHKCDITLQEIIKTLN SLTEQKTLCTELTVT DIFAASKDTTEKETF CRAATVLRQFYSHH EKDTRCLGATAQQF HRHKQLIRFLKRLDR NLWGLAGLNSCPVK EANQSTLENFLERLK TIMREKYSKCSS (SEQ ID NO: 2). | GS | FQIPEFEPSEQED SSSAERGLGPSP AGDGPSGSGKHH RQAPGLLWDASH QQEQPTSSSHHG GAGAVEIRSRHSA YPAGTEDDEGMG EEPSPFRGRSRA APPNLWAAQRYG RELRRMSDEFVD SFKKGLPRPKSAG TATQMRQSSSWT RVFQSWWDRNL GRGSSAPSQ (SEQ ID NO: 17). | Human IL-4 fused to human Bad variant via a GS linker |

Fusion Amino Acid Sequence:
MHKCDITLQEIIKTLNSLTEQKTLCTELTVTDIFAASKDTTEKETFCRAATVLRQFYSHHEK
DTRCLGATAQQFHRHKQLIRFLKRLDRNLWGLAGLNSCPVKEANQSTLENFLERLKTIM
REKYSKCSSFQIPEFEPSEQEDSSSAERGLGPSPAGDGPSGSGKHHRQAPGLLWASH
QQEQPTSSSHHGGAGAVEIRSRHSAYPAGTEDDEGMGEEPSPFRGRSRAAPPNLWAA
QRYGRELRRMSDEFVDSFKKGLPRPKSAGTATQMRQSSSWTRVFQSWWDRNLGRGS
SAPSQ (SEQ ID NO: 24).

Fusion DNA Sequence:
ATGCACAAATGCGACATTACCCTGCAAGAGATCATTAAGACCCTGAACAGCCTGACC
GAGCAAAAGACCCTGTGTACCGAACTGACCGTCACGGACATCTTCGCTGCGTCCAA
GGACACTACGGAAAAGGAAACGTTCTGTCGTGCGGCGACGGTGCTGCGCCAGTTCT
ACAGCCACCATGAGAAAGATACCCGTTGCCTCGGTGCGACCGCGCAACAGTTCCAC
CGTCACAAACAGCTGATTCGCTTCCTGAAGCGTCTGGATCGCAACCTGTGGGGTTTG
GCGGGTCTGAACTCCTGTCCAGTCAAAGAAGCCAATCAGTCTACGCTGGAAAACTTT
TTGGAGCGTCTGAAAACTATCATGCGTGAGAAGTACAGCAAATGCAGCAGCGGTAG
CTTTCAGATCCCGGAATTTGAGCCGAGCGAGCAAGAGGATTCAAGCAGCGCGGAGC
GCGGTCTGGGTCCGAGCCCGGCAGGCGACGGTCCGAGCGGCAGCGGCAAGCATC
ACCGCCAGGCGCCAGGCCTGCTGTGGGATGCATCGCATCAACAGGAACAACCGAC
GAGCAGCAGCCATCATGGTGGCGCTGGTGCGGTTGAGATTAGATCGCGCCACTCCG
CATATCCTGCCGGCACCGAAGATGACGAAGGCATGGGCGAGGAACCGAGCCCGTT
CCGTGGCCGTAGCCGTGCTGCACCGCCGAATCTGTGGGCCGCACAGCGTTATGGT
CGCGAGTTGCGTCGCATGTCCGACGAGTTTGTTGACTCCTTCAAGAAAGGTTTACCG
CGTCCGAAATCTGCCGGTACCGCGACGCAGATGCGTCAGAGCAGCAGCTGGACCC
GCGTGTTTCAATCTTGGTGGGATCGTAATCTGGGTCGTGGTAGCAGCGCACCGAGC
CAA (SEQ ID NO: 35).

| cpIL4-Bad | MDTTEKETFCRAATV LRQFYSHHEKDTRC | GS | FQIPEFEPSEQED SSSAERGLGPSP | Circularly permuted human |

TABLE 1-continued

IL-4/Bcl-2 Family Fusion Proteins

| Name | Circularly permuted IL-4 | Linker | Bcl-2 Family Protein | Description |
|---|---|---|---|---|
| | LGATAQQFHRHKQLI RFLKRLDRNLWGLA GLNSCPVKEANQST LENFLERLKTIMREK YSKCSSGGNGGHKC DITLQEIIKTLNSLTEQ KTLCTELTVTDIFAAS (SEQ ID NO: 3). | | AGDGPSGSGKHH RQAPGLLWDASH QQEQPTSSSHHG GAGAVEIRSRHSA YPAGTEDDEGMG EEPSPFRGRSRA APPNLWAAQRYG RELRRMSDEFVD SFKKGLPRPKSAG TATQMRQSSSWT RVFQSWWDRNL GRGSSAPSQ (SEQ ID NO: 17). | IL-4 fused to human Bad variant via a GS linker |

Fusion Amino Acid Sequence:
MDTTEKETFCRAATVLRQFYSHHEKDTRCLGATAQQFHRHKQLIRFLKRLDRNLWGLAG
LNSCPVKEANQSTLENFLERLKTIMREKYSKCSSGGNGGHKCDITLQEIIKTLNSLTEQKT
LCTELTVTDIFAASGSFQIPEFEPSEQEDSSSAERGLGPSPAGDGPSGSGKHHRQAPGL
LWDASHQQEQPTSSSHHGGAGAVEIRSRHSAYPAGTEDDEGMGEEPSPFRGRSRAAP
PNLWAAQRYGRELRRMSDEFVDSFKKGLPRPKSAGTATQMRQSSSWTRVFQSWWDR
NLGRGSSAPSQ (SEQ ID NO: 25).

Fusion DNA Sequence:
ATGGATACCACCGAGAAAGAAACGTTCTGCCGTGCTGCCACTGTCCTGCGCCAGTTTT
TACAGCCATCACGAAAGGACACCCGTTGCCTGGGTGCGACGGCGCAGCAATTCCA
CCGCCACAAACAGCTGATTCGTTTCCTGAAGCGTCTGGACCGTAACCTGTGGGGTCT
GGCGGGTCTGAACAGCTGTCCAGTGAAAGAAGCGAATCAGAGCACCTTGGAGAATT
TCCTCGAACGCCTGAAAACCATCATGCGTGAGAAATACAGCAAGTGTTCTAGCGGCG
GTAACGGTGGCCACAAATGCGATATCACCCTGCAAGAGATCATTAAGACGCTGAACT
CCTTGACGGAACAAAAGACCCTGTGTACTGAGCTGACGGTCACCGACATTTTCGCGG
CGTCCGGTAGCTTTCAGATCCCGGAATTTGAGCCGAGCGAGCAAGAGGATTCAAGC
AGCGCGGAGCGCGGTCTGGGTCCGAGCCCGGCAGGCGACGGTCCGAGCGGCAGC
GGCAAGCATCACCGCCAGGCGCCAGGCCTGCTGTGGGATGCATCGCATCAACAGG
AACAACCGACGAGCAGCAGCCATCATGGTGGCGCTGGTGCGGTTGAGATTAGATCG
CGCCACTCCGCATATCCTGCCGGCACCGAAGATGACGAAGGCATGGGCGAGGAAC
CGAGCCCGTTCCGTGGCCGTAGCCGTGCTGCACCGCCGAATCTGTGGGCCGCACA
GCGTTATGGTCGCGAGTTGCGTCATGTCCGACGAGTTTGTTGACTCCTTCAAGAA
AGGTTTACCGCGTCCGAAATCTGCCGGTACCGCGACGCAGATGCGTCAGAGCAGCA
GCTGGACCCGCGTGTTTCAATCTTGGTGGGATCGTAATCTGGGTCGTGGTAGCAGC
GCACCGAGCCAA (SEQ ID NO: 36).

| cpKFR4-Bad | MDTTEKETFCRAATV LRQFYSHHEKDTRCL GATAQQFHRHKQLIR FLKRLDRNLWGLAGL NSCPVKEANQSTLEN FLERLKTIMKEKFRKC SSGGNGGHKCDITLQ EIIKTLNSLTEQKTLCT ELTVTDIFAAS (SEQ ID NO: 5). | GS | FQIPEFEPSEQEDS SSAERGLGPSPAG DGPSGSGKHHRQ APGLLWDASHQE QPTSSSHHGGAGA VEIRSRHSAYPAG TEDDEGMGEEPSP FRGRSRAAPPNLW AAQRYGRELRRMS DEFVDSFKKGLPR PKSAGTATQMRQS SSWTRVFQSVWVD RNLGRGSSAPSQ (SEQ ID NO: 17). | Circularly permuted KFR variant of human IL-4 fused to human Bad variant via a GS linker |

Fusion Amino Acid Sequence:
MDTTEKETFCRAATVLRQFYSHHEKDTRCLGATAQQFHRHKQLIRFLKRLDRNLWGLAG
LNSCPVKEANQSTLENFLERLKTIMKEKFRKCSSGGNGGHKCDITLQEIIKTLNSLTEQKT
LCTELTVTDIFAASGSFQIPEFEPSEQEDSSSAERGLGPSPAGDGPSGSGKHHRQAPGL
LWDASHQQEQPTSSSHHGGAGAVEIRSRHSAYPAGTEDDEGMGEEPSPFRGRSRAAP
PNLWAAQRYGRELRRMSDEFVDSFKKGLPRPKSAGTATQMRQSSSWTRVFQSWWDR
NLGRGSSAPSQ (SEQ ID NO: 26).

Fusion DNA Sequence:
ATGGATACTACCGAGAAAGAAACGTTTTGCCGTGCTGCCGACCGTCCTGCGTCAGTTC
TACAGCCACCACGAAAGGACACCCGCTGTCTGGGTGCGACTGCCCAACAATTCCA
TCGTCACAAACAGCTGATTCGTTTCCTGAAGCGTCTGGACCGCAACCTGTGGGGTCT
GGCGGGCTTGAACTCCTGCCCAGTCAAAGAAGCGAACCAAAGCACCCTGGAAACT
TCTTGGAGCGTCTGAAAACGATCATGAAAGAAGTTCCGCAAGTGTAGCAGCGGTG
GTAATGGTGGCCACAAGTGCGACATTACGCTGCAGGAAATCATTAAGACCCTGAACT
CTCTGACCGAGCAGAAAACCCTCTGTACCGAGCTGACGGTGACGGATATCTTTGCG
GCGAGCGGTAGCTTTCAGATCCCGGAATTTGAGCCGAGCGAGCAAGAGGATTCAAG
CAGCGCGGAGCGCGGTCTGGGTCCGAGCCCGGCAGGCGACGGTCCGAGCGGCAG
CGGCAAGCATCACCGCCAGGCGCCAGGCCTGCTGTGGGATGCATCGCATCAACAG

TABLE 1-continued

IL-4/Bcl-2 Family Fusion Proteins

| Name | Circularly permuted IL-4 | Linker | Bcl-2 Family Protein | Description |
|---|---|---|---|---|

GAACAACCGACGAGCAGCAGCCATCATGGTGGCGCTGGTGCGGTTGAGATTAGATC
GCGCCACTCCGCATATCCTGCCGGCACCGAAGATGACGAAGGCATGGGCGAGGAA
CCGAGCCCGTTCCGTGGCCGTAGCCGTGCTGCACCGCCGAATCTGTGGGCCGCAC
AGCGTTATGGTCGCGAGTTGCGTCGCATGTCCGACGAGTTTGTTGACTCCTTCAAGA
AAGGTTTACCGCGTCCGAAATCTGCCGGTACCGCGACGCAGATGCGTCAGAGCAGC
AGCTGGACCCGCGTGTTTCAATCTTGGTGGGATCGTAATCTGGGTCGTGGTAGCAG
CGCACCGAGCCAA (SEQ ID NO: 37).

| cpS4-Bad | MDTTEKETFCRAATV LRQFYSHHEKDTRCL GATAQQFHRHKQLIR FLKRLDRNLWGLAGL NSCPVKEANQSTLEN FLERLRVIMQSKWFK CGAGGNGGHKCDITL QEIIKTLNSLTEQKTL CTELTVTDIFAAS (SEQ ID NO: 4). | GS | FQIPEFEPSEQE DSSSAERGLGPS PAGDGPSGSGK HHRQAPGLLWD ASHQQEQPTSSS HHGGAGAVEIRS RHSAYPAGTEDD EGMGEEPSPFR GRSRAAPPNLW AAQRYGRELRR MSDEFVDSFKKG LPRPKSAGTATQ MRQSSSWTRVF QSWWDRNLGRG SSAPSQ (SEQ ID NO: 17). | Circularly permuted RGA (Super-4) variant of IL-4 fused to pro-apoptotic human Bad with GS linker; Mutations in S75A and S99A of Bad |

Fusion Amino Acid Sequence:
MDTTEKETFCRAATVLRQFYSHHEKDTRCLGATAQQFHRHKQLIRFLKRLDRNLWGLAG
LNSCPVKEANQSTLENFLERLRVIMQSKWFKCGA*GGNGG*HKCDITLQEIIKTLNSLTEQK
TLCTELTVTDIFAASGSFQIPEFEPSEQEDSSSAERGLGPSPAGDGPSGSGKHHRQAPG
LLWDASHQQEQPTSSSHHGGAGAVEIRSRHSAYPAGTEDDEGMGEEPSPFRGRSRAA
PPNLWAAQRYGRELRRMSDEFVDSFKKGLPRPKSAGTATQMRQSSSWTRVFQSWWD
RNLGRGSSAPSQ (SEQ ID NO: 27).

Fusion DNA Sequence:
ATGGATACCACCGAAAAAGAAACTTTTTGTCGTGCCGCGACTGTCCTGCGCCAGTTC
TACAGCCACCACGAAAAGGACACCCGTTGCCTGGGTGCGACCGCTCAACAATTCCA
TCGCCACAAACAGCTGATTCGTTTCCTGAAACGTCTGGATCGCAACCTGTGGGGTCT
GGCGGGTTTGAACAGCTGTCCAGTCAAAGAAGCGAACCAGAGCACCCTGGAAAACT
TTCTGGAGCGTCTGCGTGTTATCATGCAGAGCAAGTGGTTCAAGTGCGGTGCGGGT
GGCAATGGTGGCCACAAGTGTGACATTACCTTGCAAGAGATTATCAAAACGCTGAAC
TCTCTGACCGAGCAAAAGACGCTGTGCACCGAGCTGACGGTGCGGACATCTTCGC
GGCGTCCGGTAGCTTTCAGATCCCGGAATTTGAGCCGAGCGAGCAAGAGGATTCAA
GCAGCGCGGAGCGCGGTCTGGGTCCGAGCCCGGCAGGCGACGGTCCGAGCGGCA
GCGGCAAGCATCACCGCCAGGCGCCAGGCCTGCTGTGGGATGCATCGCATCAACA
GGAACAACCGACGAGCAGCAGCCATCATGGTGGCGCTGGTGCGGTTGAGATTAGAT
CGCGCCACTCCGCATATCCTGCCGGCACCGAAGATGACGAAGGCATGGGCGAGGA
ACCGAGCCCGTTCCGTGGCCGTAGCCGTGCTGCACCGCCGAATCTGTGGGCCGCA
CAGCGTTATGGTCGCGAGTTGCGTCGCATGTCCGACGAGTTTGTTGACTCCTTCAAG
AAAGGTTTACCGCGTCCGAAATCTGCCGGTACCGCGACGCAGATGCGTCAGAGCAG
CAGCTGGACCCGCGTGTTTCAATCTTGGTGGGATCGTAATCTGGGTCGTGGTAGCA
GCGCACCGAGCCAA (SEQ ID NO: 38).

The joining or "fusion" of an IL-4R binding protein, such as IL-4 or IL-13, to a pro-apoptotic Bcl-2 ing with the activity of the pro-apoptotic Bcl-2 family member and/or the pro-apoptotic Bcl-2 family member interfering with the activity of the IL-4R binding protein. The linker can also be used to provide, for example, lability to the connection between the IL-4R binding protein and the pro-apoptotic Bcl-2 family member, an enzyme cleavage site (for example, a cleavage site for a protease), a stability sequence, a molecular tag, a detectable label, or various combinations thereof. In some embodiments, a linker can be present between two domains of an IL-4R binding protein (such as in a cp molecule) or pro-apoptotic Bcl-2 family member.

The linker can be bifunctional or polyfunctional, i.e., contain at least about a first reactive functionality at, or proximal to, a first end of the linker that is capable of bonding to, or being modified to bond to, the IL-4R binding protein and a second reactive functionality at, or proximal to, the opposite end of the linker that is capable of bonding to, or being modified to bond to, the pro-apoptotic Bcl-2 family member being modified. The two or more reactive functionalities can be the same (i.e. the linker is homobifunctional) or they can be different (i.e. the linker is heterobifunctional).

The length and composition of a linker can be varied considerably. The length and composition of the linker are generally selected taking into consideration the intended function of the linker, and optionally other factors such as ease of synthesis, stability, resistance to certain chemical and/or temperature parameters, and biocompatibility. For example, the linker should not significantly interfere with the activity of the IL-4R binding protein and/or pro-apoptotic Bcl-2 family member.

Linkers suitable for use in a fusion protein according to the present disclosure include peptides. The linker can be attached to the IL-4R binding moiety and/or the pro-apoptotic Bcl-2 family member moiety using recombinant DNA technology. Such methods are well-known in the art and details of this technology can be found, for example, in Sambrook, et al. Molecular Cloning: A Laboratory Manual. 2$^{nd}$ ed., Cold Spring Harbor Laboratory, Cold Spring Harbor Laboratory Press, Cold Spring Harbor, N.Y., 1989 or Ausubel et al. Current Protocols in Molecular Biology, John Wiley & Sons, 1994) or updates thereto.

The linker peptides can have a chain length of 1 to 500 amino acid residues (such as 1 to 100, 1 to 50, 6 to 30, 1 to 40, 1 to 20, or less than 30 amino acids or 5 to 10 amino acids). In some embodiments, a linker can be 2, 3, 4, 5, 6, 7, or 8 amino acids in length, or can be about 10, 20, 30, 40 or 50 amino acids in length.

Typically, surface amino acids in flexible protein regions include Gly, Asn and Ser, and such amino acids can be used in linker sequences. Other neutral amino acids, such as Thr and Ala, can also be used in the linker sequence. Additional amino acids can be included in the linker to provide unique restriction sites in the linker sequence to facilitate construction of the fusions. In some embodiments, a linker may for instance include the amino acid sequence Gly-Ser (GS) or may be the amino acid sequence Gly-Ser (GS) or may include a ubiquitin sequence: GGGSMQIFVRTLTGRTITLEVEPSDTIENVRARIQDREGIPPDQQRLIFAGRQLEDGRTLS DYNIQRESTLHLVLRLRGGGS (SEQ ID NO: 28) or variant thereof. Ubiquitin molecules suitable for use as linkers are described in, for example, Bachran, C. et al. "Anthrax toxin-mediated delivery of the *Pseudomonas* exotoxin A enzymatic domain to the cytosol of tumor cells via cleavable ubiquitin fusions MBio. 2013 Apr. 30; 4(3):e00201-13, or in PCT publication WO/2012/139112.

Peptide linkers that are susceptible to cleavage by enzymes of the complement system, urokinase, tissue plasminogen activator, trypsin, plasmin, or another enzyme having proteolytic activity may be used in one example. According to another example, the IL-4R binding protein can be attached via a linker susceptible to cleavage by enzymes having a proteolytic activity such as a urokinase, a tissue plasminogen activator, plasmin, thrombin or trypsin. In addition, the IL-4R binding protein can be attached to the pro-apoptotic Bcl-2 family member via disulfide bonds (for example, the disulfide bonds on a cysteine molecule). For example, in the context of pro-apoptotic Bcl-2 family proteins, since many tumors naturally release high levels of glutathione (a reducing agent) this can reduce the disulfide bonds with subsequent release of the pro-apoptotic Bcl-2 family member at the site of delivery.

In some embodiments, a fusion protein according to the present disclosure may include a pro-apoptotic Bcl-2 family member and an IL-4R binding protein linked by a cleavable linker region. In another embodiment, the cleavable linker region can be a protease-cleavable linker, although other linkers, cleavable for example by small molecules, may be used. Examples of protease cleavage sites include those cleaved by factor Xa, thrombin and collagenase. In one example, the protease cleavage site include those cleaved by a protease that is associated with a disease. In another example, the protease cleavage site is one that is cleaved by a protease that is up-regulated or associated with cancers in general. Examples of such proteases are uPA, the matrix metalloproteinase (MMP) family, the caspases, elastase, prostate specific antigen (PSA, a serine protease), and the plasminogen activator family, as well as fibroblast activation protein. In still another example, the cleavage site is cleaved by a protease secreted by cancer-associated cells. Examples of these proteases include matrixmetalloproteases, elastase, plasmin, thrombin, and uPA. In another example, the protease cleavage site is one that is up-regulated or associated with a specific cancer. The precise sequences are available in the art and the skilled person will have no difficulty in selecting a suitable cleavage site. By way of example, the protease cleavage region targeted by Factor Xa is IEGR. The protease cleavage region targeted by enterokinase is DDDDK. The protease cleavage region targeted by thrombin is LVPRG. In one example, the cleavable linker region is one which is targeted by endocellular proteases.

The linker can be attached to the IL-4R binding protein moiety and/or pro-apoptotic Bcl-2 family member moiety using routine techniques as known in the art.

Preparation of IL-4R Binding Protein/Pro-Apoptotic Bcl-2 Family Fusion Proteins

Fusion proteins can be prepared using routine methods as known in the art. Fusion proteins, as well as modifications thereto, can be made, for example, by engineering the nucleic acid encoding the fusion protein using recombinant DNA technology or by peptide synthesis. Modifications to the fusion protein may be made, for example, by modifying the fusion protein polypeptide itself, using chemical modifications and/or limited proteolysis. Combinations of these methods may also be used to prepare the fusion proteins.

Methods of cloning and expressing proteins are well-known in the art, detailed descriptions of techniques and systems for the expression of recombinant proteins can be found, for example, in Current Protocols in Protein Science (Coligan, J. E., et al., Wiley & Sons, New York). Those skilled in the art will understand that a wide variety of expression systems can be used to provide the recombinant protein. Accordingly, the fusion proteins can be produced in a prokaryotic host (e.g., *E. coli, A. salmonicida* or *B. subtilis*) or in a eukaryotic host (e.g., *Saccharomyces* or *Pichia*; mammalian cells, e.g., COS, NIH 3T3, CHO, BHK, 293, or HeLa cells; or insect cells (baculovirus)). The fusion proteins can be purified from the host cells using standard techniques known in the art.

Sequences for various exemplary fusion proteins are provided in Table 1. Variants and homologs of these sequences can be cloned, if an alternative sequence is desired, using standard techniques (see, for example, Ausubel et al., Current Protocols in Molecular Biology, Wiley & Sons, NY (1997 and updates); Sambrook et al., Sambrook, et al. Molecular Cloning: A Laboratory Manual. $2^{nd}$ ed., Cold Spring Harbor Laboratory, Cold Spring Harbor Laboratory Press, Cold Spring Harbor, N.Y., 1989 or updates thereto). For example, the nucleic acid sequence can be obtained directly from a suitable organism, such as *Aeromonas hydrophila*, by extracting mRNA and then synthesizing cDNA from the mRNA template (for example by RT-PCR) or by PCR-amplifying the gene from genomic DNA. Alternatively, the nucleic acid sequence encoding either the IL-4R binding moiety or the pro-apoptotic Bcl-2 family moiety can be obtained from an appropriate cDNA library by standard procedures. The isolated cDNA is then inserted into a suitable vector, such as a cloning vector or an expression vector.

Mutations (if desired) can be introduced at specific, pre-selected locations by in vitro site-directed mutagenesis techniques well-known in the art. Mutations can be introduced by deletion, insertion, substitution, inversion, or a combination thereof, of one or more of the appropriate nucleotides making up the coding sequence.

The expression vector can further include regulatory elements, such as transcriptional elements, required for efficient transcription of the fusion protein-encoding sequences. Examples of regulatory elements that can be incorporated into the vector include, but are not limited to, promoters, enhancers, terminators, and polyadenylation signals. Vectors that include a regulatory element operatively linked to a nucleic acid sequence encoding a genetically engineered fusion protein can be used to produce the fusion protein.

The expression vector may additionally contain heterologous nucleic acid sequences that facilitate the purification of the expressed fusion protein, such as affinity tags such (e.g., metal-affinity tags, histidine tags, avidin/streptavidin encoding sequences, glutathione-S-transferase (GST) encoding sequences, maltose binding protein (MBP) encoding sequences or biotin encoding sequences). In one example, such tags are attached to the N- or C-terminus of a fusion protein, or can be located within the fusion protein. The tags can be removed from the expressed fusion protein prior to use according to methods known in the art. Alternatively, the tags can be retained on the fusion protein, providing that they do not interfere with the ability of the desired activity of the fusion protein.

The fusion protein can include one or more linkers, as well as other moieties, as desired and/or as discussed herein. These can include a binding region, such as avidin or an epitope, or a tag such as a polyhistidine tag, which can be useful for purification and processing of the fusion protein, as well as other linkers as described herein. In addition, detectable markers can be attached to the fusion protein, so that the traffic of the fusion protein through a body or cell can be monitored conveniently. Such markers include radionuclides, enzymes, fluorophores, chromophores, and the like.

One of ordinary skill in the art will appreciate that the DNA can be altered in numerous ways without affecting the biological activity of the encoded protein. For example, PCR can be used to produce variations in the DNA sequence which encodes a fusion protein. Such variations in the DNA sequence encoding a fusion protein can be used to optimize for codon preference in a host cell used to express the protein, or may contain other sequence changes that facilitate expression.

A covalent linkage of an IL-4R binding protein directly to a pro-apoptotic Bcl-2 family member or via a linker may take various forms as is known in the art. For example, the covalent linkage may be in the form of a disulfide bond. The DNA encoding one of the components can be engineered to contain a unique cysteine codon. The second component can be derivatized with a sulfhydryl group reactive with the cysteine of the first component. Alternatively, a sulfhydryl group, either by itself or as part of a cysteine residue, can be introduced using solid phase polypeptide techniques. For example, the introduction of sulfhydryl groups into peptides is described by Hiskey (Peptides 3:137, 1981).

Assays

Fusion proteins can be assayed using standard techniques known in the art or described herein.

For example, the ability of the fusion proteins to kill or inhibit growth of cells can be assayed in vitro using suitable cells, typically a cell line expressing the target or a cancer cell. In general, cells of the selected test cell line are grown to an appropriate density and the candidate fusion protein is added. The fusion protein can be added to the culture at around at least 1 ng/mL, at least 1 ug/mL, or at least 1 mg/mL, such as from about 0.01 ug/mL to about 1 mg/mL, from about 0.10 ug/mL to about 0.5 mg/mL, from about 1 ug/mL to about 0.4 mg/mL. In some examples, serial dilutions are tested. After an appropriate incubation time (for example, about 48 to 72 hours), cell survival or growth is assessed. Methods of determining cell survival are well known in the art and include, but are not limited to, the resazurin reduction test (see Fields & Lancaster Am. Biotechnol. Lab., 11:48-50, 1993; O'Brien et al., Eur. J. Biochem., 267:5421-5426, 2000 or U.S. Pat. No. 5,501,959), the sulforhodamine assay (Rubinstein et al., J. Natl. Cancer Inst., 82:113-118, 1999) or the neutral red dye test (Kitano et al., Euro. J. Clin. Investg., 21:53-58, 1991; West et al., J. Investigative Derm., 99:95-100, 1992) or trypan blue assay. Numerous commercially available kits may also be used, for example the CellTiter 96®AQueous One Solution Cell Proliferation Assay (Promega). Cytotoxicity is determined by comparison of cell survival in the treated culture with cell survival in one or more control cultures, for example, untreated cultures and/or cultures pre-treated with a control compound (typically a known therapeutic), or other appropriate control.

Additional assays are described in, for example, Crouch et al. (J. Immunol. Meth. 160, 81-8); Kangas et al. (Med. Biol. 62, 338-43, 1984); Lundin et al., (Meth. Enzymol. 133, 27-42, 1986); Petty et al. (Comparison of J. Biolum. Chemilum. 10, 29-34, 1995); and Cree et al. (AntiCancer Drugs 6: 398-404, 1995). Cell viability can be assayed using a variety of methods, including MTT (3-(4,5-dimethylthiazolyl)-2,5-diphenyltetrazolium bromide) (Barltrop, Bioorg. & Med. Chem. Lett. 1: 611, 1991; Cory et al., Cancer Comm. 3, 207-12, 1991; Paull J. Heterocyclic Chem. 25, 911, 1988). Assays for cell viability are also available commercially.

These assays include but are not limited to CELLTITER-GLO® Luminescent Cell Viability Assay (Promega), which uses luciferase technology to detect ATP and quantify the health or number of cells in culture, and the CellTiter-Glo® Luminescent Cell Viability Assay, which is a lactate dehydrogenase (LDH) cytotoxicity assay (Promega).

Fusion proteins that confer selectivity for a specific type of cancer may be tested for their ability to target that specific cancer cell type. For example, a fusion protein comprising a specific IL-4 that targets cells displaying IL-4R Type I or Type II can be assessed for its ability to selectively target such cells by comparing the ability of the fusion protein to kill cancer cells to its ability to kill a normal cell, or a different type of cancer cell (e.g., one that does not express IL-4R Type I or Type II). Alternatively, flow cytometric methods, as are known in the art, may be used to determine if a fusion protein comprising a Type I or Type II receptor-specific IL-4 is able to selectively target a specific type of cell. Binding of a labeled antibody to the bound fusion protein will indicate binding of the fusion protein to the target.

Similarly, assays for measuring cell apoptosis are known in the art. Apoptotic cells are characterized by characteristic morphological changes, including chromatin condensation, cell shrinkage and membrane blebbing, which can be clearly observed using light microscopy. The biochemical features of apoptosis include DNA fragmentation, protein cleavage at specific locations, increased mitochondrial membrane permeability, and the appearance of phosphatidylserine on the cell membrane surface. Assays for apoptosis are known in the art. Exemplary assays include TUNEL (Terminal deoxynucleotidyl Transferase Biotin-dUTP Nick End Labeling) assays, caspase activity (specifically caspase-3) assays, and assays for fas-ligand and annexin V. Commercially available products for detecting apoptosis include, for example, Apo-ONE® Homogeneous Caspase-3/7 Assay, FragEL TUNEL kit (ONCOGENE RESEARCH PRODUCTS, San Diego, Calif.), the ApoBrdU DNA Fragmentation Assay (BIOVISION, Mountain View, Calif.), and the Quick Apoptotic DNA Ladder Detection Kit (BIOVISION, Mountain View, Calif.).

A variety of cell lines suitable for testing the candidate fusion proteins are known in the art and many are commercially available (for example, from the American Type Culture Collection, Manassas, Va.). Similarly, animal models are known in the art and many are commercially available.

Therapeutic Indications and Uses

The fusion proteins including IL-4R binding protein and a pro-apoptotic Bcl-2 family member, as described herein, can be used for a variety of therapeutic purposes. In general, the fusion proteins described herein can be used in the treatment or prophylaxis of any disease, disorder or condition which involves cells which express an IL-4R, and which would be benefited by inhibiting cell proliferation or enhancing cell death. In some embodiments, the fusion proteins described herein can be used in the treatment or prophylaxis of any disease, disorder or condition which involves cells which express a Type I or Type II IL-4R, and in which selection of one type of receptor over the other is useful, and which would be benefited by inhibiting cell proliferation or enhancing cell death.

In some embodiments, a fusion protein including a pro-apoptotic Bcl-2 family member can be used to induce apoptosis or cell death or to treat a disorder associated with abnormal apoptosis or cell proliferation, such as cancer. As used herein, the terms "cancer," "cancerous," "hyperproliferative," or "neoplastic" refer to cells having the capacity for autonomous growth (e.g., an abnormal state or condition characterized by rapidly proliferating cell growth). Hyperproliferative and neoplastic disease states may be categorized as pathologic (e.g., as a deviation from normal but not associated with a disease state). Accordingly, by a "cancer" or "neoplasm" is meant any unwanted growth of cells serving no physiological function. In general, a cell of a neoplasm has been released from its normal cell division control, i.e., a cell whose growth is not regulated by the ordinary biochemical and physical influences in the cellular environment. In most cases, a neoplastic cell proliferates to form a clone of cells which are either benign or malignant. Examples of cancers or neoplasms include, without limitation, transformed and immortalized cells, tumours, and carcinomas such as breast cell carcinomas and prostate carcinomas. The term cancer includes cell growths that are technically benign but which carry the risk of becoming malignant. By "malignancy" is meant an abnormal growth of any cell type or tissue. The term malignancy includes cell growths that are technically benign but which carry the risk of becoming malignant. This term also includes any cancer, carcinoma, neoplasm, neoplasia, or tumor. The terms are therefore meant to include all types of cancerous growths or oncogenic processes, metastatic tissue or malignantly transformed cells, tissues or organs, irrespective of histopathologic type or stage of invasiveness. In some embodiments, a fusion protein including a pro-apoptotic Bcl-2 family member is not used in connection with a cancer affecting a stem cell.

Most cancers fall within three broad histological classifications: carcinomas, which are the predominant cancers and are cancers of epithelial cells or cells covering the external or internal surfaces of organs, glands, or other body structures (e.g., skin, uterus, lung, breast, prostate, stomach, bowel), and which tend to metastasize; sarcomas, which are derived from connective or supportive tissue (e.g., bone, cartilage, tendons, ligaments, fat, muscle); and hematologic tumors, which are derived from bone marrow and lymphatic tissue. Examples of cancers include, without limitation, carcinomas, sarcomas, and hematopoietic neoplastic disorders e.g., leukemia.

Carcinomas may be adenocarcinomas (which generally develop in organs or glands capable of secretion, such as breast, lung, colon, prostate or bladder) or may be squamous cell carcinomas (which originate in the squamous epithelium and generally develop in most areas of the body).

Sarcomas may be osteosarcomas or osteogenic sarcomas (bone), chondrosarcomas (cartilage), leiomyosarcomas (smooth muscle), rhabdomyosarcomas (skeletal muscle), mesothelial sarcomas or mesotheliomas (membranous lining of body cavities), fibrosarcomas (fibrous tissue), angiosarcomas or hemangioendotheliomas (blood vessels), liposarcomas (adipose tissue), gliomas or astrocytomas (neurogenic connective tissue found in the brain), myxosarcomas (primitive embryonic connective tissue), or mesenchymous or mixed mesodermal tumors (mixed connective tissue types).

Hematopoietic neoplastic disorders include diseases involving hyperplastic/neoplastic cells of hematopoietic origin e.g., arising from myeloid, lymphoid or erythroid lineages or precursor cells thereof. Preferably, the diseases arise from poorly differentiated acute leukemias (e.g., erythroblastic leukemia and acute megakaryoblastic leukemia). Additional exemplary myeloid disorders include, but are not limited to, acute promyeloid leukemia (APML), acute myeloenous leukemia (AML) and chronic myeloenous leukemia (CML); lymphoid malignancies include but are not limited to acute lymphoblastic leukemia (ALL), which includes B-lineage ALL and T-lineage ALL, chronic lymphocytic leukemia (CLL), prolymphocytic leukemia (PLL), hairy cell leukemia, and Waldenstrom's macroglobulinemia.

Additional forms of malignant lymphomas include, but are not limited to non-Hodgkin lymphoma and variants thereof, peripheral T cell lymphomas, adult T cell leukemia/lymphoma (ATL), cutaneous T cell lymphoma (CTCL), large granular lymphocytic leukemia (LGF), Hodgkin's disease and Reed-Stemberg diseases.

Cancers may also be named based on the organ in which they originate i.e., the "primary site," for example, cancer of the breast, brain, lung, liver, skin, prostate, testicle, bladder, colon and rectum, cervix, uterus, etc. This naming persists even if the cancer metastasizes to another part of the body, that is different from the primary site. Cancers named based on primary site may be correlated with histological classifications. For example, lung cancers are generally small cell lung cancers or non-small cell lung cancers, which may be squamous cell carcinoma, adenocarcinoma, or large cell carcinoma; skin cancers are generally basal cell cancers, squamous cell cancers, or melanomas. Lymphomas may arise in the lymph nodes associated with the head, neck and chest, as well as in the abdominal lymph nodes or in the axillary or inguinal lymph nodes. Identification and classification of types and stages of cancers may be performed by using for example information provided by the Surveillance, Epidemiology, and End Results (SEER) Program of the National Cancer Institute.

In some embodiments, a fusion protein including a pro-apoptotic Bcl-2 family protein member, or a fragment thereof, can be used to treat cancers such as gastric carcinoma, invasive pituitary adenomas, biliary tract carcinoma, cervical cancer, lymphoma, melanoma, chronic lymphocytic leukemia, non-hodgkins lymphoma, follicular lymphoma, pancreatic cancer, colorectal cancer, colon cancer, thyroid cancer, liver cancer, ovarian cancer, prostate cancer, bladder cancer, renal cell carcinoma, mesothelioma, rhabdomyosarcoma, breast cancer, non-small cell lung cancer, head and neck cancers, or Kaposi's carcinoma.

In some embodiments, a fusion protein including a pro-apoptotic Bcl-2 family protein member, or a fragment thereof, can be used to treat CNS cancers such as gliomas, meningeal tumours, diffuse intrinsic pontine glioma, medulloblastoma, neuroblastoma, anaplastic astrocytoma, glioblastoma multiforme, metastatic brain cancer, or CNS lymphoma.

The fusion proteins can be used to treat, stabilize or prevent cancer. Fusion proteins can also be used in the treatment of indolent cancers, recurrent cancers including locally recurrent, distantly recurrent and/or refractory cancers (i.e. cancers that have not responded to other anticancer treatments), metastatic cancers, locally advanced cancers and aggressive cancers. In these contexts, the fusion proteins may exert either a cytotoxic or cytostatic effect resulting in, for example, a reduction in the number or growth of cancer cells, a reduction in the size of a tumor, the slowing or prevention of an increase in the size of a tumor, an increase in the disease-free survival time between the disappearance or removal of a tumor and its reappearance, prevention of an initial or subsequent occurrence of a tumor (e.g. metastasis), an increase in the time to progression, reduction of one or more adverse symptoms associated with a tumor, or an increase in the overall survival time of a subject having cancer.

Other examples of proliferative and/or differentiative disorders that can be treated using a fusion protein including a pro-apoptotic Bcl-2 family member include proliferative non-malignant diseases such as pulmonary fibrosis or hyperplasia (such as benign prostatic hyperplasia), cardiac fibrosis, or liver fibrosis; inflammatory conditions such as prostatitis, vernal keratoconjunctivitis, artherosclerosis, idiopathic pulmonary pneumonia; or autoimmune conditions such as Graves disease.

In some embodiments, a fusion protein including a pro-apoptotic Bcl-2 family protein member, or a fragment thereof, is capable of inhibiting cell survival, inhibiting cell proliferation, or enhancing cell death or apoptosis. In some embodiments, the IL-4R binding protein-pro-apoptotic Bcl-2 family fusion protein is capable of inhibiting cell survival, inhibiting cell proliferation, or enhancing cell death or apoptosis, when compared to a suitable control, such as IL-4 alone, IL-4 joined to a non-pro-apoptotic Bcl-2 family protein, etc. A suitable control may also include a previously-established standard. Accordingly, any test or assay for determining the activity or efficacy of an IL-4R binding protein-pro-apoptotic Bcl-2 family fusion protein may be compared to the established standard and it may not be necessary to include a control for comparison each time. By "inhibiting cell survival" is meant decreasing (e.g., by at least 10%, 20%, 30%, or by as much as 50%, 75%, 85% or 90% or more) the probability that a cell at risk of cell death will survive. By "inhibiting cell proliferation" is meant decreasing (e.g., by at least 10%, 20%, 30%, or by as much as 50%, 75%, 85% or 90% or more) the growth or proliferation of a cell. By "enhancing cell death or apoptosis" is meant increasing (e.g., by at least 10%, 20%, 30%, or by as much as 50%, 75%, 85% or 90% or more) the probability that a cell at risk of cell death will undergo apoptotic, necrotic, or any other form of cell death.

In some embodiments, a fusion protein including a pro-apoptotic Bcl-2 family protein member, or a fragment thereof, is capable of inhibiting cell survival, inhibiting cell proliferation, or enhancing cell death or apoptosis by at least 20%, 30%, or by as much as 50%, 75%, 85% or 90% or more, when compared to a cell cultured under similar conditions but not contacted with the fusion protein. Suitable assays for measuring the inhibition of cell survival, inhibition of cell proliferation, or enhancement of cell death or apoptosis are described herein or known in the art.

In some embodiments, the $IC_{50}$ of a fusion protein including a pro-apoptotic Bcl-2 family protein member, or a fragment thereof, in inhibiting cell survival, inhibiting cell proliferation, or enhancing cell death or apoptosis, can be in the range from about 0.1 ng/mL to about 10,000 ng/mL, or any value therebetween, such as about 0.5 ng/mL, 1 ng/mL, 5 ng/mL, 10 ng/mL, 25 ng/mL, 50 ng/mL, 75 ng/mL, 100 ng/mL, 150 ng/mL, 200 ng/mL, 250 ng/mL, 300 ng/mL, 350 ng/mL, 400 ng/mL, 450 ng/mL, 500 ng/mL, 550 ng/mL, 600 ng/mL, 650 ng/mL, 700 ng/mL, 750 ng/mL, 800 ng/mL, 850 ng/mL, 900 ng/mL, 950 ng/mL, or 1000 ng/mL.

"Target cells" include, without limitation, neurons, lymphocytes, stem cells, epithelial cells, cancer cells, neoplasm cells, immune cells, non-malignant cells of the tumour microenvironment, hyper-proliferative cells, etc. The target cell chosen will depend on the disease or injury or condition the fusion protein is intended to treat.

Pharmaceutical Compositions, Dosages and Administration

Pharmaceutical compositions according to the present disclosure can include one or more fusion proteins and one or more non-toxic, pharmaceutically-acceptable carriers, diluents, excipients and/or adjuvants. Such compositions can be suitable for use in treatment of therapeutic indications as described herein.

If desired, other active ingredients may be included in the compositions. Accordingly, in some embodiments, a fusion protein including a pro-apoptotic Bcl-2 family member can be administered in therapeutically-effective amounts together with one or more anti-cancer or other therapeutics. The fusion protein(s) can be administered before, during or after treatment with the anti-cancer or other therapeutic. An "anti-cancer therapeutic" is a compound, composition, or treatment (e.g., surgery) that prevents or delays the growth and/or metastasis of cancer cells. Such anti-cancer therapeutics include, but are not limited to, surgery (e.g., removal of all or part of a tumor), chemotherapeutic drug treatment, radiation, gene therapy, hormonal manipulation, immunotherapy (e.g., therapeutic antibodies and cancer vaccines) and antisense or RNAi oligonucleotide therapy. Examples of useful chemotherapeutic drugs include, but are not limited to, hydroxyurea, busulphan, cisplatin, carboplatin, chlorambucil, melphalan, cyclophosphamide, Ifosfamide, danorubicin, doxorubicin, epirubicin, mitoxantrone, vincristine, vinblastine, vinorelbine, etoposide, teniposide, paclitaxel, docetaxel, gemcitabine, cytosine, arabinoside, bleomycin, neocarcinostatin, suramin, taxol, mitomycin C, Avastin, Herceptin®, fluorouracil, temozolamide, etc. The fusion protein(s) are also suitable for use with standard combination therapies employing two or more chemotherapeutic agents. It is to be understood that anti-cancer therapeutics includes novel compounds or treatments developed in the future.

The fusion protein can also be administered in combination with a sensitizing agent, such as a radio-sensitizer (see for example Diehn et al., J. Natl. Cancer Inst. 98:1755-7, 2006). Generally a sensitizing agent is any agent that increases the activity of a fusion protein. For example, a sensitizing agent will increase the ability of a fusion protein to inhibit cancer cell growth or kill cancer cells. Exemplary sensitizing agents include antibodies to IL-10, bone morphogenic proteins and HDAC inhibitors (see for example Sakariassen et al., Neoplasia 9(11):882-92, 2007). These sensitizing agents can be administered before or during treatment with the fusion protein. Exemplary dosages of such sensitizing agents include at least 1 ug/mL, such as at least 10 ug/mL, at least 100 ug/mL, for example 5-100 ug/mL or 10-90 ug/mL. The sensitizing agents can be administered daily, three times a week, twice a week, once a week or once every two weeks. Sensitizing agents can also be administered after treatment with the fusion protein is finished.

The fusion proteins may be used as part of a neo-adjuvant therapy (to primary therapy), as part of an adjuvant therapy regimen, where the intention is to cure the cancer in a subject. The fusion proteins can also be administered at various stages in tumor development and progression, including in the treatment of advanced and/or aggressive neoplasias (e.g., overt disease in a subject that is not amenable to cure by local modalities of treatment, such as surgery or radiotherapy), metastatic disease, locally advanced disease and/or refractory tumors (e.g., a cancer or tumor that has not responded to treatment). "Primary therapy" refers to a first line of treatment upon the initial diagnosis of cancer in a subject. Exemplary primary therapies may involve surgery, a wide range of chemotherapies and radiotherapy. "Adjuvant therapy" refers to a therapy that follows a primary therapy and that is administered to subjects at risk of relapsing. Adjuvant systemic therapy is begun soon after primary therapy, for example 2, 3, 4, 5, or 6 weeks after the last primary therapy treatment to delay recurrence, prolong survival or cure a subject. As discussed herein, it is contemplated that the fusion proteins can be used alone or in combination with one or more other chemotherapeutic agents as part of an adjuvant therapy. Combinations of the fusion proteins and standard chemotherapeutics may act to improve the efficacy of the chemotherapeutic and, therefore, can be used to improve standard cancer therapies. This application can be particularly important in the treatment of drug-resistant cancers which are not responsive to standard treatment.

In cancer, the microenvironment of a tumor contains both malignant and non-malignant cells. The tumor microenvironment can be identified using one or more of the following criteria: (a) a region comprising non-malignant cells which share the same physiological environment, or which are directly adjacent to malignant cells; (b) the extended tumor region; (c) an area of inflammation surrounding or proximal to a tumor; (d) an area in which the number or rate of proliferation of regulatory T cells is elevated; and (e) an area in which tumor-associated macrophages, dendritic cells, myeloid-derived suppressor cells, Th2 cells or fibrocytes are elevated. Within the context of non-solid tumor types, the tumor microenvironment may also be determined by the local cell-cell interactions between malignant cells and between malignant cells and any adjacent or nearby non-malignant cells. Such interactions may include, for example, cell adhesion events and/or paracrine effects of soluble mediators produced by one cell (malignant or non-malignant) on another cell (malignant or non-malignant) in the tumor microenvironment.

The non-malignant cells in the tumor microenvironment can be important for tumor initiation and progression (Reynolds et al., Cancer Res., 1996, 56(24):5754-5757). The non-malignant cells, also called stromal cells, occupy or accumulate in the same cellular space as malignant cells, or the cellular space adjacent or proximal to malignant cells, which modulate tumor cell growth or survival. For example, non-malignant cells that normally function to support inflammatory and immune response can be capable of contributing to tumor initiation or progression. Accordingly, in alternative embodiments, a fusion protein including a pro-apoptotic Bcl-2 family member can be used for inhibiting cell survival, inhibiting cell proliferation, or enhancing cell death or apoptosis of a non-malignant cell that expresses a Type I or Type II IL-4R in a tumour microenvironment. Such non-malignant cells can be immunoregulatory or inflammatory cells such as antigen presenting cells (e.g., macrophages, dendritic cells, B cells) or myeloid-derived suppressor cells (e.g., myeloid-derived monocytes and tie-2-expressing monocytes) present within the tumor microenvironment, and inhibition of T cell subsets that function to support tumor progression (e.g., regulatory T cells and Th2 helper cells) and/or suppressing production of one or more inflammatory cytokines in a tumor microenvironment. Among the non-malignant cells of a tumor microenvironment are regulatory T cells, which are observed in higher frequencies in a number of tumors, including Hodgkin's lymphoma, non-Hodgkin's lymphoma (Shi et al., Ai Zheng., 2004, 23(5):597-601 (abstract only)), malignant melanoma (Viguier et al., J. Immunol., 2004, 173(2):1444-53; Javia et al., J. Immunother., 2003, 26(1):85-93), and cancers of the ovary (Woo et al., Cancer Res., 2001, 61(12):4766-72), gastrointestinal tract (Ichihara et al., Clin Cancer Res., 2003, 9(12):4404-4408; Sasada et al., Cancer, 2003, 98(5): 1089-1099), breast (Liyanage et al., J Immunol., 2002, 169(5):

2756-2761), lung (Woo et al., Cancer Res., 2001, 61(12): 4766-72), and pancreas (Liyanage et al., J Immunol., 2002, 169(5):2756-2761). The regulatory T cells are recruited to the tumor site in response to chemokines secreted by the tumor cells. See e.g., Curiel et al., Nat. Med., 2004, 10:942-949. An increase in the number of regulatory T cells may also correlate with poor prognosis (Curiel et al., Nat. Med., 2004, 10:942-949; Sasada et al., Cancer, 2003, 98:1089-1099). Conversely, regulatory T cells are observed to decrease following chemotherapy (Beyer et al., Blood, 2005, 106:2018-2025). The tumour micro-environment can also have a higher proportion of Th2 cells, when compared to Th1 cells, which is associated with poor prognosis and survival. In alternative embodiments, a fusion protein including a pro-apoptotic Bcl-2 family member according to the invention, such as cpIL-4-Bad, is useful for restoring the Th1>>Th2 balance by, for example, depleting Th2 cells. In some embodiments, a fusion protein including a pro-apoptotic Bcl-2 family member according to the invention, such as cpIL-4-Bad, may be administered to a subject prior to, or during, chemotherapy, radiation therapy, immunotherapy, etc. to disable or downregulate the tumor microenvironment.

Non-malignant cells can also be fibroblasts, myofibroblasts, glial cells, epithelial cells, adipocytes, vascular cells (including blood and lymphatic vascular endothelial cells and pericytes), resident and/or recruited inflammatory and immune (e.g., macrophages, dendritic cells, myeloid suppressor cells, granulocytes, lymphocytes, etc.), resident and/or recruited cells that are capable of giving rise to or differentiating into any of the above-noted non-malignant cells, and any functionally distinct subtypes of the above-noted cells as known in the art.

A "subject" can be a mammal in need of treatment, such as a human or veterinary patient (e.g., rodent, such as a mouse or rat, a cat, dog, cow, horse, sheep, goat, or other livestock). In some embodiments, a "subject" may be a clinical patient, a clinical trial volunteer, an experimental animal, etc. The subject may be suspected of having or at risk for having a condition characterized by cell proliferation, be diagnosed with a condition characterized by cell proliferation, or be a control subject that is confirmed to not have a condition characterized by cell proliferation, as described herein. Diagnostic methods for conditions characterized by cell proliferation and the clinical delineation of such diagnoses are known to those of ordinary skill in the art.

The composition can be a liquid solution, suspension, emulsion, sustained release formulation, or powder, and can be formulated with a pharmaceutically acceptable carrier. The composition can be formulated as a suppository, with traditional binders and carriers such as triglycerides. The term "pharmaceutically-acceptable carrier" refers to a carrier medium or vehicle which does not interfere with the effectiveness of the biological activity of the active ingredients and which is not toxic to the host or subject.

Fusion proteins can be delivered along with a pharmaceutically-acceptable vehicle. In one example, the vehicle may enhance the stability and/or delivery properties. Thus, the disclosure also provides for formulation of the fusion protein with a suitable vehicle, such as an artificial membrane vesicle (including a liposome, noisome, nanosome and the like), microparticle or microcapsule, or as a colloidal formulation that comprises a pharmaceutically acceptable polymer. The use of such vehicles/polymers may be beneficial in achieving sustained release of the fusion proteins. Alternatively, or in addition, the fusion protein formulations can include additives to stabilize the protein in vivo, such as human serum albumin, or other stabilizers for protein therapeutics known in the art. Fusion protein formulations can also include one or more viscosity enhancing agents which act to prevent backflow of the formulation when it is administered, for example by injection or via catheter. Such viscosity enhancing agents include, but are not limited to, biocompatible glycols and sucrose.

Pharmaceutical compositions containing one or more fusion proteins can be formulated as a sterile injectable aqueous or oleaginous suspension according to methods known in the art and using suitable one or more dispersing or wetting agents and/or suspending agents, such as those mentioned above. The sterile injectable preparation can be a sterile injectable solution or suspension in a non-toxic parentally acceptable diluent or solvent, for example, as a solution in 1,3-butanediol. Acceptable vehicles and solvents that can be employed include, but are not limited to, water, Ringer's solution, lactated Ringer's solution and isotonic sodium chloride solution. Other examples include, sterile, fixed oils, which are conventionally employed as a solvent or suspending medium, and a variety of bland fixed oils including, for example, synthetic mono- or diglycerides. Fatty acids such as oleic acid can also be used in the preparation of injectables.

In some embodiments, the fusion protein is conjugated to a water-soluble polymer, e.g., to increase stability or circulating half life or reduce immunogenicity. Clinically acceptable, water-soluble polymers include, but are not limited to, polyethylene glycol (PEG), polyethylene glycol propionaldehyde, carboxymethylcellulose, dextran, polyvinyl alcohol (PVA), polyvinylpyrrolidone (PVP), polypropylene glycol homopolymers (PPG), polyoxyethylated polyols (POG) (e.g., glycerol) and other polyoxyethylated polyols, polyoxyethylated sorbitol, or polyoxyethylated glucose, and other carbohydrate polymers. Methods for conjugating polypeptides to water-soluble polymers such as PEG are described, e.g., in U.S. patent Pub. No. 20050106148 and references cited therein. In one example the polymer is a pH-sensitive polymers designed to enhance the release of drugs from the acidic endosomal compartment to the cytoplasm (see for example, Henry et al., Biomacromolecules 7(8):2407-14, 2006).

Typically vaccines are prepared in an injectable form, either as a liquid solution or as a suspension. Solid forms suitable for injection may also be prepared as emulsions, or with the polypeptides encapsulated in liposomes. The cells are injected in any suitable carrier known in the art. Suitable carriers typically comprise large macromolecules that are slowly metabolized, such as proteins, polysaccharides, polylactic acids, polyglycolic acids, polymeric amino acids, amino acid copolymers, lipid aggregates, and inactive virus particles. Such carriers are well known to those skilled in the art. These carriers may also function as adjuvants.

Adjuvants are immunostimulating agents that enhance vaccine effectiveness. Effective adjuvants include, but are not limited to, aluminum salts such as aluminum hydroxide and aluminum phosphate, muramyl peptides, bacterial cell wall components, saponin adjuvants, and other substances that act as immunostimulating agents to enhance the effectiveness of the composition.

Vaccines are administered in a manner compatible with the dose formulation. By an effective amount is meant a single dose, or a vaccine administered in a multiple dose schedule, that is effective for the treatment or prevention of a disease or disorder. Preferably, the dose is effective to inhibit the growth of a neoplasm. The dose administered will vary, depending on the subject to be treated, the subject's health and physical condition, the capacity of the subject's immune system to produce antibodies, the degree of protection desired, and other relevant factors. Precise amounts of the active ingredient required will depend on the judgement of the practitioner.

The pharmaceutical compositions described herein include one or more fusion proteins in an amount effective to achieve the intended purpose. Typically, compositions including a fusion protein containing a pro-apoptotic Bcl-2 family member are administered to a patient already suffering from a disease, disorder or condition characterized by cell proliferation, or at risk for such a disease, disorder or condition, in an amount sufficient to cure or at least partially arrest a symptom associated with cell proliferation or reduce cell growth.

The skilled person will therefore recognize that the dosage to be administered is not subject to defined limits. Prior to administration for therapeutic purposes, the dosage of the fusion protein may need to be modified or adapted for the particular purpose, for example the concentration of fusion protein needed for whole body administration may differ from that used for local administration. Similarly, the toxicity of the therapeutic may change depending upon the mode of administration and overall composition being used (e.g., buffer, diluent, additional chemotherapeutic, etc.).

An "effective amount" of a pharmaceutical composition according to the invention includes a therapeutically effective amount or a prophylactically effective amount. A "therapeutically effective amount" refers to an amount of the fusion protein effective, at dosages and for periods of time necessary, that ameliorates the symptoms of the disease, disorder or condition to be treated. A therapeutically effective amount of a compound may vary according to factors such as the disease state, age, sex, and weight of the subject, and the ability of the compound to elicit a desired response in the subject. Dosage regimens may be adjusted to provide the optimum therapeutic response. A therapeutically effective amount is also one in which any toxic or detrimental effects of the fusion protein are outweighed by the therapeutically beneficial effects. Determination of a therapeutically effective dose of a compound is well within the capability of those skilled in the art. For example, the therapeutically effective dose can be estimated initially either in cell culture assays, or in animal models, such as those described herein. A "prophylactically effective amount" refers to an amount of the fusion protein effective, at dosages and for periods of time necessary, that achieves the desired prophylactic result, such as delay in onset of symptoms of a neurological disorder or continued remission of a cancer. Animal models can also be used to determine the appropriate concentration range and route of administration. Such information can then be used to determine useful doses and routes for administration in other animals, including humans, using standard methods known in those of ordinary skill in the art.

Concentration of the fusion protein in the final formulation can be at least 0.1 mg/mL, such as at least 1 ng/mL or at least 1 ug/mL or at least 1 mg/mL. For example, the concentration in the final formulation can be between about 0.01 ug/mL and about 1,000 ug/mL. In one example, the concentration in the final formulation is between about 0.01 mg/mL and about 100 mg/mL.

In some embodiments, a fusion protein including an anti-apoptotic Bcl-2 family protein, or fragment thereof, is administered at concentrations ranging from about 10 ng/mL to about 10,000 ng/mL, or any value therebetween, such as about 25 ng/mL, 50 ng/mL, 75 ng/mL, 100 ng/mL, 150 ng/mL, 200 ng/mL, 250 ng/mL, 300 ng/mL, 350 ng/mL, 400 ng/mL, 450 ng/mL, 500 ng/mL, 550 ng/mL, 600 ng/mL, 650 ng/mL, 700 ng/mL, 750 ng/mL, 800 ng/mL, 850 ng/mL, 900 ng/mL, 950 ng/mL, 1000 ng/mL, 1500 ng/mL, 2000 ng/mL, 2500 ng/mL, 3000 ng/mL, 3500 ng/mL, 4000 ng/mL, 4500 ng/mL, 5000 ng/mL, 5500 ng/mL, 6000 ng/mL, 6500 ng/mL, 7000 ng/mL, 7500 ng/mL, 8000 ng/mL, 8500 ng/mL, 9000 ng/mL, 9500 ng/mL, or 10000 ng/mL.

In some embodiments, a fusion protein including an pro-apoptotic Bcl-2 family protein, or fragment thereof, is administered at concentrations ranging from about 0.1 ng/mL to about 10,000 ng/mL However, it will be understood that the actual amount of the compound(s) to be administered will be determined by a physician, in the light of the relevant circumstances, including the condition to be treated, the chosen route of administration, the actual compound administered, the age, weight, and response of the individual patient, and the severity of the patient's symptoms. The above dosage range is given by way of example only and is not intended to limit the scope in any way. In some instances dosage levels below the lower limit of the aforesaid range may be more than adequate, while in other cases still larger doses may be employed without causing harmful side effects, for example, by first dividing the larger dose into several smaller doses for administration throughout the day.

One of ordinary skill in the art will appreciate that the dosage will depend, among other things, upon the type of fusion protein being used and the type of disorder or condition being treated.

In general, the fusion proteins according to the present disclosure contain substantially human sequences and are therefore less antigenic than, for example, immunotoxins or other molecules that contain non-human sequences. In some embodiments, the fusion proteins according to the present disclosure contain at least 80%, for example, 80%, 85%, 90%, 95%, 96%, 97%, 98%, 99% or 100% human sequences. In some embodiments, the fusion proteins according to the present disclosure can be administered at substantially lower doses than for example, immunotoxins, or native IL-4R binding protein, such as IL-4 or IL-13.

In some embodiments, the fusion proteins may elicit some level of antibody response when administered to a subject, which in some cases may lead to undesirable side effects. Therefore, if necessary, the antigenicity of the fusion proteins can be assessed as known in the art and/or described herein. For example, in vivo toxic effects of the fusion proteins can be evaluated by measuring their effect on animal body weight during treatment and by performing hematological profiles and liver enzyme analysis after the animal has been killed. The general toxicity of the fusion proteins can be tested according to methods known in the art. For example, the overall systemic toxicity of the fusion proteins can be tested by determining the dose that kills 100% of mice (i.e. $LD_{100}$) or kills 50% of mice (i.e. $LD_{50}$) following a single intravenous injection. Doses that are at least about 2, 5, or 10-fold less than the $LD_{100}$ or $LD_{50}$ can be selected for administration into other mammals, such as a human.

The kinetics and magnitude of the antibody response to the fusion proteins described herein can be determined, for example, in immunocompetent mice and can be used to facilitate the development of a dosing regimen that can be used in an immunocompetent human. Immunocompetent mice such as the strain C57-BL6 are administered intravenous doses of fusion protein. The mice are killed at varying intervals (e.g. following single dose, following multiple doses) and serum obtained. An ELISA-based assay can be used to detect the presence of anti-fusion protein antibodies.

Serum samples from mice can be assessed for the presence of anti-fusion protein antibodies as known in the art. As another example, epitope mapping can also be used to determine antigenicity of proteins as described in Stickler, et al., J. Immunotherapy, 23:654-660, 2000. Briefly, immune cells known as dendritic cells and CD4+ T cells are isolated from the blood of community donors who have not been exposed to the protein of interest. Small synthetic peptides spanning the length of the protein are then added to the cells in culture. Proliferation in response to the presence of a particular peptide suggests that a T cell epitope is encompassed in the sequence. This peptide sequence can subsequently be deleted or modified in the fusion protein thereby reducing its antigenicity.

Therapeutic efficacy and toxicity can also be determined by standard pharmaceutical procedures such as, for example, by determination of the median effective dose, or $ED_{50}$ (i.e. the dose therapeutically effective in 50% of the population) and the median lethal dose, or $LD_{50}$ (i.e. the dose lethal to 50% of the population). The dose ratio between therapeutic and toxic effects is known as the "therapeutic index," which can be expressed as the ratio, $LD_{50}/ED_{50}$. The data obtained from cell culture assays and animal studies can be used to formulate a range of dosage for human or animal use. The dosage contained in such compositions is usually within a range of concentrations that include the $ED_{50}$ and demonstrate little or no toxicity. The dosage varies within this range depending upon the dosage form employed, sensitivity of the subject, and the route of administration and the like.

Administration of the fusion proteins can be intralesionally, for instance by direct injection directly into the apoptotic tissue site; into a site that requires cell growth; into a site where a cell, tissue or organ is at risk of cell death; or into a site of hyperproliferation or into a tumor. Alternatively, the fusion protein can be administered systemically. For methods of combination therapy comprising administration of a fusion protein in combination with a chemotherapeutic agent, the order in which the compositions are administered is interchangeable. Concomitant administration is also envisioned.

Typically in the treatment of cancer, fusion proteins are administered systemically to patients, for example, by bolus injection or continuous infusion into a patient's bloodstream. Alternatively, the fusion proteins may be administered locally, at the site of a tumor (intratumorally). When a fusion protein is administered intratumorally, the administration can be via any route, e.g., locally, regionally, focally, systemic, convection enhanced delivery or combinations thereof.

When used in conjunction with one or more known chemotherapeutic agents, the compounds can be administered prior to, or after, administration of the chemotherapeutic agents, or they can be administered concomitantly. The one or more chemotherapeutics may be administered systemically, for example, by bolus injection or continuous infusion, or they may be administered orally.

For administration to an animal, the pharmaceutical compositions can be formulated for administration by a variety of routes. For example, the compositions can be formulated for topical, rectal or parenteral administration or for administration by inhalation or spray. The term parenteral as used herein includes subcutaneous injections, intravenous, intramuscular, intrathecal, intrasternal injection or infusion techniques. Direct injection or infusion into a tumor is also contemplated. Convection enhanced delivery can also be used to administer the fusion protein.

In one example, the fusion protein can be injected into a subject having cancer, using an administration approach similar to the multiple injection approach of brachytherapy. For example, multiple aliquots of the purified fusion protein in the form of a pharmaceutical composition or formulation and in the appropriate dosage units, may be injected using a needle. Alternative methods of administration of the fusion proteins will be evident to one of ordinary skill in the art. Such methods include, for example, the use of catheters, or implantable pumps to provide continuous infusion of the fusion protein to the subject in need of therapy.

As is known in the art, software planning programs can be used in combination with brachytherapy treatment and ultrasound, for example, for placement of catheters for infusing fusion proteins to treat, for example, brain tumors or other localized tumors. For example, the positioning and placement of the needle can generally be achieved under ultrasound guidance. The total volume, and therefore the number of injections and deposits administered to a patient, can be adjusted, for example, according to the volume or area of the organ to be treated. An example of a suitable software planning program is the brachytherapy treatment planning program Variseed 7.1 (Varian Medical Systems, Palo Alto, Calif.) or iPlan (BrainLab, Munich, Germany) for convection enhanced delivery to the brain. Such approaches have been successfully implemented in the treatment of prostate cancer and brain cancer among others.

Fusion proteins can be used in inhibiting cell survival or inhibiting cell proliferation in the central nervous system (CNS). When the site of delivery is the brain, the fusion protein must be capable of being delivered to the brain. The blood-brain barrier limits the uptake of many therapeutic agents into the brain and spinal cord from the general circulation. Molecules which cross the blood-brain barrier use two main mechanisms: free diffusion and facilitated transport. Because of the presence of the blood-brain barrier, attaining beneficial concentrations of a given fusion protein in the CNS may require the use of specific drug delivery strategies. Delivery of fusion proteins to the CNS can be achieved by several methods.

One method relies on neurosurgical techniques. For instance, fusion proteins can be delivered by direct physical introduction into the CNS, such as intraventricular, intralesional, or intrathecal injection. Intraventricular injection can be facilitated by an intraventricular catheter, for example, attached to a reservoir, such as an Ommaya reservoir. Methods of introduction are also provided by rechargeable or biodegradable devices. Another approach is the disruption of the blood-brain barrier by substances which increase the permeability of the blood-brain barrier. Examples include intra-arterial infusion of poorly diffusible agents such as mannitol, pharmaceuticals which increase cerebrovascular permeability such as etoposide, or vasoactive agents, such as leukotrienes or by convention enhanced delivery by catheter (CED). Further, it may be desirable to administer the compositions locally to the area in need of treatment; this can be achieved, for example, by local infusion during surgery, by injection, by means of a catheter, or by means of an implant, the implant being of a porous, non-porous, or gelatinous material, including membranes, such as silastic membranes, or fibers. A suitable membrane is Gliadel® (Eisai Inc.).

Non-viral approaches can also be employed for the introduction of a therapeutic to a cell requiring modulation of cell death (e.g., a cell of a patient). For example, a nucleic acid molecule can be introduced into a cell by administering the nucleic acid molecule in the presence of lipofection (Feigner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by micro-injection under surgical conditions (Wolff et al., Science 247:1465, 1990). Preferably the nucleic acids are administered in combination with a liposome and protamine.

Gene transfer can also be achieved using non-viral means involving transfection in vitro. Such methods include the use of calcium phosphate, DEAE dextran, electroporation, and protoplast fusion. Liposomes can also be potentially beneficial for delivery of DNA into a cell. Transplantation of a fusion protein into the affected tissues of a patient can also be accomplished by transferring a normal nucleic acid into a cultivatable cell type ex vivo (e.g., an autologous or heterologous primary cell or progeny thereof), after which the cell (or its descendants) are injected into a targeted tissue.

cDNA expression for use in polynucleotide therapy methods can be directed from any suitable promoter (e.g., the human cytomegalovirus (CMV), simian virus 40 (SV40), or metallothionein promoters), and regulated by any appropriate mammalian regulatory element. For example, if desired, enhancers known to preferentially direct gene expression in specific cell types can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

The present invention will be further illustrated in the following examples.

EXAMPLES

Example 1

This example describes making circularly permuted IL-4 proteins.

Figure 5:
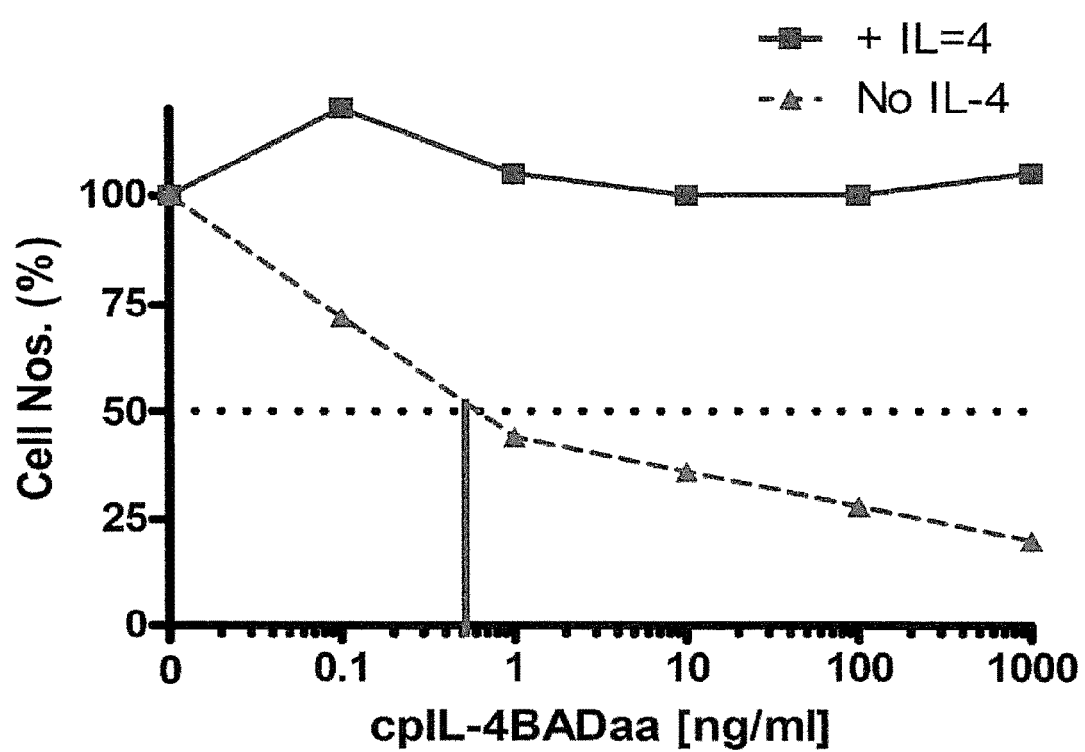

The coding sequence of IL-4 is designed to be reorganized creating a new amino terminus and a new carboxy terminus. The site of reorganization is selected and coding regions are developed synthetically or using the native sequence as a template. PCR can be used to amplify the separate coding regions and the 5' and 3' ends of the separate fragments are designed to overlap, thus allowing for the formation of a new coding sequence in which the newly generated peptide can for example encode a first amino acid that in the native protein may have been the 40$^{th}$ amino acid. Specific examples of making circularly permuted ligands are provided in U.S. Pat. No. 6,011,002.

The following sequence is used as a reference.

| Name | IL-4 | Linker | Toxin | Description |
|---|---|---|---|---|
| cpIL4-PE | MDTTEKETFCRAAT VLRQFYSHHEKDT RCLGATAQQFHRH KQURFLKRLDRNL WGLAGLNSCPVKE ANQSTLENFLERLK TIMREKYSKCSS***GG*** *NGG*HKCDITLQEIIK TLNSLTEQKTLCTE LTVTDIFAASK (SEQ ID NO: 2). | ASGGPE (SEQ ID NO: 29) | PE38KDEL | Circularly permuted human IL-4 fused to a *Pseudomonas* exotoxin (PE38KDEL) via a ASGGPE linker |

Example 2 cpIL-4-BAD was prepared using standard techniques and tested on IL-4Rα-expressing cancer cells in vitro and on IL-4Rα positive xenograft tumors in an athymic nude mouse model, using cpIL4-PE as a reference. The results indicated that cpIL-4-BAD was effective at killing the cancer cells and at regressing the tumors.

More specifically, cpIL-4-BAD fusion protein was prepared by transducing BL21(DE3)pLysS bacteria with chimeric plasmid cpIL-4BAD in a pET 24a expression vector (FIG. 1). The freshly transformed bacteria were plated on LB with kanamycin. Colonies were picked and transferred into 1 liter of superbroth enriched with glucose, $MgCl_2$ and kanamycin and the cells were induced with 1 mM IPTG. The growth of the cells was monitored for 6 hours. IL-4-BAD fusion proteins were refolded and purified using a HiTrap Column followed by two rounds of a MonoS column, after which cpIL-4-BAD fractions were evaluated by SDS-PAGE electrophoresis. This strategy yielded about 0.980 mg/L cpIL-4BAD at pH 6.5, and about 2.930 mg/L cpIL-4BAD at pH 6.8.

IL-4Rα positive tumor cells (U 251 cells and Daudi cells) were plated in quadruplicate in 6-well petri-dishes overnight in complete medium. 0.1-1000 ng/mL of cpIL-4BAD was added and the plates were incubated for five days in a $CO_2$ incubator at 37° C. On day 5, the plates were washed with 1×PBS and the cells were detached with trypsin treatment. After trypsin inactivation, viable cells were counted using the trypan blue exclusion technique.

The results indicated that the cpIL-4BAD fusion protein killed U 251 cells in a concentration dependent manner in vitro, with an $IC_{50}$ value of about 0.6 ng/mL (FIG. 2). 100× excess of IL-4 blocked the ability of cpIL-4BAD to kill the U 251 cells, demonstrating that the cpIL-4BAD activity was specific (FIG. 3). Also, the $IC_{50}$ value rose from about 0.3 ng/mL to >1000 ng/mL in 5-day cell viability assays.

The cpIL-4BAD fusion protein killed Daudi cells in a concentration-dependant manner in vitro, with an $IC_{50}$ value of about 0.1 ng/mL (FIG. 4). 100× excess of IL-4 also blocked the ability of cpIL-4BAD to kill the Daudi cells, demonstrating that the cpIL-4BAD activity was specific (FIG. 5). The IC$_{50}$ value rose from about 0.3 ng/mL to >1000 ng/mL in 5-day cell viability assays.

Figure 6:
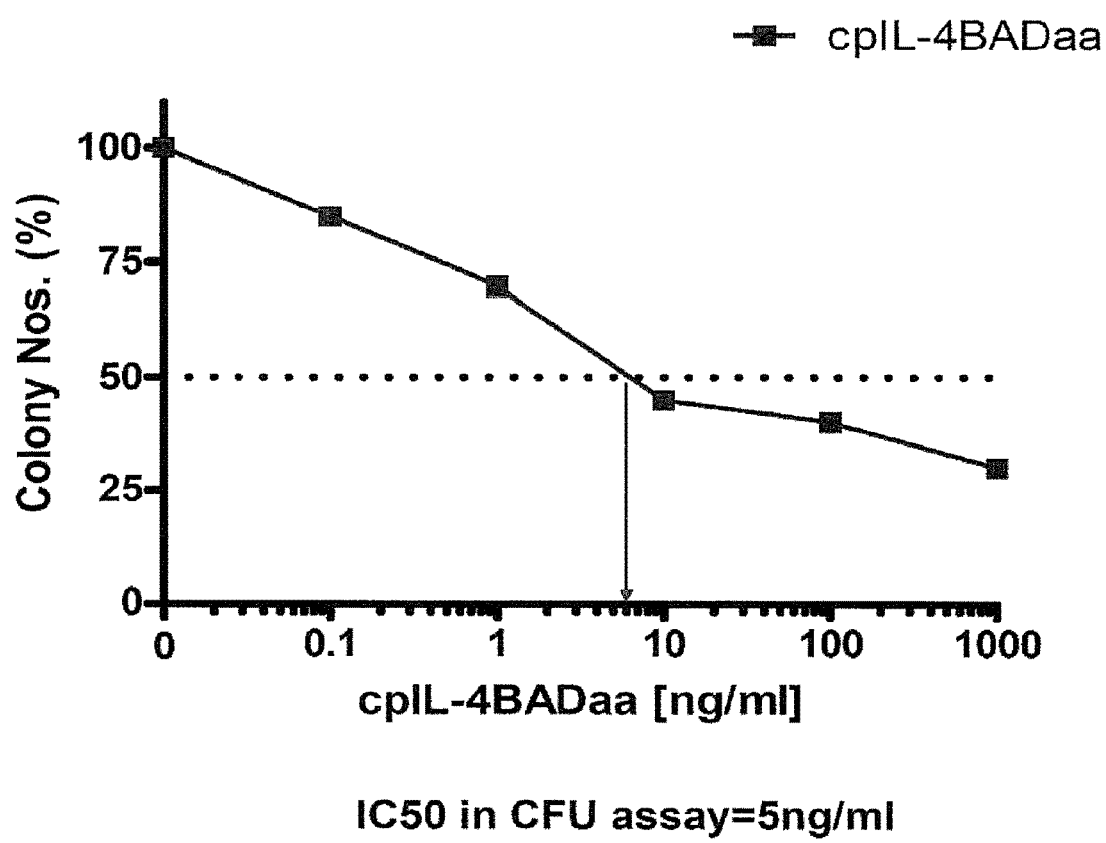

The cpIL-4BAD fusion protein was also found to decrease the colony numbers of IL-4Rα positive tumor cells in a colony formation assay. More specifically, 5000 U 251 cells were plated in 10 cm culture plates (6 plates in total), cpIL-4BAD was added and the cells were incubated for 10 days. Colonies were stained with Crystal Blue and counted. The results indicated that cpIL-4BAD decreased U 251 colony numbers in a concentration dependent manner in vitro, with an IC$_{50}$ value of about 5 ng/mL (FIG. 6).

Figure 7:
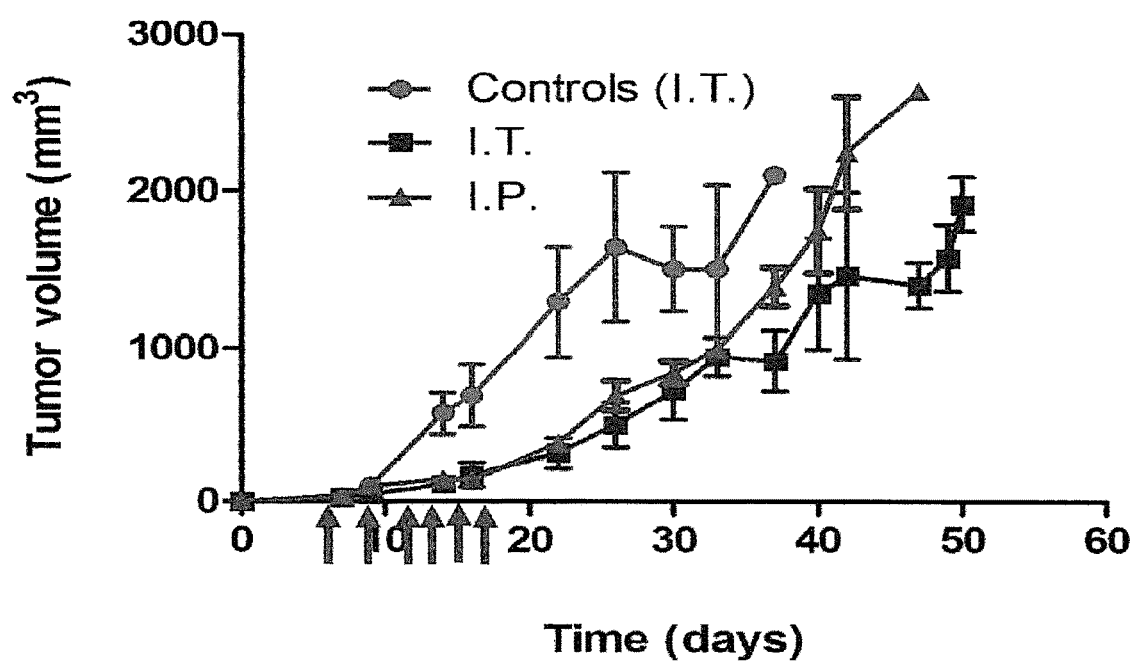
Figure 8:
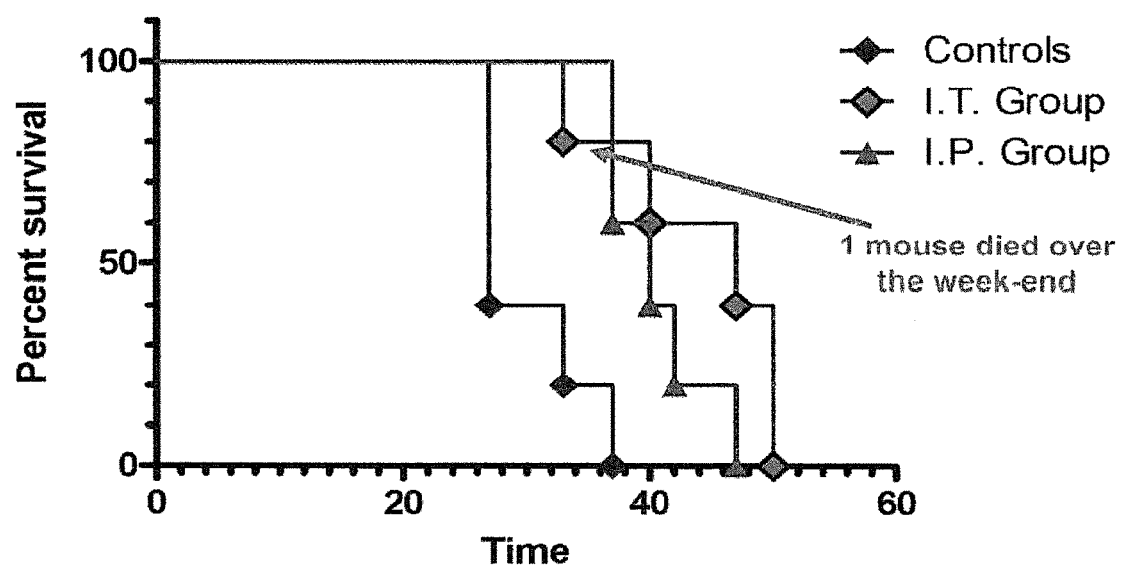

The effectiveness of the cpIL-4BAD fusion protein was assessed in athymic mice after the development of subcutaneous glioma tumors with U 251 tumor cells. More specifically, cpIL-4BAD was injected intratumorally (IT) at 100 g/kg (6 injections) and intraperitoneally (IP) 100 µg/kg (6 injections). 0.2% HAS/PBS was used as a vehicle control. The assessed end points were tumor size and survival. The results indicated that IT administration of cpIL-4BAD regressed the tumor growth significantly compared to the placebo control-treated animals after 6 injections. IP administration regressed the tumors dramatically compared to IT treated mice. Tumors in both groups of mice recurred beyond day 40, when the mice in control groups were euthanized for ethical reasons, as the tumors were of 2000 mm$^3$ on day 36 (FIG. 7). cpIL-4BAD-treated mice also survived longer than placebo treated mice (FIG. 8).

Example 3

Six additional IL-4Rα positive cell lines were tested for their sensitivity to the cpIL-4BAD fusion protein and cpIL-4PE under identical experimental conditions. IC$_{50}$ values were determined by counting the cells using the trypan blue exclusion technique (Table 3).

TABLE 3

IC$_{50}$ values of IL-4Rα positive cell lines.

| | | IC$_{50}$ (ng/mL) | |
|---|---|---|---|
| Cell Line | Origin | cpIL-4BAD | cpIL-4PE |
| YCUT891 | Tongue | 11.0 | 8.0 |
| YCUM862 | Oropharynx | 1.1 | 0.6 |
| KCCOR891 | Oral Floor | 0.15 | 9.0 |
| KCCL871 | Larynx | 0.5 | 1.5 |
| YCUM911 | Oropharynx | 0.2 | 4.5 |
| KCCTCM901 | Metastasis to the chest fluid | 1.0 | 0.7 |

Example 4

Figure 9:
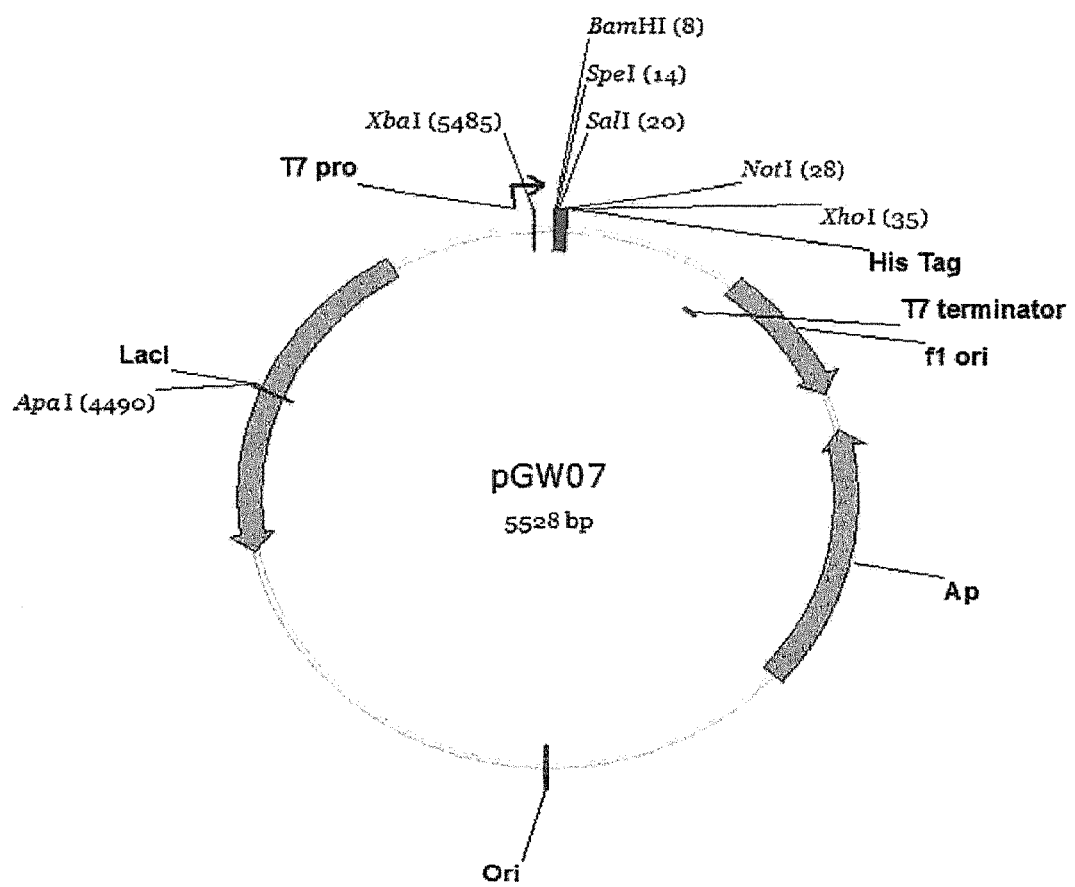

IL-4BAD, cpIL-4BAD and cpS4-BAD fusion proteins were expressed and purified. More specifically, cDNAs of IL-4BAD, cpIL-4BAD and cpS4-BAD were PCR cloned into BamHI/XhoI sites of a pGW07 E. coli. expression vector (FIG. 9). The obtained vectors were verified by DNA sequencing (FIGS. 10A-D).

Protein expression was performed in E. coli cells. IL-4BAD, cpIL-4BAD and cpS4-BAD proteins were expressed in 1 L cultures in insoluble form, purified under denaturing conditions using IMAC, followed by "quick dilution" protein refolding. Refolding by "quick dilution" generated intact proteins free of aggregates, as determined by non-reducing SDS-PAGE. Final sample size and concentrations were as follows: IL-4BAD was about 3.5 mL at 0.24 mg/mL, determined by UV280 nm (UV280 nm Abs at 1 mg/ml=1.14); cpIL-4BAD was about 3.5 mL at 0.23 mg/mL, determined by UV280 nm (UV280 nm Abs at 1 mg/mL=1.13); and cpS4-BAD was about 3.5 mL at 0.23 mg/mL, determined by UV280 nm (UV280 nm Abs at 1 mg/ml=1.25). Protein was stored in a storage buffer composition: 500 nM NaCL, 10 mM Na-Phosphate, pH 7.0, 1% glycerol, 1 µM EDTA, 0.01% Tween 20.

BL21(DE3)pLysS-RARE2 cells were transformed with IL-4BAD, cpIL-4BAD and cpS4-BAD protein expression constructs, plated on LB plates supplemented with Amp at 100 g/mL, and incubated overnight at 37° C. The next day, colonies from the plate were scraped and re-suspended in liquid LB medium with 100 g/mL of Amp. The cultures were then grown at 37° C., with aeration, and protein expression was induced by 1 mM IPTG when the cell culture reached an OD$_{600}$ of about 0.5. Induction lasted for about 4 hours at 30° C. The cell pellet was then collected and stored at −20° C. 10 µL samples of uninduced and induced culture were lysed by boiling at 95° C. for 10 minutes in 50 µL of reducing protein loading buffer and run on an SDS-PAGE gel. Cells from a 1 mL sample collected at 4 hours post-induction were lysed in hypotonic buffer, sonicated and centrifuged for 10 minutes at 13,000 rpm. Aliquots from the soluble and insoluble fraction were boiled in reducing protein loading buffer and analyzed on an SDS-PAGE gel. Estimated expression levels observed for IL-4BAD, cpIL-4BAD proteins was more than 50 mg/L of crude material. Estimated expression levels observed for cpS4-BAD was more than 50 mg/L. IL-4BAD was found to be almost completely insoluble, with some possible soluble form (less than 5%). cpS4-BAD were mainly in the insoluble fraction.

The cell pellets from the induced cultures were lysed at room temperature and the inclusion bodies fraction was collected and washed with PBS-T. The insoluble material was solubilized in 8M Urea and bound to 3 mL Ni-charged resin. The resin was washed with 15 CV of wash buffer and the bound protein was eluted in 8 CV elutions of step gradient of imidazole in wash buffer. 7.5 µL from each fraction was analyzed on a SDS-PAGE gel. The fractions with the highest amount of IL-4BAD (about 6 mg) and cpIL-4BAD (about 8 mg) were combined and refolded. The remaining fractions were stored at −20° C.

The IL-4BAD and cpIL-4BAD fractions were combined, reduced by the addition of 1 mM DTT and subjected to a slow step-wise dialysis against storage buffer (150 mM NaCl, 10 mM HEPES, pH 7.4, 0.01% Tween 20) supplemented with a decreasing concentration of urea at each dialysis buffer change. The protein concentration was measured after each dialysis step by UV Spectroscopy: IL-4BAD was about 0.8 mg; and cpIL-4BAD was about 0.45 mg. The samples were then run on an SDS-PAGE gel.

25 µL of each protein (~0.6 mg/mL, 200 mM Imidazole fraction) was diluted in 1 mL of the following buffers: 20 mM HEPES, pH 7.4, 1% glycerol, 10 µM EDTA, 0.01% Tween (Buffer 1); 10 mM Na-Phosphate, pH 7.0, 1% Glycerol, 10 µM EDTA, 0.01% Tween (Buffer 2); and PBS, pH 7.2 (Buffer 3). The samples were stored overnight at room temperature. The next day, the samples were spun for 10 minutes at 13,000 rpm and the presence of the pellet in each sample was observed and recorded in Table 2: (+++) indicates an abundant pellet; (−) indicates no visible pellet.

TABLE 2

IL-4BAD and cpIL-4BAD pellets in Buffers 1, 2 and 3.

| | | | IL4-BAD | Pellet after refolding | cpIL4-BAD, | Pellet after refolding |
|---|---|---|---|---|---|---|
| 10 mM DTT | Buffer 1 | NaCl, 100 mM | Sample 1 | (+++) | Sample 13 | (+++) |
| | | NaCl, 500 mM | Sample 2 | (+++) | Sample 14 | (++) |
| | | NaCl, 20 mM | Sample 3 | (++) | Sample 15 | (+++) |
| | Buffer 2 | NaCl, 100 mM | Sample 4 | (−) | Sample 16 | (+++) |
| | | NaCl, 500 mM | Sample 5 | (+) | Sample 17 | (++) |
| | | NaCl, 20 mM | Sample 6 | (+++) | Sample 18 | (+++) |
| | Buffer 3 | | Sample 25 | (++) | Sample 27 | (+++) |
| w/o reducing agents | Buffer 1 | NaCl, 100 mM | Sample 7 | (+) | Sample 19 | (++) |
| | | NaCl, 500 mM | Sample 8 | (+) | Sample 20 | (++) |
| | | NaCl, 20 mM | Sample 9 | (−) | Sample 21 | (++) |
| | Buffer 1 | NaCl, 100 mM | Sample 10 | (−) | Sample 22 | (++) |
| | | NaCl, 500 mM | Sample 11 | (+) | Sample 23 | (+) |
| | | NaCl, 20 mM | Sample 12 | (+) | Sample 24 | (+++) |
| | Buffer 3 | | Sample 26 | (+) | Sample 28 | (−) |

The samples were also analyzed on non-reducing SDS-PAGE gel. Refolded samples were concentrated to 100 μL using Amicon 10 kDa MWCO, spun down, and a 7.5 μL aliquot of each sample was run on an SDS-PAGE gel.

The purification process was repeated using quick dilution folding. 4 ml of 200 mM imidazole fractions containing IL-4BAD, cpI-4BAD or cpS4-BAD was quickly diluted into 200 mL of refolding buffer (500 mM NaCl, 10 mM Na-Phosphate, pH 7.0 or 6.0 or 7.8, 1% Glycerol, 10 μM EDTA, 0.01% Tween), incubated overnight at room temperature, spun down for 20 minutes at 4,000 rpm at 4° C., concentrated to 3 mL using an Amicon 10 kDa MWCO, and buffer exchanged into storage buffer (500 mM NaCl, 10 mM Na-Phosphate, pH 7.0 or 6.0 or 7.8, 1% Glycerol, 1 μM EDTA, 0.01% Tween) using a DG-10 column. Final sample concentrations were as follows: 3.5 mL of IL-4BAD at about 0.24 mg/mL; 3.5 mL of cpIL-4BAD at about 0.23 mg/mL. The final samples were run on an SDS-PAGE gel.

The final concentration of cpS4-BAD was about 3.5 mL at about 0.23 mg/mL. The final sample was run on an SDS-PAGE gel.

Example 5

A pKFR4-BAD-H6 fusion protein (FIGS. 11A-B) was prepared as follows. cDNA of pKFR4-BAD-H6 was PCR cloned into the NdeI/XhoI sites of a pET-21a(+) vector. The vector was then transformed into HMS174(DE3) cells and induced with 0.1 mM IPTG for 3 hours. Samples were run on an SDS-PAGE gel before and after induction. The cells were pelleted and lysed by ultrasonication in a buffer containing 20 mM Tris-HCl, 300 mM NaCl, 20 mM Imidazole, pH 8.0, and samples were run on an SDS-PAGE gel.

Inclusion bodies were dissolved in a dissolving buffer of 20 mM Tris-HCl, 300 mM NaCl, 20 mM Imidazole, 20 mM beta-ME, 7 M GuaHCl, pH 8.0. The supernatant was then purified by $Ni^{2+}$ affinity chromatography. pKFR4-BAD-H6 was eluted by 20 mM Tris-HCl, 300 mM NaCl, 300 mM Imidazole, 8 M Urea, pH 8.0 under reducing and non-reducing conditions. Samples were taken throughout the purification process.

After purification, pKFR4-BAD-H6 was dialyzed in dialysis buffer: 0.1% TFA, 30% acetonitrile under reducing conditions and non-reducing conditions, yielding a concentration of about 2.67 mg/mL.

Example 6

To evaluate the potency of fusion proteins on IL-4R-expressing cell lines, HH suspension cells that express Type I IL-4R, were cultured in RPMI1640 (from Gibco) containing 10% FBS (from Life Technologies), 2 mM L-glutamine (from Gibco) and 10 mM HEPES (from Gibco). cpS4-BAD was added to the cell suspension. The cell suspension was poured into a 96-well Isoplate in an amount of about $1 \times 10^4$ cells/well. The cell suspensions were incubated at 37° C. in a 5% $CO_2$ incubator for 48 hours. Before the end of the 48-hour incubation, 100 μCi/mL of [$^3$H]-thymidine in complete medium was prepared and 10 μL was added into each well of the culture. After 6 hours of incubation with [$^3$H]-thymidine, 50 μL of 50% trichloroacetic acid was slowly added into each well and incubated at 4° C. for 2 hours. The plates were then washed five times with $dH_2O$, and air-dried. 100 μL of scintillation liquid was added to each well and the plates were left at room temperature overnight. The next day, the radioactivity was read in a MicroBeta Trilux. Data was collected and standardized using the reading from the control well (cell only). The background reading (blank) was subtracted from the readings of all the wells, and the inhibition (% inhibition) was calculated. The $IC_{50}$ of cpS4-BAD was about 126.3 ng/mL, which was about 3 times more potent than MDNA55 (cpIL4-PE; 362.4 ng/mL) which was used as a reference.

All citations are hereby incorporated by reference.

The present invention has been described with regard to one or more embodiments. However, it will be apparent to persons skilled in the art that a number of variations and modifications can be made without departing from the scope of the invention as defined in the claims.

What is claimed is:

1. A fusion protein comprising an interleukin-4 (IL-4) receptor binding protein and a pro-apoptotic Bcl-2 family polypeptide, wherein the fusion protein comprises the amino acid sequence of any one of SEQ ID NOs:24-27.

2. The fusion protein of claim 1, wherein the fusion protein comprises the amino acid sequence of SEQ ID NO:24.

3. The fusion protein of claim 1, wherein the fusion protein comprises the amino acid sequence of SEQ ID NO:25.

4. The fusion protein of claim 1, wherein the fusion protein comprises the amino acid sequence of SEQ ID NO:26.

5. The fusion protein of claim 1, wherein the fusion protein comprises the amino acid sequence of SEQ ID NO:27.

6. A pharmaceutical composition comprising the fusion protein of claim 1.

7. A nucleic acid molecule comprising the nucleic acid sequence of any one of SEQ ID NOs: 35-38.

8. The nucleic acid molecule of claim 7, wherein the nucleic acid molecule comprises the nucleic acid sequence of SEQ ID NO:35.

9. A vector comprising the nucleic acid molecule of claim 8.

10. An isolated or cultured host cell comprising the vector of claim 9.

11. The nucleic acid molecule of claim 7, wherein the nucleic acid molecule comprises the nucleic acid sequence of SEQ ID NO:36.

12. A vector comprising the nucleic acid molecule of claim 11.

13. An isolated or cultured host cell comprising the vector of claim 12.

14. The nucleic acid molecule of claim 7, wherein the nucleic acid molecule comprises the nucleic acid sequence of SEQ ID NO:37.

15. A vector comprising the nucleic acid molecule of claim 14.

16. An isolated or cultured host cell comprising the vector of claim 15.

17. The nucleic acid molecule of claim 7, wherein the nucleic acid molecule comprises the nucleic acid sequence of SEQ ID NO:38.

18. A vector comprising the nucleic acid molecule of claim 17.

19. An isolated or cultured host cell comprising the vector of claim 18.

* * * * *